United States Patent
Fiorina

(10) Patent No.: US 10,751,373 B2
(45) Date of Patent: *Aug. 25, 2020

(54) PD-L1 EXPRESSING HEMATOPOIETIC STEM CELLS AND USES

(71) Applicant: The Children's Medical Center Corporation, Boston, MA (US)

(72) Inventor: Paolo Fiorina, Boston, MA (US)

(73) Assignee: The Children's Medical Center Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/685,238

(22) Filed: Nov. 15, 2019

(65) Prior Publication Data

US 2020/0085878 A1 Mar. 19, 2020

Related U.S. Application Data

(63) Continuation of application No. 16/215,932, filed on Dec. 11, 2018, now Pat. No. 10,517,899, which is a continuation of application No. 15/745,553, filed as application No. PCT/US2016/043053 on Jul. 20, 2016, now abandoned.

(60) Provisional application No. 62/194,969, filed on Jul. 21, 2015.

(51) Int. Cl.
| | |
|---|---|
| *A61K 35/28* | (2015.01) |
| *C07K 16/28* | (2006.01) |
| *C12N 5/0789* | (2010.01) |
| *A61P 3/10* | (2006.01) |
| *C07K 14/705* | (2006.01) |
| *A61K 39/00* | (2006.01) |

(52) U.S. Cl.
CPC ............... *A61K 35/28* (2013.01); *A61P 3/10* (2018.01); *C07K 14/70532* (2013.01); *C07K 16/2818* (2013.01); *C12N 5/0647* (2013.01); *A61K 2039/505* (2013.01); *C07K 2317/75* (2013.01); *C12N 2500/90* (2013.01); *C12N 2501/113* (2013.01); *C12N 2501/125* (2013.01); *C12N 2501/145* (2013.01); *C12N 2501/17* (2013.01); *C12N 2501/91* (2013.01); *C12N 2501/999* (2013.01); *C12N 2510/00* (2013.01)

(58) Field of Classification Search
CPC .............. A61K 2035/124; A61K 35/28; C12N 2510/00; C12N 5/0647; C12N 2502/1171; C12N 15/907
See application file for complete search history.

(56) References Cited

U.S. PATENT DOCUMENTS

| | | |
|---|---|---|
| 5,460,964 A | 10/1995 | McGlave et al. |
| 5,635,387 A | 6/1997 | Fei et al. |
| 5,677,136 A | 10/1997 | Simmons et al. |
| 5,716,827 A | 2/1998 | Tsukamoto et al. |
| 5,750,397 A | 5/1998 | Tsukamoto et al. |
| 5,759,793 A | 6/1998 | Schwartz et al. |
| 5,854,033 A | 12/1998 | Lizardi et al. |
| 6,610,719 B2 | 8/2003 | Paralkar et al. |
| 6,747,037 B1 | 6/2004 | Old et al. |
| 7,592,177 B2 | 9/2009 | Chen et al. |
| 7,951,592 B2 | 5/2011 | Chen et al. |
| 8,071,369 B2 | 12/2011 | Jaenisch et al. |
| 8,168,428 B2 | 5/2012 | Zon et al. |
| 8,309,555 B2 | 11/2012 | Chen et al. |
| 8,481,022 B2 | 7/2013 | Lodie et al. |
| 8,906,677 B2 | 12/2014 | Li et al. |
| 8,932,856 B2 | 1/2015 | Jaenisch et al. |
| 9,028,811 B2 | 5/2015 | Zon et al. |
| 9,056,085 B2 | 6/2015 | Zon et al. |
| 9,402,852 B2 | 8/2016 | Zon et al. |
| 10,023,879 B2 | 7/2018 | Flynn et al. |
| 10,201,557 B2 | 2/2019 | Bishopric et al. |
| 2003/0194803 A1 | 10/2003 | Mellor et al. |
| 2004/0053307 A1 | 3/2004 | Wood et al. |
| 2006/0003452 A1 | 1/2006 | Humeau et al. |
| 2006/0154853 A1 | 7/2006 | Steptoe et al. |
| 2006/0247214 A1 | 11/2006 | Delong et al. |
| 2007/0116691 A1 | 5/2007 | Cambier et al. |
| 2007/0122377 A1 | 5/2007 | Best et al. |
| 2007/0254884 A1 | 11/2007 | Chen et al. |
| 2008/0175825 A1 | 7/2008 | Hampson et al. |
| 2009/0209621 A1 | 8/2009 | Mendell et al. |

(Continued)

FOREIGN PATENT DOCUMENTS

| | | |
|---|---|---|
| CA | 3013683 A1 | 9/2017 |
| CA | 3040048 A1 | 4/2018 |

(Continued)

OTHER PUBLICATIONS

Kamat et al. "MicroRNA screen of human embryonic stem cell differentiation reveals miR-105 as an enhancer of megakaryopoiesis from adult CD34+ cells." Stem Cells 32(5): 1337-1346 (2014).

Kao et al. "Tumor suppressor microRNAs contribute to the regulation of PD-L1 expression in malignant pleural mesothelioma." Journal of Thoracic Oncology 12(9): 1421-1433 (2017).

Nasr et al., "PD-L1 genetic overexpression or pharmacological restoration in hematopoietic stem and progenitor cells reverses autoimmune diabetes." Science Translational Medicine 9(416):1-14 (2017).

(Continued)

*Primary Examiner* — Lynn Y Fan
(74) *Attorney, Agent, or Firm* — Nixon Peabody LLP; David S. Resnick

(57) ABSTRACT

Embodiments disclosed here provide engineered modified hematopoietic stem cells (HSCs), artificially prostaglandin E2 ($PGE_2$)-stimulated HSCs, compositions comprising these HSCs, methods of using these modified HSCs for treating autoimmune diseases and disorders and for suppressing the immune system. In particular, the engineered modified HSCs or $PGE_2$-stimulated HSCs express the surface marker, programmed cell death-1 ligand 1 (PD-L1).

19 Claims, 15 Drawing Sheets

Specification includes a Sequence Listing.

(56) References Cited

U.S. PATENT DOCUMENTS

| | | |
|---|---|---|
| 2010/0203056 A1 | 8/2010 | Irving et al. |
| 2010/0233804 A1 | 9/2010 | Zhou et al. |
| 2010/0310525 A1 | 12/2010 | Chevalier et al. |
| 2011/0076678 A1 | 3/2011 | Jaenisch et al. |
| 2011/0110899 A1 | 5/2011 | Shi et al. |
| 2012/0003189 A1 | 1/2012 | Pelus et al. |
| 2012/0028351 A1 | 2/2012 | Li et al. |
| 2012/0202288 A1 | 8/2012 | Mendlein et al. |
| 2012/0251514 A1 | 10/2012 | Fowler et al. |
| 2012/0263692 A1 | 10/2012 | Bertone |
| 2012/0264218 A1 | 10/2012 | Lin et al. |
| 2012/0277652 A1 | 11/2012 | Zhao et al. |
| 2013/0102074 A1 | 4/2013 | Jaenisch et al. |
| 2013/0323832 A1 | 12/2013 | Munn et al. |
| 2014/0030232 A1 | 1/2014 | Shoemaker et al. |
| 2014/0234373 A1 | 8/2014 | Mellor et al. |
| 2014/0341933 A1 | 11/2014 | Riley et al. |
| 2014/0369972 A1 | 12/2014 | Shoemaker et al. |
| 2015/0139994 A1 | 5/2015 | Xu |
| 2015/0366914 A1 | 12/2015 | Yu et al. |
| 2017/0211042 A1 | 7/2017 | Riley et al. |
| 2017/0246279 A1 | 8/2017 | Berger et al. |
| 2018/0112180 A1 | 4/2018 | Robbins et al. |

FOREIGN PATENT DOCUMENTS

| | | |
|---|---|---|
| RU | 2425876 C2 | 8/2011 |
| WO | 2000038663 A2 | 7/2000 |
| WO | 2001012596 A1 | 2/2001 |
| WO | 2006072016 A2 | 7/2006 |
| WO | 2007071456 A1 | 6/2007 |
| WO | 2007/112084 A2 | 10/2007 |
| WO | 2008/070310 A2 | 6/2008 |
| WO | 2008073748 A1 | 6/2008 |
| WO | 2009/023566 A2 | 2/2009 |
| WO | 2009/086425 A1 | 7/2009 |
| WO | 2009/155041 A2 | 12/2009 |
| WO | 2010/096264 A2 | 8/2010 |
| WO | 2010/108028 A2 | 9/2010 |
| WO | 2010/108126 A2 | 9/2010 |
| WO | 2011/031875 A2 | 3/2011 |
| WO | 2011060381 A1 | 5/2011 |
| WO | 2011127180 A1 | 10/2011 |
| WO | 2012/021845 A2 | 2/2012 |
| WO | 2013040552 A2 | 3/2013 |
| WO | 2013/082241 A2 | 6/2013 |
| WO | 2013/082243 A1 | 6/2013 |
| WO | 2014/152603 A1 | 9/2014 |
| WO | 2015/134652 A1 | 9/2015 |
| WO | 2016/077574 A1 | 5/2016 |
| WO | 2016/123100 A1 | 8/2016 |
| WO | 2016/123117 A1 | 8/2016 |
| WO | 2016/142532 A1 | 9/2016 |
| WO | 2016/161196 A1 | 10/2016 |
| WO | 2017015320 A1 | 1/2017 |
| WO | 2017040078 A1 | 3/2017 |
| WO | 2017069958 A2 | 4/2017 |
| WO | 2017/078807 A1 | 5/2017 |
| WO | 2017100587 A1 | 6/2017 |

OTHER PUBLICATIONS

O'Connell et al. "MicroRNAs enriched in hematopoietic stem cells differentially regulate long-term hematopoietic output." Proceedings of the National Academy of Sciences 107(32): 14235-14240 (2010).
Ooi et al. "MicroRNA-125b expands hematopoietic stem cells and enriches for the lymphoid-balanced and lymphoid-biased subsets." Proceedings of the National Academy of Sciences 107(50): 21505-21510 (2010).
Paladini et al. "Targeting microRNAs as key modulators of tumor immune response." Journal of Experimental & Clinical Cancer Research 35(1): 103 pp. 1-19 (2016).
Roden et al. "MicroRNAs in control of stem cells in normal and malignant hematopoiesis." Current Stem Cell Reports 2(3): 183-196 (2016).
Wang et al. "The roles of microRNAs in regulating the expression of PD-1/PD-L1 immune checkpoint." International Journal of Molecular Sciences 18(12): 2540 pp. 1-11 (2017).
Xu et al. "miR-424 (322) reverses chemoresistance via T-cell immune response activation by blocking the PD-L1 immune checkpoint." Nature Communications 7(1): 1-13 (2016).
Yalcin et al. "Microma mediated regulation of hematopoietic stem cell aging." Blood 124(21): 602 (2014).
Ansari et al., "The Programmed Death-1 (PD-1) Pathway Regulates Autoimmune Diabetes in Nonobese Diabetic (NOD) Mice", J Exp Med., 198(1):63-69 (2003).
Bachar-Lustig et al., "Megadose of T cell-depleted bone marrow overcomes MHC barriers in sublethally irradiated mice" Natural Medicine 1(12):1268-1273 (1995).
Bluestone et al., "Genetics, pathogenesis and clinical interventions in type 1 diabetes." Nature 464 (7293):1293-1300 (2010).
Carvello et al., "Inotuzumab Ozogamicin Murine Analog—Mediated B-Cell Depletion Reduces Anti-islet Allo-and Autoimmune Responses." Diabetes 61(1):155-165 (2012).
Cortez et al., "PDL1 Regulation by p53 via miR-34." JNCI: Journal of the National Cancer Institute 108:1-9 (2016).
Couri et al., "C-peptide levels and insulin independence following autologous nonmyeloablative hematopoietic stem cell transplantation in newly diagnosed type 1 diabetes mellitus." Jama 301(15):1573-1579 (2009).
Cutler et al., "Prostaglandin-modulated umbilical cord blood hematopoietic stem cell transplantation" Blood 122 (17):3074-3081 (2013).
D'Addio et al., "Autologous nonmyeloablative hematopoietic stem cell transplantation in new-onset type 1 diabetes: a multicenter analysis." Diabetes 63(9):3041-3046 (2014).
D'Addio et al., "The link between the PDL1 costimulatory pathway and Th17 in fetomaternal tolerance" J. Immunol. 187(9):4530-41 (2011).
DCCT Group (Diabetes Control and Complications Trial Research Group) "Effect of intensive therapy on residual beta-cell function in patients with type 1 diabetes in the diabetes control and complications trial. A randomized, controlled trial." Ann Intern Med. 128:517-523 (1998).
Fife et al., "Insulin-induced remission in new-onset NOD mice is maintained by the PD-1-PD-L1 pathway." Journal of Experimental Medicine 203(12):2737-2747 (2006).
Fife et al., "Interactions between programmed death-1 and programmed death ligand-1 promote tolerance by blocking the T cell receptor-induced stop signal." Nature Immunology 10(11):1185-1192 (2009).
Filippi et al., "Immunoregulatory mechanisms triggered by viral infections protect from type 1 diabetes in mice." The Journal of Clinical Investigation 119(6):1515-1523 (2009).
Fiorina et al. "Immunological Applications of Stem Cells in Type 1 Diabetes." Endocrine Reviews 32(6): 725-754 (2011).
Fiorina et al., "Immunomodulatory function of bone marrow-derived mesenchymal stem cells in experimental autoimmune type 1 diabetes." The Journal of Immunology 183(2):993-1004 (2009).
Fiorina et al., "Targeting CD22 reprograms B-cells and reverses autoimmune diabetes" Diabetes 57(11):3013-24 (2008).
Fiorina et al., "Targeting the CXCR4-CXCL12 Axis Mobilizes Autologous Hematopoietic Stem Cells and Prolongs Islet Allograft Survival via Programmed Death Ligand 1" J Immunol., 186(1):121-31 (2011).
Fowler et al., "Transplant and Autoimmune Therapy Using T-Cells" National Cancer Institute, Federal Register 75 (185):58401-58402 (2010).
Francisco et al., "The PD1 Pathway in Tolerance and Autoimmunity" Immunol Rev. Jul. 236:219-242 (2010).
Grenda et al., "New Dancing Couple: PD-L1 and Micro RNA." Scandinavian Journal of Immunology 86(3)130-134 (2017).
Gur et al., "Immune regulatory activity of CD34+ progenitor cells: evidence for a deletion-based mechanism mediated by TNF-alpha" Blood 105(6):2585-93 (2005).

(56) References Cited

OTHER PUBLICATIONS

He et al., "Programmed death-1 ligands-transfected dendritic cells loaded with glutamic acid decarboxylase 65 (GAD65) inhibit both the alloresponse and the GAD65-reactive lymphocyte response." Clinical & Experimental Immunology 151(1):86-93 (2008).
Herrler et al., "Prostaglandin E positively modulates endothelial progenitor cell homeostasis: an advanced treatment modality for autologous cell therapy." Journal of Vascular Research 46(4):333-346 (2009).
Hoggatt et al., "Prostaglandin E2 enhances hematopoietic stem cell homing, survival, and proliferation." Blood 113 (22):5444-5455 (2009).
Keir et al., "Tissue expression of PD-L1 mediates peripheral T cell tolerance." Journal of Experimental Medicine 203 (4):883-895 (2006).
Lanzinger et al., "Ambivalent effects of dendritic cells displaying prostaglandin E 2-induced indoleamine 2, 3-dioxygenase." European Journal of Immunology 42(5):1117-1128 (2012).
Nasr et al., "Co-transplantation of autologous MSCs delays islet allograft rejection and generates a local immunoprivileged site." Acta Diabetologica 52(5):917-927 (2015).
Nasr et al., "PD-L1+ HSCs Are Immunoregulatory and Revert Experimental Autoimmune Diabetes." Diabetes 64(1) 75th Scientific Sessions of the American-Diabetes-Association, Boston, MA (2015).
Nasr et al., "The rise, fall, and resurgence of immunotherapy in type 1 diabetes", Pharmacol Res.,98:31-8 (2015).
Nosov et al., "Role of lentivirus-mediated overexpression of programmed death-ligand 1 on corneal allograft survival" Am J Transplant 12(5):1313-1322 (2012).
Pallotta et al., "Forced IDO 1 expression in dendritic cells restores immunoregulatory signalling in autoimmune diabetes." Journal of Cellular and Molecular Medicine 18(10):2082-2091 (2014).
Pen et al., "Interference with PD-L1/PD-1 co-stimulation during antigen presentation enhances the multifunctionality of antigen-specific T cells" Gene Therapy 21:262-271 (2014).
Petrelli et al., "IL-21 is an antitolerogenic cytokine of the late-phase alloimmune response." Diabetes 60:3223-3234 (2011).
Rachamim et al., "Tolerance induction by 'megadose' hematopoietic transplants: donor-type human CD34 stem cells induce potent specific reduction of host anti-donor cytotoxic T lymphocyte precursors in mixed lymphocyte culture" Transplantation, 65(10):1386-93 (1998).
Steptoe et al., "Autoimmune diabetes is suppressed by transfer of proinsulin-encoding Gr-1+ myeloid progenitor cells that differentiate in vivo into resting dendritic cells" Diabetes 54(2):434-42 (2005).
Tian et al., "Induction of robust diabetes resistance and prevention of recurrent type 1 diabetes following islet transplantation by gene therapy." The Journal of Immunology 179(10):6762-6769 (2007).
Vergani et al., "A novel clinically relevant strategy to abrogate autoimmunity and regulate alloimmunity in NOD mice." Diabetes 59(9):2253-2264 (2010).
Voltarelli et al. "Autologous nonmyeloablative hematopoietic stem cell transplantation in newly diagnosed type 1 diabetes mellitus" JAMA 297 (14): 1568-76 (2007).
Wang et al., "Protective role of programmed death 1 ligand 1 in nonobese diabetic mice: the paradox in transgenic models." Diabetes 57(7):1861-1869 (2008).
Yokosuka et al., "Programmed cell death 1 forms negative costimulatory microclusters that directly inhibit T cell receptor signaling by recruiting phosphatase SHP2" J. Exp. Med. 209:1201-17 (2012).
Zheng et al., "Ex Vivo Expanded Hematopoietic Stem Cells Overcome the MHC Barrier in Allogeneic Transplantation", Cell Stem Cell 9:119-130 (2011).
Barany. "Genetic disease detection and DNA amplification using cloned thermostable ligase." Proc. Natl. Acad. Sci. USA 88(1): 189-193 (1991).

Beilhack et al. "Purified Allogeneic Hematopoietic Stem Cell Transplantation Blocks Diabetes Pathogenesis in NOD Mice." Diabetes. 52(1): 59-68 (2003).
Ben Nasr et al. "The rise, fall, and resurgence of immunotherapy in type 1 diabetes" Pharmacol. Res. 98: 31-38 (2015).
Daneman. "Type 1 diabetes." Lancet 367(9513): 847-858 (2006).
Guatelli et al. "Isothermal, in vitro amplification of nucleic acids by a multienzyme reaction modeled after retroviral replication." Proc. Natl. Acad. Sci USA 87(5): 1874-1878 (1990).
Guleria et al. "Mechanisms of PD LI-mediated regulation of autoimmune diabetes." Clin. Immunol. 125(1): 16-25 (2007).
Hartshorn et al. "Ex vivo expansion of hematopoietic stem cells using defined culture media." Cell Technology for Cell Products, R. Smith (ed.), Springer Netherlands, pp. 221-224 (2007).
Haynesworth et al. "Cell surface antigens on human marrow-derived mesenchymal cells are detected by monoclonal antibodies." Bone 13(1): 69-80 (1992).
Heneghan et al. "Autoimmune Hepatitis" Lancet 382(9902): 1433-1444 (2013).
Khoury et al. "The roles of the new negative T cell costimulatory pathways in regulating autoimmunity." Immunity 20(5): 529-538 (2004).
Kwoh et al. "Transcription-based amplification system and detection of amplified human immunodeficiency virus type 1 with a bead-based sandwich hybridization format." Proc. Natl. Acad. Sci USA 86(4): 1173-1177 (1989).
Lemoli et al. "Hematopoietic stem cell mobilization." Haematologica 93(3): 321-324 (2008).
Liu et al. "Ex vivo expansion ofhematopoietic stem cells derived from umbilical cord blood in rotating wall vessel" J. Biotechnol. 124(3): 592-601 (2006).
Lizard et al. "Exponential amplification of recombinant-RNA hybrization probes." Bio/Technology 6(10): 1197-1202 (1988).
Munn et al. "Indoleamine 2,3 dioxygenase and metabolic control of immune responses." Trends Immunol. 34(3): 137-143 (2013)\.
Okita et al. "Generation of mouse induced pluripotent stem cells without viral vectors." Science 322(5903): 949-953 (2008).
Ozkaynak et al. "Programmed death-I targeting can promote allograft survival." J Immunol. 69(11): 6546-6553 (2002).
Pelus. "Peripheral blood stem cell mobilization: new regimens, new cells, where do we stand." Curr. Opin. Hematol. 15(4): 285-292 (2008).
Pittenger et al. "Multilineage potential of adult human mesenchymal stem cells." Science 284(5411): 143-147 (1999).
Prockop. "Marrow stromal cells as stem cells for nonhematopoietic tissues." Science 276(5309): 71-74 (1997).
Riella et al. "Role of the PD—1 pathway in the immune response." Am. J Transplant. 12(10): 2575-2587 (2012).
Steidl et al. "Gene expression profiling identifies significant differences between the molecular phenotypes of bone marrow-derived and circulating human CD34+ hematopoietic stem cells." Blood 99(6): 2037-2044 (2002).
Takahashi et al. "Induction of pluripotent stem cells from mouse embryonic and adult fibroblast cultures by defined factors." Cell 126(4): 663-676 (2006).
Varghese et al. "Engineering Musculoskeletal Tissues with Human Embryonic Germ Cell Derivatives." Stem Cells 28(4): 765-774 (2010).
Wernig et al. "In vitro reprogramming of fibroblasts into a pluripotent ES-cell-like state." Nature 448(7151): 318-324 (2007).
White et al. "Acute myocardial infarction." The Lancet 372(9638): 570-584 (2008).
Woltjen et al. "piggyBac ransposition reprograms fibroblasts to induced pluripotent stem cells." Nature 458(7239): 766-770 (2009).
Yang et al. "Expression of PD-L1, PD-L2, PD-1 and CTLA4 in myelodysplastic syndromes is enhanced by treatment with hypomethylating agents." Leukemia 28(6): 1280-1288 (2013).
Zhou et al. "Generation of induced pluripotent stem cells using recombinant proteins." Cell Stem Cell. 4(5): 381-384 (2009).

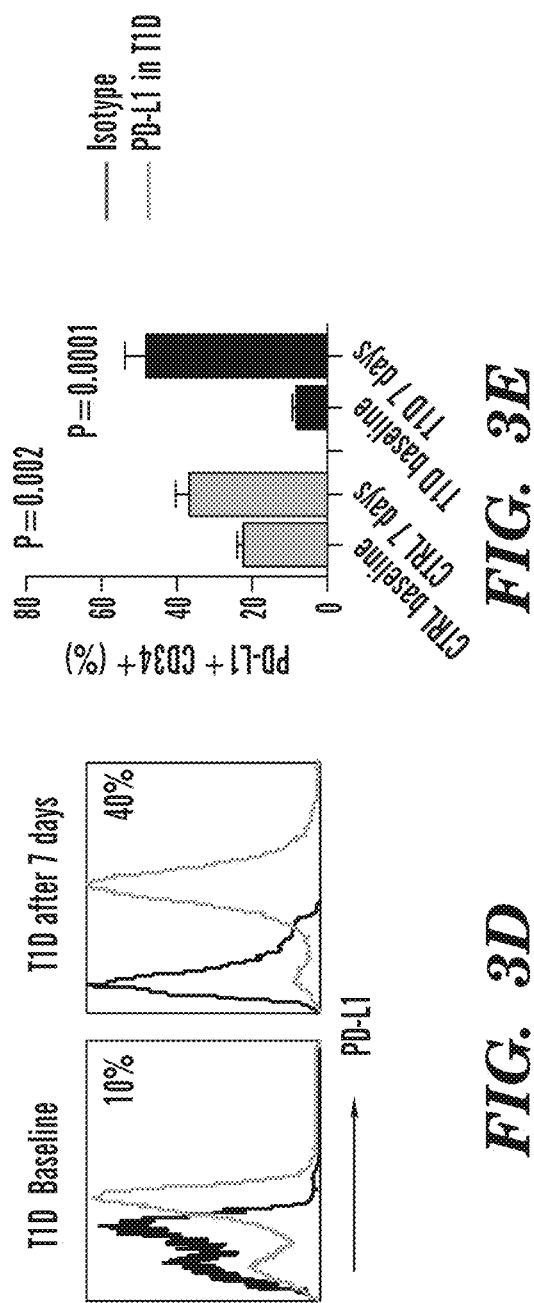

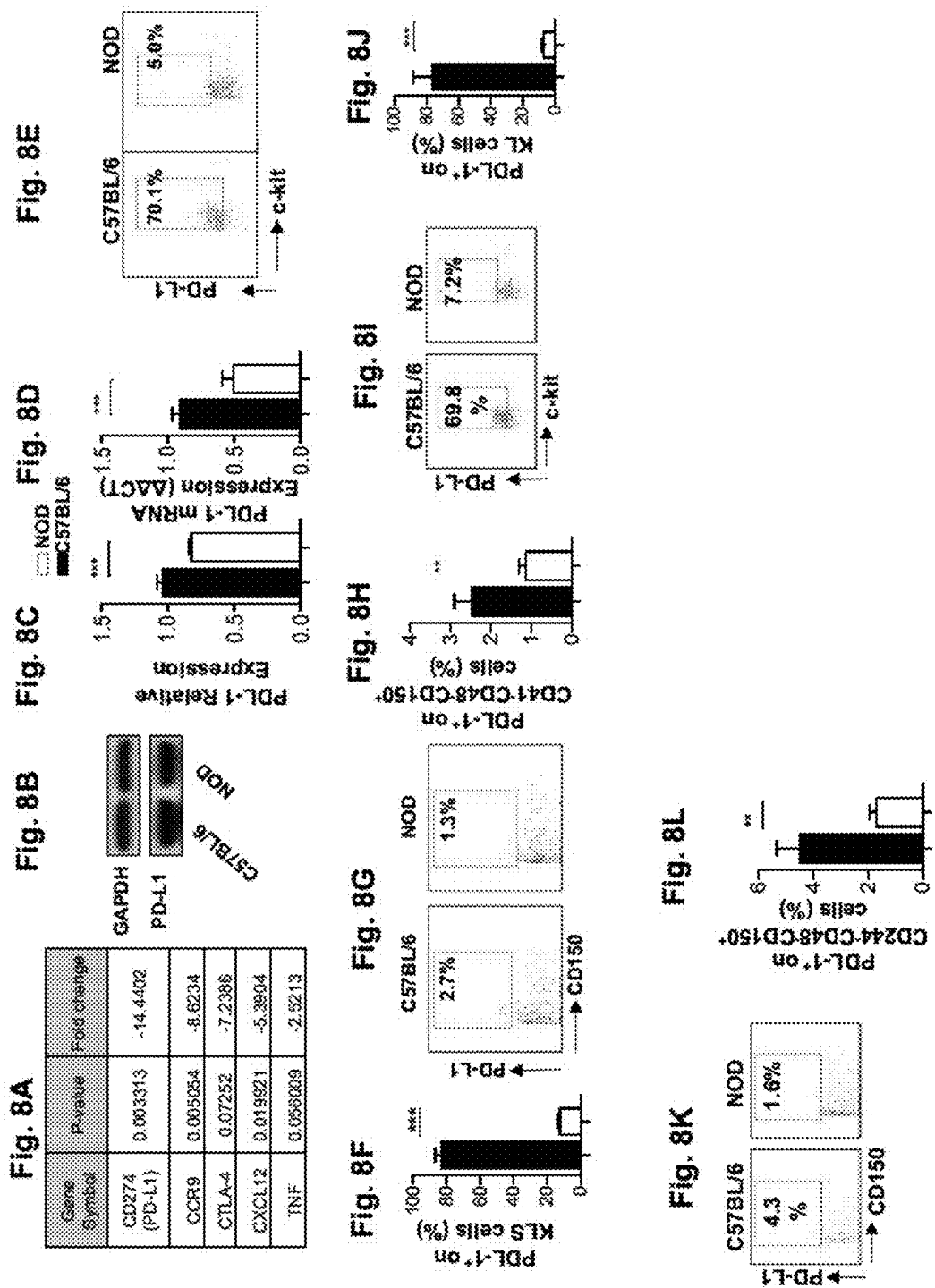

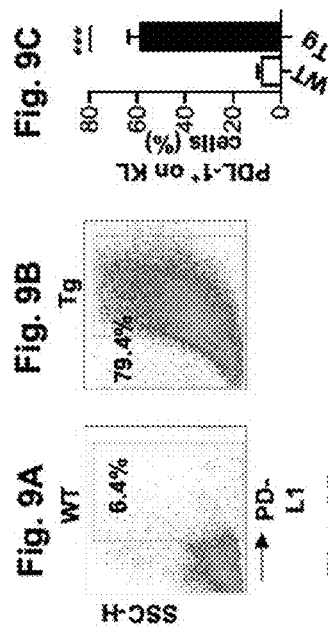
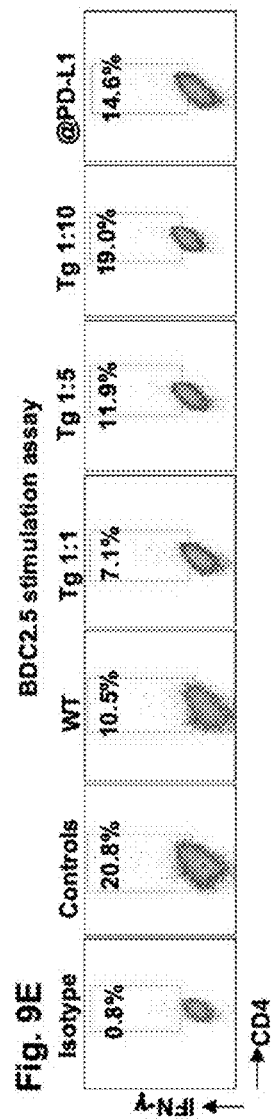
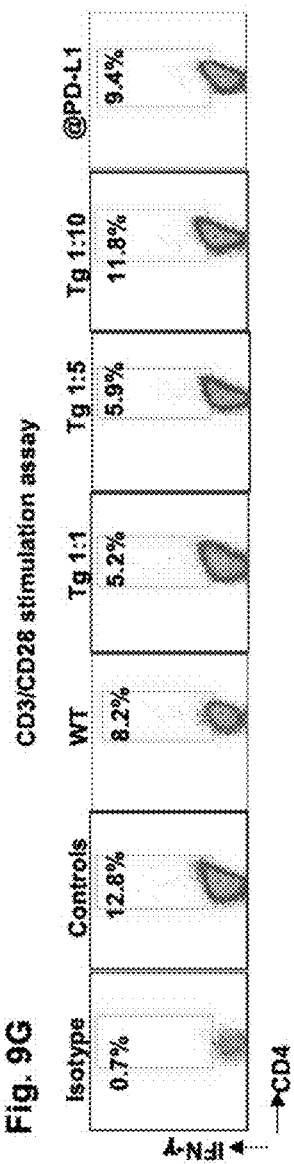

Untreated (n=5)

Tg (n=15)

Doxycycline (n=5)

WT (n=5)

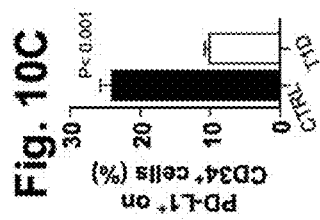
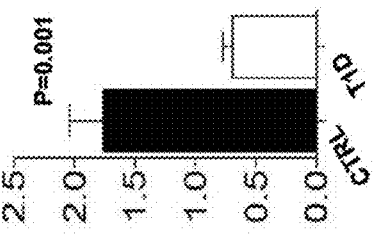
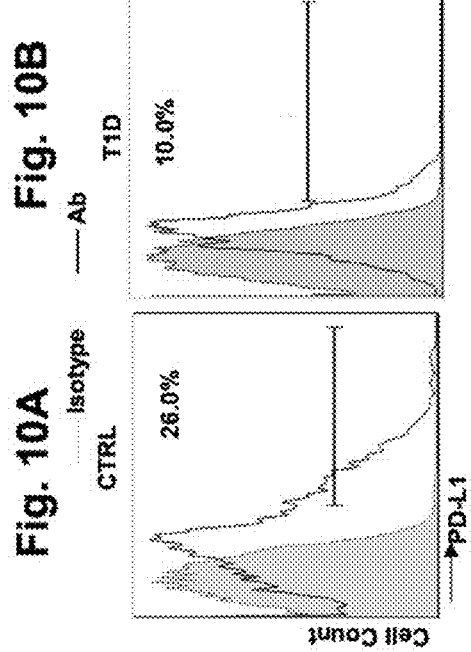
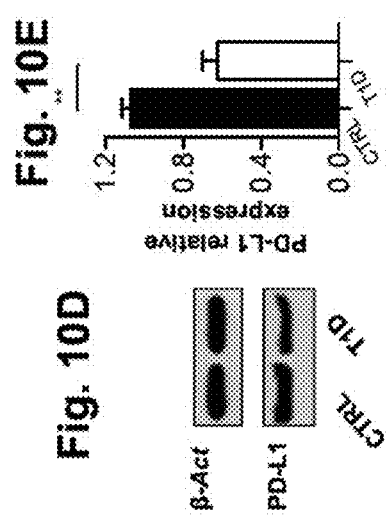

PD-L1 EXPRESSING HEMATOPOIETIC STEM CELLS AND USES

CROSS REFERENCE TO RELATED APPLICATION

This application is a Continuation Application of co-pending U.S. patent application Ser. No. 16/215,932, filed Dec. 11, 2018, which is a Continuation Application of U.S. patent application Ser. No. 15/745,553, filed Jan. 17, 2018, which is a 35 U.S.C. § 371 National Phase Entry Application of International Application No. PCT/US2016/043053 filed Jul. 20, 2016, which designates the U.S., and which claims benefit under 35 U.S.C. § 119(e) of U.S. provisional application No. 62/194,969 filed Jul. 21, 2015, the contents of each of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Jul. 15, 2016, is named 701039-082611-PCT_SL.txt and is 2,286 bytes in size.

BACKGROUND

Immunological approaches have failed in the treatment of autoimmune diseases thus far. For example, in the long-term treatment of autoimmune type 1 diabetes (T1D). Despite considerable effort to halt or delay the destruction of beta-cells in T1D, success remains elusive. Historically, approaches aiming to treat T1D have made a negligible number of subjects insulin-independent. The Diabetes Control and Complications Trial (DCCT) have demonstrated that improving glucose control and preserving β-cell function in individuals with T1D lowered the incidence of diabetic complications.

Stem cells have been used for autoimmune diabetes treatment. Mesenchymal stem cells (MSCs) are fibroblast-like non-hematopoietic progenitor cells with the capacity for adipogenic, chondrogenic, and osteogenic differentiation. MSCs, because of their immunomodulatory properties and their potential to differentiate into insulin-producing cells, represent a viable therapeutic option for autoimmune diabetes A study showed short-term reversal of diabetes in 88% of BALB/c-MSC-treated hyperglycemic NOD mice. However, NOD mice treated with NOD-MSCs remained hyperglycemic. Further reports indicated that treatment with congenic NOR-MSCs resulted in a more pronounced and prolonged reversal of hyperglycemia in treated NOD mice (88% and 62% short-term and long-term reversal respectively), suggesting the potential use of haplo-identical MSCs in autoimmune diabetes. Based on this data, a clinical trial was initiated in the US by the JDRF and by the Osiris Corporation, but interim unpublished results at 1-year of follow-up were disappointing. Furthermore, safety concerns primarily related to potential oncogenic transformation of MSCs may limit their use in the clinical setting. (Moufida Ben Nasr et al., (2015), "The rise, fall, and resurgence of immunotherapy in type 1 diabetes. Pharmacological Research", 98:31-38).

Hematopoietic stem cells (HSCs) transplantation has been reported to yield promising results in long term treatment of T1D. Towever, accumulating clinical data show limited success for long-term insulin independence and for a limited population with the condition. HSCs may provide treatment solutions because HSCs are endowed with immunoregulatory properties and can induce central and peripheral immunological tolerance per se. In 2003, Voltarelli et al. 2007 (JAMA, 297:1568-76) initiated a phase I/II study in (T1D), to evaluate the safety and efficacy of autologous HSC transplantation (AHSCT) using a combined regimen of thymoglobulin plus cyclophosphamide. The latest analysis reported 20 out of 23 of the treated patients with a mean follow-up of 30 months, insulin-free for more than 1 year. However, in the aforementioned studies, it is difficult to distinguish between the effects of concomitant immunosuppressants and the mechanisms of HSC-mediated immunomodulation.

A report from a multicenter analysis on 65 newly-diagnosed T1D individuals treated with AHSCT using a similar protocol to that previously reported showed that insulin independence in nearly 60% of treated subjects was achieved. However, several adverse events have been recorded suggesting this as a therapy for selected T1D individuals only.

Moreover, the AHSCT protocols used in these studies were designed for adults and not for pediatric subjects with T1D, and thus AHSCT can be only considered for a well-defined group of individuals that may benefit from this treatment.

HSCs are endowed with immunoregulatory properties. Preclinical studies demonstrated that T cell-depleted bone marrow-resident CD34+ stem cells overcome MHC barriers in sublethally irradiated mice and that murine HSCs may delete effector cells. This effect can be reverted by the addition of a caspase inhibitor, suggesting a deletion-based mechanism. With respect to human HSCs, the human $CD34^+$ population have been shown to be endowed with potent veto activity and neutralized precursors of cytotoxic T lymphocytes (CTLs) directed against their antigens.

Based on that principle, research focused on finding additional immunological strategies to prevent β-cell loss in subjects with a newly diagnosed T1D have been initiated. Since then, the search for feasible and safe immunological approaches in order to re-establish tolerance toward islet autoantigens (and preserve β-cell function) is ongoing.

SUMMARY

Embodiments of the present disclosure provide programmed cell death-1 ligand 1 (PD-L1) expressing hematopoietic stem cells (HSCs), methods of making these cells, and therapeutic methods of using these cells for the treatment of autoimmune diseases such as type 1 diabetes (T1D), and for the suppression of the immune system in a subject. For example, the therapeutic methods are useful after an organ or bone marrow transplantation, and when a subject has a defect in producing $PD-L1^+$ expressing HSCs, e.g. in Type 1 diabetes (T1D). The disclosure provides $PD-L1^+$ expressing HSCs that are stimulated by prostaglandin E2 ($PGE_2$) treatment or by transduction with an exogenous copy of a nucleic acid that encodes for the PD-L1 protein for promoting PD-L1 expression in the cell after transduction of the nucleic acid.

Type 1 diabetes (T1D) mouse models and human T1D patients have fewer HSCs that express PD-L1 and these HSCs express lower amounts of PD-L1. Supplementing the missing PD-L1 promote immune tolerance prolong survival of transplanted islet grafts in mouse model of T1D and in T1D subjects.

The present disclosure provides that PGE$_2$-stimulated HSCs promote immune tolerance and prolong survival of transplanted islet grafts in mouse model of T1D. The PGE$_2$-stimulated HSCs are now re-programmed to express PD-L1 prior to the PGE$_2$-stimulation. The PGE$_2$-stimulated HSCs also are now re-programmed to express more PD-L1 prior to the PGE$_2$-stimulation. This HSC-mediated immune tolerance occurs via the programmed cell death-1 (PD-1) pathway. Programmed cell death-1 receptor (PD-1) is found on activated T-cells; the programmed cell death-1 receptor ligand (PD-L1, also known as B7-H1) is expressed in other cells, e.g. HSC. The reception/ligand PD-L1/PD-1 interaction deactivates T cell's cytotoxic activity and leads to the immune system inhibition and tolerance.

Moreover, the present disclosure provides that in vivo administration of anti-PD-1 mAb, PIM2, in NOD mice delayed the onset of diabetes and also delayed the islet allografts rejection. A NOD mouse is the mouse model of human TID. If a human is at high risk for developing T1D, administering the PD-L1$^+$ cells can delay the onset of T1D too. Furthermore, this disclosure provides that the PD-L1 expression in HSC can be increased by: (a) an overexpression of a PD-L1 cDNA, e.g., via a lentiviral system or an avian virus system or an adeno-associated virus system; and (b) ex vivo culture of HSC in PGE$_2$, ie., contact with PGE$_2$.

Accordingly, in one embodiment, it is the objective of this disclosure to provide modified PD-L1+ expressing HSCs produced by the overexpression of an exogenous copy of a PD-L1 cDNA in the HSCs. The exogenous copy of cDNA has been introduced or transfected into the HSCs.

In one embodiment, it is the objective of this disclosure to provide an ex vivo method of producing a population of PD-L1$^+$ expressing HSCs by a contact or stimulation with PGE$_2$. The inventors found that under certain conditions, PGE$_2$ stimulates endogenous expression of PD-L1 in HSCs, even the defective HSCs from T1D that have lower expression of PD-L1.

In one embodiment, it is the objective of this disclosure to provide an ex vivo method of producing a population of PD-L1+ expressing HSCs by the overexpression of an exogenous copy of a PD-L1 cDNA.

In one embodiment, it is the objective of this disclosure to provide a method of treating autoimmune disease or suppressing the immune system by using the PD-L1$^+$ expressing HSCs described here.

Accordingly, in one embodiment, provided herein is a population of modified HSCs where the cells carry an exogenous copy of a nucleic acid encoding a PD-L1 or the HSCs are ex vivo stimulated by PGE$_2$ described herein to stimulate PD-L1 expression the cells.

In one embodiment, provided herein is a population of modified HSCs for use in the prevention and treatment of an autoimmune disease or disorder in a subject, for use in suppressing an immune response in a subject, for use in the delay of the onset of T1D in a subject at risk of developing T1D, for use in preventing or delaying an allogenic tissue/organ rejection in a subject, and for use in the treatment of T1D in subjects (adult and pediatric T1D patients). In one embodiment, the modified HSCs carry an exogenous copy of a nucleic acid encoding a PD-L1. The modified HSCs express more PD-L1 compared to non-modified cells not carrying an an exogenous copy of a nucleic acid encoding a PD-L1. In another embodiment, the modified HSCs have been ex vivo stimulated by PGE$_2$ via methods described herein to stimulate PD-L1 expression the cells. In one embodiment, there are more PD-L1 expressing cells in the population of cells after PGE$_2$ stimulation. In another embodiment, the PGE$_2$ stimulated cells express more PD-L1 after stimulation compared to prior to the stimulation.

In one embodiment, provided herein is a population of modified HSCs for use in the manufacture of medicament for the prevention and treatment of an autoimmune disease or disorder in a subject, for the suppressing an immune response in a subject, for delaying of the onset of T1D in a subject at risk of developing T1D, for use in preventing or delaying an allogenic tissue/organ rejection in a subject, and for the treatment of T1D in subjects (adult and pediatric T1D patients). In one embodiment, the modified HSCs carry an exogenous copy of a nucleic acid encoding a PD-L1. In another embodiment, the modified HSCs have been ex vivo stimulated by PGE$_2$ via methods described herein to stimulate PD-L1 expression in the cells.

In one embodiment, provided herein is a composition comprising a population of modified HSCs described herein, where the cells carry an exogenous copy of a nucleic acid encoding a PD-L1.

In one embodiment, provided herein is a composition for transplantation into a subject, for the prevention and treatment of an autoimmune disease or disorder, for suppressing/reducing an immune response in a subject, for use in the delay of the onset of T1D in a subject at risk of developing T1D, for use in preventing or delaying an allogenic tissue/organ rejection in a subject, and for the treatment of T1D in adult and pediatric subjects, the composition comprising the modified HSCs described herein, where the HSCs are modified and carry an exogenous copy of a nucleic acid encoding a PD-L1 or the HSCs are ex vivo stimulated by PGE$_2$ via methods described herein to stimulate PD-L1 expression in the cells. In some embodiment, the HSCs are ex vivo stimulated with both PGE$_2$ and a steroid such as dexamethasone.

In one embodiment, provided herein is a composition the modified HSCs described herein for the manufacture of medicament for use in transplantation into a subject, for the prevention and treatment of an autoimmune disease or disorder, for suppressing/reducing an immune response in a subject, for use in the delay of the onset of T1D in a subject at risk of developing T1D, for use in preventing or delaying an allogenic tissue/organ rejection in a subject, and for the treatment of T1D in adult and pediatric subjects, where the HSCs are modified and carry an exogenous copy of a nucleic acid encoding a PD-L1 or the HSCs are ex vivo stimulated by PGE$_2$ via methods described herein to stimulate PD-L1 expression in the cells. In some embodiment, the HSCs are ex vivo stimulated with both PGE$_2$ and a steroid such as dexamethasone.

In one embodiment of any one of the population of HSCs or composition comprising a population of HSCs, the HSCs are expressing PD-L1. In another embodiment, the HSCs exhibit increased PD-L1 expression. In yet another embodiment, the population of HSCs exhibits an increase proportion of PD-L1$^+$ expressing cells, e.g., an increase of at least one fold.

In one embodiment of any one of the population of HSCs or composition comprising a population of HSCs, the nucleic acid is a copy DNA (cDNA).

In one embodiment of any one of the population of HSCs or composition comprising a population of HSCs, the nucleic acid is a genomic DNA.

In one embodiment of any one of the population of HSCs or composition comprising a population of HSCs, the nucleic acid is integrated into the genome of the cells.

In one embodiment of any one of the population of HSCs or composition comprising a population of HSCs, the nucleic acid is introduced into the HSCs via a vector.

In one embodiment of any one of the population of HSCs or composition comprising a population of HSCs, the vector is a viral vector.

In one embodiment of any one of the population of HSCs or composition comprising a population of HSCs, the viral vector is a lentiviral vector, an avian virus vector or an adeno-associated virus.

In one embodiment of any one of the population of HSCs or composition comprising a population of HSCs, the HSCs are mammalian cells.

In one embodiment of any one of the population of HSCs or composition comprising a population of HSCs, the mammalian cells are human cells.

In one embodiment of any one of the population of HSCs or composition comprising a population of HSCs, prior to the modification with a vector described herein or stimulation with $PGE_2$ described, the HSCs are obtained from the bone marrow, umbilical cord, amniotic fluid, chorionic cord blood, placental blood or peripheral blood.

In one embodiment of any one of the population of HSCs or composition comprising a population of HSCs, the HSCs are obtained from mobilized peripheral blood.

In one embodiment of any one of the population of HSCs or composition comprising a population of HSCs, the HSCs are derived from a healthy individual.

In one embodiment of any one of the population of HSCs or composition comprising a population of HSCs, the HSCs are derived from an individual with a diagnosed disease or disorder, or an individual who is an organ or bone marrow transplant recipient.

In one embodiment of any one of the population of HSCs or composition comprising a population of HSCs, the HSCs are derived from an individual who has newly been diagnosed with T1D.

In one embodiment of any one of the population of HSCs or composition comprising a population of HSCs, the HSCs are derived from an individual who has newly been detected to have self-autoantibodies associated with T1D, e.g., GAD65 autoantibody, and islet antigen 2 autoantibody.

In one embodiment of any one of the population of HSCs or composition comprising a population of HSCs, the diagnosed disease or disorder is an autoimmune disease or disorder.

In one embodiment of any one of the population of HSCs or composition comprising a population of HSCs, the autoimmune disease or disorder is T1D.

In one embodiment of any one of the population of HSCs or composition comprising a population of HSCs, the cells are ex vivo cultured before the introduction of the exogenous copy of a nucleic acid encoding a PD-L1, or after the introduction of the exogenous copy of a nucleic acid encoding a PD-L1, or both before and after the introduction of the exogenous copy of a nucleic acid encoding a PD-L1.

In one embodiment of any one of the population of HSCs or composition comprising a population of HSCs, the cells are cryopreserved prior to the introduction of the exogenous copy of a nucleic acid encoding a PD-L1, or after the introduction of the exogenous copy of a nucleic acid encoding a PD-L1, or both before and after the introduction of the exogenous copy of a nucleic acid encoding a PD-L1.

In one embodiment of any one of the population of HSCs or composition comprising a population of HSCs, the cells are cryopreserved prior to use, for example, use in the treatment of an autoimmune disease or for deliberate/intentional suppression of an immune response or the immune system in a subject.

In one embodiment of any one of the population of HSCs or composition comprising a population of HSCs, the population of modified HSCs are produced by a method comprising contacting a sample of HSCs with a vector carrying an exogenous copy of a nucleic acid encoding a PD-L1 to modify the HSCs to produce a population of modified HSCs cells that express PD-L1.

In one embodiment of any one of the population of HSCs or composition comprising a population of HSCs, the method further comprises ex vivo culturing to expand the resultant modified cells from the contacting with the vector.

In one embodiment of any one of the population of HSCs or composition comprising a population of HSCs, the method further comprises establishing the expression of PD-L1 on the modified HSCs.

In one embodiment of any one of the population of HSCs or composition comprising a population of HSCs, the method further comprises establishing that there is at least one fold increase in the number of PD-L1$^+$ expressing cells compared to non-modified cells.

In one embodiment of any one of the composition comprising a population of HSCs described, the composition further comprises at least an additional immunosuppression therapy agent or drug.

In one embodiment of any one of the composition comprising a population of HSCs described, the composition further comprises a pharmaceutically acceptable carrier. The carrier is preferable not cell or tissue culture media.

In one embodiment of any one of the composition comprising a population of HSCs described, the composition further comprises serum or plasma.

In one embodiment, provided herein is an ex vivo method of producing a population of modified, PD-L1$^+$ expressing HSCs, the method comprising contacting a sample of HSCs with a vector carrying an exogenous copy of a nucleic acid encoding a PD-L1 to modify the HSCs whereby the exogenous copy of a nucleic acid is introduced into the HSCs thereby producing a population of modified HSCs cells expressing PD-L1.

In one embodiment of any one of the ex vivo method described, the method further comprises ex vivo culturing of the resultant modified cells from the contacting with the vector carrying an exogenous copy of a nucleic acid encoding a PD-L1.

In one embodiment of any one of the ex vivo method described, the method further comprises establishing the expression of PD-L1 on the modified HSCs.

In one embodiment of any one of the ex vivo method described, the method further comprises comprises establishing that there is at least one fold increase in the number of PD-L1$^+$ expressing cells compared to non-modified cells.

In one embodiment of any one of the ex vivo method described, the sample of HSC is obtained from the bone marrow, umbilical cord, amniotic fluid, chorionic villi, cord blood, placental blood or peripheral blood.

In one embodiment of any one of the ex vivo method described, the sample of HSC is obtained from mobilized peripheral blood, e.g., mobilized by granulocyte colony stimulating factor (G-CSF).

In one embodiment of any one of the ex vivo method described, the sample of HSCs is obtained from a healthy individual.

In one embodiment of any one of the ex vivo method described, the sample of HSCs is obtained from an individual with a diagnosed disease or disorder.

In one embodiment of any one of the ex vivo method described, the diagnosed disease or disorder is an autoimmune disease or disorder.

In one embodiment of any one of the ex vivo method described, the autoimmune disease or disorder is T1D.

In one embodiment of any one of the ex vivo method described, the sample of HSCs is obtained from an individual who has newly been diagnosed with T1D.

In one embodiment of any one of the ex vivo method described, the sample of HSCs is obtained from an individual who has newly been detected to have self-autoantibodies associated with T1D, e.g., GAD65 autoantibody, and islet antigen 2 autoantibody.

In one embodiment of any one of the ex vivo method described, the vector is viral vector.

In one embodiment of any one of the ex vivo method described, the viral vector is a lentiviral vector, an avian virus vector or an adeno-associated virus.

In one embodiment of any one of the ex vivo method described, the nucleic acid is a cDNA.

In one embodiment of any one of the ex vivo method described, the nucleic acid is a genomic DNA.

In one embodiment of any one of the ex vivo method described, the nucleic acid is integrated into the genome of the cells.

In one embodiment, provided herein is a method of treating an autoimmune disorder or suppressing an immune response in a subject in need thereof, the method comprising administering to a subject a composition comprising the hematopoietic stem cells described herein.

In one embodiment, provided herein is a method of preventing or treating an autoimmune disorder or suppressing an immune response in a subject in need thereof, the method comprising providing a population of HSCs; ex vivo contacting the sample of HSCs with prostaglandin E2 ($PGE_2$) at 10 µM concentration for about 60 minutes at 37° C.; removing the $PGE_2$ after 60 minutes, thereby producing a population of PD-L1$^+$ expressing HSCs; transplanting the population of PD-L1$^+$ expressing HSCs into a recipient subject, thereby modulating the immune response in the recipient subject.

In one embodiment, provided herein is a method of delaying the onset of T1D in a subject in need thereof, the method comprising providing a population of HSCs; ex vivo contacting the sample of HSCs with prostaglandin E2 ($PGE_2$) at 10 µM concentration for about 60 minutes at 37° C.; removing the $PGE_2$ after 60 minutes, thereby producing a population of PD-L1$^+$ expressing HSCs; transplanting the population of PD-L1$^+$ expressing HSCs into a recipient subject, thereby modulating the immune response in the recipient subject. In one embodiment, the subject is at risk of developing T1D. In one embodiment, the subject is asymphomatic for T1D and is not hyperglycemia. For example, the subject's a blood sugar level is not higher than 11.1 mmol/l (200 mg/dl). In one embodiment, the subject is has recently been detected to have self-autoantibodies associated with T1D, e.g., ICA, IAA and 1A-2A.

In one embodiment, provided herein is a method of preventing or delaying an allogenic tissue/organ rejection in a subject in need thereof, the method comprising providing a population of HSCs; ex vivo contacting the sample of HSCs with prostaglandin E2 ($PGE_2$) at 10 µNI concentration for about 60 minutes at 37° C.; removing the $PGE_2$ after 60 minutes, thereby producing a population of PD-L1$^+$ expressing HSCs; transplanting the population of PD-L1$^+$ expressing HSCs into a recipient subject, thereby modulating the immune response in the recipient subject. In one embodiment, the subject is an organ or tissue transplant recipient.

In one embodiment, provided herein is a method of preventing or treating an autoimmune disorder or suppressing an immune response in a subject in need thereof, the method comprising providing a population of HSCs; ex vivo contacting the sample of HSCs with prostaglandin E2 ($PGE_2$) at 0.1 µM concentration for at least 24 hours at 37° C.; removing the $PGE_2$, thereby producing a population of PD-L1$^+$ expressing HSCs; transplanting the population of PD-L1$^+$ expressing HSCs into a recipient subject, thereby modulating the immune response in the recipient subject.

In one embodiment, provided herein is a method of delaying the onset of T1D in a subject in need thereof, the method comprising providing a population of HSCs; ex vivo contacting the sample of HSCs with prostaglandin E2 ($PGE_2$) at 0.1 µNI concentration for at least 24 hours at 37° C.; removing the $PGE_2$, thereby producing a population of PD-L1$^+$ expressing HSCs; transplanting the population of PD-L1$^+$ expressing HSCs into a recipient subject, thereby modulating the immune response in the recipient subject. In one embodiment, the subject is at risk of developing T1D. In one embodiment, the subject is asymphomatic for T1D and is not hyperglycemia. For example, the subject's a blood sugar level is not higher than 11.1 mmol/l (200 mg/dl). In one embodiment, the subject is has recently been detected to have self-autoantibodies associated with T1D, e.g., ICA, IAA and 1A-2A.

In one embodiment, provided herein is a method of preventing or delaying an allogenic tissue/organ rejection in a subject in need thereof, the method comprising providing a population of HSCs; ex vivo contacting the sample of HSCs with prostaglandin E2 ($PGE_2$) at 0.1 µM concentration for at least 24 hours at 37° C.; removing the $PGE_2$, thereby producing a population of PD-L1$^+$ expressing HSCs; transplanting the population of PD-L1$^+$ expressing HSCs into a recipient subject, thereby modulating the immune response in the recipient subject. In one embodiment, the subject is an organ or tissue transplant recipient.

In one embodiment, provided herein is a method of preventing or treating an autoimmune disorder or suppressing an immune response in a subject in need thereof, the method comprising: providing a population of HSCs; ex vivo contacting the sample of HSCs with a vector carrying an exogenous copy of a nucleic acid encoding a PD-L1; ex vivo culturing the resultant modified cells from the contacting; establishing the expression of PD-L1 on the modified HSCs, thereby producing a population of modified HSCs cells expressing PD-L1, transplanting said population of PD-L1$^+$ expressing HSCs into a recipient subject, thereby modulating the immune response in the recipient subject.

In one embodiment, provided herein is a method of delaying the onset of T1D in a subject in need thereof, the method comprising: providing a population of HSCs; ex vivo contacting the sample of HSCs with a vector carrying an exogenous copy of a nucleic acid encoding a PD-L1; ex vivo culturing the resultant modified cells from the contacting; establishing the expression of PD-L1 on the modified HSCs, thereby producing a population of modified HSCs cells expressing PD-L1, transplanting said population of PD-L1$^+$ expressing HSCs into a recipient subject, thereby modulating the immune response in the recipient subject.

In one embodiment, provided herein is a method of preventing or delaying an allogenic tissue/organ rejection in a subject in need thereof, the method comprising: providing a population of HSCs; ex vivo contacting the sample of HSCs with a vector carrying an exogenous copy of a nucleic acid encoding a PD-L1; ex vivo culturing the resultant modified cells from the contacting; establishing the expression of PD-L1 on the modified HSCs, thereby producing a population of modified HSCs cells expressing PD-L1, transplanting said population of PD-L1$^+$ expressing HSCs into a recipient subject, thereby modulating the immune response in the recipient subject.

In one embodiment of any one of the method described, the autoimmune disorder is T1D.

In one embodiment of any one of the method described, the population of HSCs provided is autologous to the recipient subject. In one embodiment, the subject is newly diagnosed with T1D. In another embodiment, the subject is newly been detected to have self-autoantibodies associated with T1D, e.g., GAD65 autoantibody, and islet antigen 2 autoantibody.

In one embodiment of any one of the method described, the population of HSCs provided is non-autologous and allogenic to the recipient subject.

In one embodiment of any one of the method described, the population of HSCs provided is non-autologous and xenogeneic to the recipient subject.

In one embodiment of any one of the method described, the population of HSCs provided is obtained from the bone marrow, umbilical cord, amniotic fluid, chorionic villi, cord blood, placental blood or peripheral blood.

In one embodiment of any one of the method described, the population of HSCs provided is obtained from mobilized peripheral blood.

In one embodiment of any one of the ex vivo method described, the population of HSCs provided is obtained from a healthy individual.

In one embodiment of any one of the ex vivo method described, the population of HSCs provided is obtained from an individual with a diagnosed disease or disorder.

In one embodiment of any one of the ex vivo method described, the diagnosed disease or disorder is an autoimmune disease or disorder.

In one embodiment of any one of the ex vivo method described, the autoimmune disease or disorder is T1D.

In one embodiment of any one of the ex vivo method described, the population of HSCs provided is obtained from an individual who has newly been diagnosed with T1D.

In one embodiment of any one of the ex vivo method described, the population of HSCs provided is obtained from an individual who has newly been detected to have self-autoantibodies associated with T1D, e.g., GAD65 autoantibody, and islet antigen 2 autoantibody.

In one embodiment of any one of the method described, the population of HSCs provided is at the minimum CD 34$^+$.

In one embodiment of any one of the method described, the population of HSCs provided is at the minimum CD 34$^+$ and Lin$^-$.

In another embodiment of any one of the method described, the population of HSCs provided is CD34$^+$, CD59$^+$, Thy1/CD90$^+$, CD38$^{lo/-}$, and C-kit/CD117$^+$.

In one embodiment of any one of the method described, the population of HSCs provided is CD34$^+$-selected HSCs. In another embodiment, the HSCs are negatively selected against CD38. That is, only CD38$^{lo/-}$ cells are selected. In another embodiment, the HSCs are selected for CD34$^+$ and CD38$^{lo/-}$.

In one embodiment of any one of the method described, the PGE$_2$ stimulated HSCs are also treated with steroids such as dexamethasome ex vivo, prior to use in implantation into the recipient.

In one embodiment of any one of the method described, prior to the transplantation into the recipient subject, the population of HSCs are cryopreserved after the removal of excess PGE$_2$ or cryopreserved after ex vivo culturing to expand the population of HSCs post-transfection with the vector carrying an exogenous copy of a nucleic acid encoding a PD-L1.

In one embodiment of any one of the method described, prior to the transplantation into the recipient subject, the population of HSCs are culture expanded ex vivo after the removal of excess PGE$_2$ or after transfection with a vector the vector carrying an exogenous copy of a nucleic acid encoding a PD-L1.

In one embodiment of any one of the method described, the method further comprising identifying a recipient subject having an autoimmune disease or disorder or an individual who is an organ or bone marrow transplant recipient.

In one embodiment of any one of the method described, the method further comprising selecting a recipient subject having an autoimmune disease or disorder or an individual who is an organ or bone marrow transplant recipient.

In one embodiment of any one of the method described, the method further comprising identifying a recipient subject in need of the suppression of an immune response or immune system or an individual who is an organ or bone marrow transplant recipient.

In one embodiment of any one of the method described, the method further comprising selecting a recipient subject in need of the suppression of an immune response or immune system. For example, an individual who is an organ or bone marrow transplant recipient.

In one embodiment of any one of the method described, the method further comprising identifying a subject at risk of developing T1D. For example, a subject who is newly been detected to have self-autoantibodies associated with T1D, e.g., GAD65 autoantibody, and islet antigen 2 autoantibody.

In one embodiment of the population of HSCs, the ex vivo method, the composition or the treatment method described herein, the PGE$_2$ that stimulates PD-L1 expression in the HSCs is 16,16-Dimethyl prostaglandin E$_2$ (dmPGE$_2$).

Definitions

As used herein, the term "nucleic acid" when used in reference to encoding a PD-L1 refers to refers to deoxyribonucleotides (DNA) or ribonucleotides (RNA) and polymers thereof ("polynucleotides") in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid molecule/polynucleotide also implicitly encompasses conservatively modified variants thereof (e.g. degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19: 5081 (1991); Ohtsuka et al., J. Biol. Chem. 260: 2605-2608 (1985); Rossolini et al., Mol. Cell. Probes 8: 91-98 (1994)). Nucleotides are indicated by their bases by the following standard abbreviations: adenine (A), cytosine (C), thymine (T), and guanine (G).

In some embodiments, as used herein, the term "genetically engineered," "genetically modified" or "modified" refers to the addition, deletion, or modification of the genetic material in a cell. In some embodiments, the terms, "genetically modified cells" and "modified cells," are used interchangeably. In other embodiments, "modified cells" refer to pharmacologically $PGE_2$-stimulated HSCs or pharmacologically $PGE_2$-modified HSCs that express PD-L1 compared to prior to the stimulation.

In one embodiment, the term "non-modified HSCs" refers to HSCs that do not carry exogenous copies of a nucleic acid encoding a PD-L1. In another embodiment, the term "non-modified HSCs" refers to HSCs that have not been ex vivo pharmacologically stimulated by $PGE_2$.

As used herein, the term "exogenous copy" in the context of a coding nucleic acid refers to an extra copy of the coding nucleic acid that is not the original copy of the gene found in the genome of the HSCs. The extra copy of the coding nucleic acid is typically introduced into the cells. For example, the extra copy is carried in a vector. The extra copy may be integrated into the genome of the cells.

As used herein, the term "coding" or "encoding" in the context of a nucleic acid encoding a PD-L1 means the nucleic acid contains instruction or information therein to specify the genetic code for a protein, e.g., the cell surface protein PD-L1. The instruction or information in a coding nucleic acid can be transcribe and translated to the encoded protein.

As used herein, the term "cDNA" refers to complementary DNA that is double-stranded DNA synthesized from a messenger RNA (mRNA) template in a reaction catalysed by the enzyme reverse transcriptase. The cDNA lacks introns.

As used herein, a genomic DNA encoding a PD-L1 means the copy of the gene as found in the genome of a cell. The genomic DNA encoding a PD-L1 would include introns and other regulatory sequences in addition to the coding exons.

As used herein, the term "integrated" when used in the context of the nucleic acid encoding a PD-L1 means that the nucleic acid is inserted into the genome or the genomic sequences of a cell. When integrated, the integrated nucleic acid is replicated and divided into the daughter dividing cells in the same manner as the original genome of the cell.

As used herein, the term "vector", when used in the context of carrying an exogenous copy of a nucleic acid encoding a PD-L1 vector, refers broadly to a nucleic acid construct designed for delivery an exogenous nucleic acid to a host cell or transfer between different host cells. In one embodiment, a vector can be viral or non-viral. In other embodiments, a vector refers to any plasmid, phagemid or virus encoding an exogenous nucleic acid. In other embodiments, the term is also be construed to include non-plasmid, non-phagemid and non-viral compounds which facilitate the transfer of nucleic acid into virions or cells, such as, for example, poly-lysine compounds and the like. The vector may be a viral vector that is suitable as a delivery vehicle for delivery of the nucleic acid, or mutant thereof, to a cell, or the vector may be a non-viral vector which is suitable for the same purpose. Examples of viral and non-viral vectors for delivery of DNA to cells and tissues are well known in the art and are described, for example, in Ma et al. (1997, Proc. Natl. Acad. Sci. U.S.A. 94: 12744-12746). Examples of viral vectors include, but are not limited to, a recombinant Vaccinia virus, a recombinant adenovirus, a recombinant retrovirus, a recombinant adeno-associated virus, a recombinant avian pox virus, and the like (Cranage et al., 1986, EMBO J. 5: 3057-3063; International Patent Application No. WO94/17810, published Aug. 18, 1994; International Patent Application No. WO94/23744, published Oct. 27, 1994). Examples of non-viral vectors include, but are not limited to, liposomes, polyamine derivatives of DNA, and the like.

As used herein, the term "viral vector" is used according to its art-recognized meaning. It refers to a nucleic acid vector construct that includes at least one element of viral origin and may be packaged into a viral vector particle. The vector may be utilized for the purpose of transferring DNA, RNA or other nucleic acids into cells either in vitro or in vivo. Numerous forms of viral vectors are known in the art.

As used herein, the term "lentivirus" refers to a group (or genus) of retroviruses that give rise to slowly developing disease. Viruses included within this group include HIV (human immunodeficiency virus; including HIV type 1, and HIV type 2), the etiologic agent of the human acquired immunodeficiency syndrome (AIDS); visna-maedi, which causes encephalitis (visna) or pneumonia (maedi) in sheep, the caprine arthritis-encephalitis virus, which causes immune deficiency, arthritis, and encephalopathy in goats; equine infectious anemia virus, which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which cause immune deficiency and encephalopathy in sub-human primates. Diseases caused by these viruses are characterized by a long incubation period and protracted course. Usually, the viruses latently infect monocytes and macrophages, from which they spread to other cells. HIV, FIV, and SIV also readily infect T lymphocytes, i.e., T-cells.

As used herein, the term "lentiviral vector" refers to a vector having a nucleic acid vector construct that includes at least one element of lentivirus origin. Lentiviral vectors of the disclosure include, but are not limited to, human immunodeficiency virus (e.g., HIV-1, HIV-2), feline immunodeficiency virus (FIV), simian immunodeficiency virus (SIV), bovine immunodeficiency virus (BIV), and equine infectious anemia virus (EIAV). These vectors can be constructed and engineered using art-recognized techniques to increase their safety for use in therapy and to include suitable expression elements and therapeutic genes.

As used herein, the term "autoimmune disease" or "autoimmune disease or disorder" herein is a disease or disorder arising from and directed against an individual's own tissues or a co-segregate or manifestation thereof or resulting condition therefrom.

Auto-immune related diseases and disorders arise from an overactive and/or abnormal immune response of the body against substances (autoantigens) and tissues normally present in the body, otherwise known as self or autologous substance. This dysregulated inflammatory reaction causes an exaggerated response by macrophages, granulocytes, and/or T-lymphocytes leading to abnormal tissue damage and cell death. Subsequent loss of function is associated with inflammatory tissue damage.

Autoantigens, as used herein, are endogenous proteins or fragments thereof that elicit this pathogenic immune response. Autoantigen can be any substance or a portion thereof normally found within a mammal that, in an autoimmune disease, becomes the primary (or a primary) target of attack by the immune system. The term also includes antigenic substances that induce conditions having the characteristics of an autoimmune disease when administered to mammals. Additionally, the term includes peptic subclasses consisting essentially of immunodominant epitopes or immunodominant epitope regions of autoantigens. Immunodominant epitopes or regions in induced autoimmune conditions are fragments of an autoantigen that can be used instead of the entire autoantigen to induce the disease. In humans afflicted with an autoimmune disease, immunodominant epitopes or regions are fragments of antigens specific to the tissue or organ under autoimmune attack and recognized by a substantial percentage (e.g. a majority though not necessarily an absolute majority) of autoimmune attack T-cells.

Autoantigens that are known to be associated with autoimmune disease include myelin proteins with demyelinating diseases, e.g. multiple sclerosis and experimental autoimmune myelitis; collagens and rheumatoid arthritis; insulin, proinsulin, glutamic acid decarboxylase 65 (GAD65); islet cell antigen (ICA512; ICA12) with insulin dependent diabetes.

A common feature in a number of autoimmune related diseases and inflammatory conditions is the involvement of pro-inflammatory CD4+ T cells. These T cells are responsible for the release of inflammatory, Th1 type cytokines. Cytokines characterized as Th1 type include interleukin 2 (IL-2), γ-interferon, TNFα and IL-12. Such pro-inflammatory cytokines act to stimulate the immune response, in many cases resulting in the destruction of autologous tissue. Cytokines associated with suppression of T cell response are the Th2 type, and include IL-10, IL-4 and TGF-β. It has been found that Th1 and Th2 type T cells may use the identical antigen receptor in response to an immunogen; in the former producing a stimulatory response and in the latter a suppressive response.

In one embodiment, as used herein, the term "hematopoietic stem cell" or "HSC" refers to a stem cell that give rise to all the blood cell types of the three hematopoietic lineages, erythroid, lymphoid, and myeloid. These cell types include the myeloid (monocytes and macrophages, neutrophils, basophils, eosinophils, erythrocytes, megakaryocytes/platelets, dendritic cells), and the lymphoid lineages (T-cells, B-cells, NK-cells). In one embodiment, the term "hematopoietic stem cell" or "HSC" refers to a stem cell that have the following cell surface markers: $CD34^+$, $CD59^+$, $Thy1/CD90^+$, $CD38^{lo/-}$, and $C-kit/CD117^+$. In one embodiment, the term "hematopoietic stem cell" or "HSC" refers to a stem cell that is at least $CD34^+$. In one embodiment, the term "hematopoietic stem cell" or "HSC" refers to a stem cell that is at least $CD38lo/^-$. In one embodiment, the term "hematopoietic stem cell" or "HSC" refers to a stem cell that is at least $CD34^+$ and $CD38^{lo/-}$. In one embodiment, the term "hematopoietic stem cell" or "HSC" refers to a stem cell that is at least $lin^-$. In one embodiment, the term "hematopoietic stem cell" or "HSC" refers to a stem cell that is at least $CD34^+$ and $lin^-$. In one embodiment, the term "hematopoietic stem cell" or "HSC" refers to a stem cell that is at least $CD34^+$, $CD38^{lo/-}$ and $lin^-$. In one embodiment, the term "hematopoietic stem cell" or "HSC" refers to a stem cell that is at least $CD34^+$ and $C-kit/CD117^+$. In one embodiment, the term "hematopoietic stem cell" or "HSC" refers to a stem cell that is at least $CD34^+$, $CD38^{lo/-}$ and $C-kit/CD117^+$. In another embodiment, as used herein, the term "hematopoietic stem cell" or "HSC" includes hematopoietic stem and progenitor cells (HSPC).

In one embodiment, as used herein, the term "a progenitor cell" refers to refer to an immature or undifferentiated cell that has the potential later on to mature (differentiate) into a specific cell type, for example, a blood cell, a skin cell, a bone cell, or a hair cells. A progenitor cell also can proliferate to make more progenitor cells that are similarly immature or undifferentiated.

Cells of the disclosure can be autologous/autogenic ("self") or non-autologous ("non-self," e.g., allogeneic, syngeneic or xenogeneic). "Autologous," as used herein, refers to cells from the same subject.

"Allogeneic," as used herein, refers to cells of the same species that differ genetically to the cell in comparison.

"Syngeneic," as used herein, refers to cells of a different subject that are genetically identical to the cell in comparison.

"Xenogeneic," as used herein, refers to cells of a different species to the cell in comparison. In preferred embodiments, the cells of the disclosure are allogeneic.

An "isolated cell" refers to a cell that has been obtained from an in vivo tissue or organ and is substantially free of extracellular matrix.

A "subject," as used herein, includes any animal that possess a hematopoietic system, an immune system and HSCs. In one embodiment, a subject includes any animal that exhibits symptoms of a disease, disorder, or condition of the immune system, e.g., autoimmune disease, that can be treated with the HSCs described herein, and methods contemplated herein. Suitable subjects (e.g., patients) include laboratory animals (such as mouse, rat, rabbit, or guinea pig), farm animals, and domestic animals or pets (such as a cat or dog). Non-human primates and, preferably, human patients, are included. Typical subjects include animals that exhibit aberrant amounts (lower or higher amounts than a "normal" or "healthy" subject) of one or more physiological activities that can be modulated by the HSCs described herein, and methods disclosed elsewhere herein. In another embodiment, the subject is a human.

In one embodiment, as used herein "treatment" or "treating," includes any beneficial or desirable effect on the symptoms or pathology of a disease or pathological condition, and may include even minimal reductions in one or more measurable markers of the disease or condition being treated. In another embodiment, treatment can involve optionally either the reduction or amelioration of symptoms of the disease or condition, or the delaying of the progression of the disease or condition. "Treatment" does not necessarily indicate complete eradication or cure of the disease or condition, or associated symptoms thereof.

As used herein, "self-autoantibodies associated with T1D" refer to the autoantibodies tha are markers of beta cell autoimmunity in type 1 diabetes: Islet Cell Antibodies (ICA, against cytoplasmic proteins in the beta cell), antibodies to Glutamic Acid Decarboxylase (GAD-65), Insulin Autoantibodies (IAA), and IA-2A, to protein tyrosine phosphatase.

As used herein, in one embodiment, the term "pharmaceutically acceptable" means approved by a regulatory agency of the Federal or a state government or listed in the U.S. Pharmacopeia or other generally recognized pharmacopeia for use in animals, and more particularly in humans. Specifically, it refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences, 18th Ed., Gennaro, ed. (Mack Publishing Co., 1990). The formulation should suit the mode of administration.

In one embodiment, "pharmaceutically acceptable carriers" exclude tissue culture medium. In another embodiment, "pharmaceutically acceptable carriers" include serum or plasma. The serum or plasma can be derived from human or the subject recipient.

The term "effective amount" means an amount of biologically active vector particles or $PGE_2$ concentration sufficient to provide successful transduction of cells with the exogenous nucleic acid or to provide successful stimulation of PD-L1 expression in the cell respectively.

As used herein, the terms "administering," refers to the placement of the HSCs described herein or the composition comprising the HSCs described herein into a recipient subject by a method or route which results in at least partial localization of the HSCs at a desired site, or results in the proliferation, engraftment and/or differentiation of the HSCs to PD-L1 expressing progeny cells. The HSCs or the composition comprising the HSCs can be administered by any appropriate route which results in an effective treatment in the subject.

As used herein, the term "comprising" or "comprises" is used in reference to methods, and respective component(s) thereof, that are essential to the disclosure, yet open to the inclusion of unspecified elements, whether essential or not. The use of "comprising" indicates inclusion rather than limitation.

BRIEF DESCRIPTION OF THE DRAWINGS

FIGS. 3D and 3E show that the human PD-L1 defect on HSCs can be overturned in vitro by pharmacologic approach. After 7 days of in vitro culture, an increase in the percentage of PD-L1$^+$ HSCs was evident.

FIG. 8A is a table summarizing the microarray analyses of Sca-1$^+$ Lineage$^-$c-kit$^+$ HSCs from bone marrow of NOD and B6 mice showing that genes were differentially expressed.

FIG. 8B is a Western Blot showing the reduced expression of PD-L1 in Sca-1$^+$Lineage$^-$c-kit$^+$ HSCs from bone marrow of NOD compared to normal B6 control mice.

FIG. 8C is a histogram summarizing the relative expression of PD-L1 in Sca-1$^+$Lineage$^-$c-kit$^+$ HSCs from bone marrow of NOD compared to normal B6 control mice, data obtained by Western blot analysis and quantitative measurements. Open histogram is NOD mice, closed histogram is C57BL/6 mice.

FIG. 8D is a a histogram summarizing the relative mRNA expression of PD-L1 in Sca-1$^+$Lineage$^-$ c-kit$^+$ HSCs from bone marrow of NOD compared to normal B6 control mice. Open histogram is NOD mice, closed histogram is C57BL/6 mice.

FIGS. 8E and 8F show the FACS dot plots and the histograms of PD-L1$^+$ KLS: Sca-1$^+$Lineage$^-$c-kit$^+$ cells from bone marrow of NOD compared to normal B6 control mice. Open histogram is NOD mice, closed histogram is C57BL/6 mice.

FIGS. 8G and 8H show the FACS dot plots and the histograms of PD-L1$^+$ CD41$^-$ CD48$^-$ CD150$^+$ cells from bone marrow of NOD compared to normal B6 control mice. Open histogram is NOD mice, closed histogram is C57BL/6 mice.

FIGS. 8I and 8K show the FACS dot plots and the histograms of PD-L1$^+$ KL: Lineage$^-$c-kit$^+$ cells from bone marrow of NOD compared to normal B6 control mice. Open histogram is NOD mice, closed histogram is C57BL/6 mice.

FIGS. 8J and 8L show the FACS dot plots and the histograms of PD-L1$^+$ CD244$^-$ CD48$^-$ CD150$^+$cells from bone marrow of NOD compared to normal B6 control mice. Open histogram is NOD mice, closed histogram is C57BL/6 mice.

FIG. 9A shows the flow cytometric analysis of PD-L1 expression on KL cells extracted from NOD mice prior to transduction with PD-L1 lentivirus, also known as wild type (WT) KL cells.

FIG. 9B shows the flow cytometric analysis of PD-L1 expression on KL cells from NOD mice after transduction with PD-L1 lentivirus, labeled as Tg cells.

FIG. 9C shows the histogram summarizing the increased in PD-L1 expression on KL cells from NOD mice after transduction with PD-L1 lentivirus.

FIG. 9D shows the histogram summarizing the flow cytometric analysis of INFγ production by CD4+ T cells extracted from NOD-BDC2.5 TCRtg mice stimulated by BDC2.5 peptides in the presence of DCs and upon coculture with KL cells and with PD-L1. Tg KL cells.

FIG. 9E shows the flow cytometric analysis of INFγ production by by CD4+ T cells extracted from NOD-BDC2.5 TCRtg mice stimulated by BDC2.5 peptides in the presence of DCs and upon coculture with KL cells and with PD-L1. Tg KL cells in the presence of PD-L1 blocking/neutralizing Ab.

FIG. 9F shows the histogram summarizing the flow cytometric analysis of INFγ production by CD4+ T cells extracted from NOD mice stimulated by soluble anti-CD$^3$/anti-CD28 upon coculture with KL cells and with PD-L1. Tg KL cells.

FIG. 9G shows the flow cytometric analysis of INFγ production by CD4+ T cells extracted from NOD mice stimulated by soluble anti-CD$^3$/anti-CD28 upon coculture with KL cells and with PD-L1. Tg KL cells in the presence of PD-L1 blocking/neutralizing Ab.

(FIG. 9H) Untreated group used as control.

FIGS. 10A-10F demonstrated that the PD-L1 defect in human HSCs from T1D patients as compared to healthy controls human subjects (HC).

FIGS. 10A-10B are representative flow cytometric analysis showing PD-L1 expression in selected CD34+ HSCs from healthy controls (HC) (FIG. 10A) and from type 1 diabetic individuals (T1D) (FIG. 10B).

FIG. 10C shows the bar graph related to the flow cytometric analysis in FIGS. 10A-10B, illustrating the defect in PD-L1 expression in T1D.

FIG. 10D is a representative Western-blot analysis showing reduced PD-L1 expression in CD34+ HSCs of T1D individual compared to HC.

FIG. 10E is a histogram summarizing the Western-blot analysis showing reduced PD-L1 expression in CD34+ HSCs of T1D individual compared to HC.

FIG. 10F is a histogram summarizing the RT-PCR data for PD-L1 expression in CD34+ HSCs of T1D individual compared to HC.

DETAILED DESCRIPTION

Figure 1:
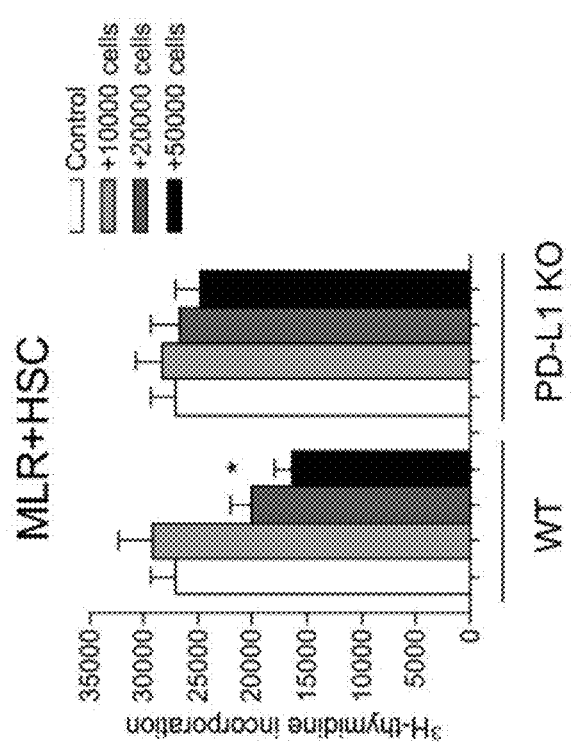
FIG. 1 shows that PD-L1 genetic deletion abrogates HSC immunomodulatory properties in vitro.

Unless otherwise explained, all technical and scientific terms used herein have the same meaning as commonly understood by one of ordinary skill in the art to which this disclosure belongs. It should be understood that this disclosure is not limited to the particular methodology, protocols, and reagents, etc., described herein and as such can vary. The terminology used herein is for the purpose of describing particular embodiments only, and is not intended to limit the scope of the present disclosure, which is defined solely by the claims.

Definitions of common terms in molecular biology can be found in The Merck Manual of Diagnosis and Therapy, 19th Edition, published by Merck Sharp & Dohme Corp., 2011 (ISBN 978-0-911910-19-3), (2015 digital online edition at merckmanuals.com), Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties. Further, unless otherwise required by context, singular terms shall include pluralities and plural terms shall include the singular.

Unless otherwise stated, the present disclosure was performed using standard procedures known to one skilled in the art, for example, in Michael R. Green and Joseph Sambrook, Molecular Cloning: A Laboratory Manual, Cold Spring Harbor Laboratory Press, Cold Spring Harbor, N.Y., USA (2012); Davis et al., Basic Methods in Molecular Biology, Elsevier Science Publishing, Inc., New York, USA (1986); Current Protocols in Molecular Biology (CPMB) (Fred M. Ausubel, et al. ed., John Wiley and Sons, Inc.), Current Protocols in Immunology (CPI) (John E. Coligan, et. al., ed. John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998), Methods in Molecular biology, Vol. 180, Transgenesis Techniques by Alan R. Clark editor, second edition, 2002, Humana Press, and Methods in Molecular Biology, Vo. 203, 2003, Transgenic Mouse, edited by Marten H. Hofker and Jan van Deursen, which are all herein incorporated by reference in their entireties.

It should be understood that this disclosure is not limited to the particular methodology, protocols, and reagents, etc., described herein and as such may vary. The terminology used herein is for the purpose of describing particular embodiments only, and is not intended to limit the scope of the present disclosure, which is defined solely by the claims.

Other than in the operating examples, or where otherwise indicated, all numbers expressing quantities of ingredients or reaction conditions used herein should be understood as modified in all instances by the term "about." The term "about" when used in connection with percentages will mean ±1%.

All patents and publications identified are expressly incorporated herein by reference for the purpose of describing and disclosing, for example, the methodologies described in such publications that might be used in connection with the present disclosure. These publications are provided solely for their disclosure prior to the filing date of the present application. Nothing in this regard should be construed as an admission that the inventors are not entitled to antedate such disclosure by virtue of prior disclosures or for any other reason. All statements as to the date or representation as to the contents of these documents is based on the information available to the applicants and does not constitute any admission as to the correctness of the dates or contents of these documents.

The present disclosure relates to modified hematopoietic stem cells (HSCs), compositions comprising modified HSCs, methods of using these modified HSCs for treating autoimmune diseases and disorders and for modulating the immune system. The modified HSCs express the programmed cell death-1 receptor ligand (PD-L1) if the cells did not express PD-L1 prior to the modification or the modified HSCs now express more PD-L1 compared to prior to the modification. The modification is by tranducing an exogenous copy of a nucleic acid encoding PD-L1 to facilitate PD-L1 protein expression in the transduced cell or by pharmacological re-programming of the HSCs with stimulation by $PGE_2$.

The disclosure described herein, in a preferred embodiment, does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

In some embodiments, embodiments of the present disclosure are based on the discovery that increasing PD-L1 expression in the HSCs of patients with Type 1 diabetes (T1D) can alleviate the deficiencies in the patients' immunoregulation. NOD mice and human T1D patients have reduced number of PD-L1 expressing HSCs and the HSCs express lower amounts of PD-L1. The decrease PD-L1 contribute to defects in the mice and patients' ability to immunoregulation. Externally supplementing this PD-L1 deficiency help recorrect this immunoregulation defect by promoting immune tolerance.

Despite considerable effort to halt or delay the destruction of beta-cells in T1D, success remains elusive. Stem cells-based therapy using mesenchymal stem cells and autologous hematopoietic stem cell transplantation (AHSCT) yield only short-term insulin-independence in NOD mice and T1D humans, and for only a select population of afflicted with the disease. None of the stem cell-based therapies have not been applicable to pediatric patients. Moreover, certain stem cell based therapies present potential oncogenic concerns, especially for pediatric patients.

Therefore, the problem to solve here is to provide a therapy that is applicable to a larger population of T1D patients, both adults and pediatric patients, and a therapy that allows the patients to be long term insulin-independent.

Previously, preclinical studies on the use of HSCs in NOD mice are lacking and primarily employ allogeneic HSCs. When allogeneic HSCs from β-gal transgenic donors were transplanted into NOD mice, diabetes onset was successfully preventing in all treated mice, but reversal was obtained in only 1 out of 50 mice despite full hematopoietic engraftment. If a human is at high risk for developing T1D, perhaps administering the PD-L1$^+$ cells can delay the onset of the disease too. The inventors demonstrated that HSC immunological properties may be linked to the expression of the immunomodulatory molecule PD-L1 (also known as CD274 or B7-H1). PD-L1 is the ligand of the inhibitory receptor programmed death 1 receptor (PD-1), which is expressed primarily on activated T cells. Crosslinking between PD-L1 and PD-1 inhibits T cells activation and favor their exhaustion/apoptosis. PD-1 knockout mice develop accelerated diabetes, and PD-1/PD-L1 signaling activates an inhibitory signal inducing T cell anergy.

The inventors found that there are fewer numbers of CD34$^+$ HSCs that express the PD-L1 in patients with T1D compared to healthy humans. This discovery that was obtained by immunoflowcytometry was further confirmed by RT-PCR. There is about 3% PD-L1$^+$/CD34$^+$ HSCs for human patients with T1D compared to 14.5% PD-L1$^+$/CD34$^+$ HSCs for healthy humans. PD-L1 is an important immunoregulator molecule in the immune system.

Furthermore, the inventors found that the HSCs from T1D patients were defective in their immunoregulatory properties. When tested in an anti-CD3/CD28 ELISPOT immunoassay, the HSCs from these patients affected by T1D were less capable of suppressing an immune response.

Therefore, increasing or stimulating PD-L1 expression in HSCs derived from patients affected by T1D or other autoimmune disorders, and/or providing PD-L1 expressing HSCs to these individuals represent useful therapeutic strategies in treating autoimmune diseases and disorders, and for modulating the immune system. The inventors have discovered that ex vivo incubating the HSCs derived from T1D patients with prostaglandin E2 ($PGE_2$) stimulates expression of PD-L1 in the HSCs. In addition, transfecting an exogenous nucleic acid that codes for PD-L1 into HSCs promotes the expression of PD-L1 in the transfected/transduced HSCs.

PD-L1+ Expressing Hematopoietic Stem Cells (HSCs) and Compositions Thereof

Accordingly, in one embodiment, provided herein is an ex vivo method of producing a population of modified, PD-L1+ expressing HSCs where the modified HSC cells carry an exogenous copy of a nucleic acid encoding a programmed cell death-1 receptor ligand (PD-L1), the method comprising contacting a sample of HSCs with a vector carrying an exogenous copy of a nucleic acid encoding a PD-L1 to modify the HSCs, whereby the exogenous copy of a nucleic acid is introduced into the HSCs, thereby producing a population of modified HSCs cells expressing PD-L1. In one embodiment, the method further comprises establishing the expression of PD-L1 on the resultant modified HSCs. In another embodiment, the method further comprises ex vivo culturing the resultant modified cells after contact with the vector and/or ex vivo culturing the resultant modified cells after establishing the expression of PD-L1 on the resultant modified HSCs. The culturing expands the number of modified cells available for therapy. In one embodiment, the sample of HSCs can be culture expanded prior to contacting with the vector described.

In one embodiment, provided herein is an ex vivo method of producing a population of modified, PD-L1+ expressing HSCs where the modified HSC cells carry an exogenous copy of a nucleic acid encoding a PD-L1, the method comprising (a) contacting a sample of HSCs with a vector carrying an exogenous copy of a nucleic acid encoding a PD-L1 to modify the HSCs whereby the exogenous copy of a nucleic acid is introduced into the HSCs; and (b) establishing the expression of PD-L1 on the resultant modified HSCs, thereby producing a population of modified HSCs cells expressing PD-L1. In one embodiment, the method further comprises ex vivo culturing the resultant modified cells after contact with the vector and/or ex vivo culturing the resultant modified cells after establishing the expression of PD-L1 on the resultant modified HSCs. The culturing expands the number of modified cells available for therapy. In one embodiment, the sample of HSCs can be culture expanded prior to contacting with the vector described.

In one embodiment, provided herein is an ex vivo method of producing a population of modified, PD-L1+ expressing HSCs where the modified HSC cells carry an exogenous copy of a nucleic acid encoding a PD-L1, the method comprising (a) contacting a sample of HSCs with a vector carrying an exogenous copy of a nucleic acid encoding a PD-L1 to modify the HSCs whereby the exogenous copy of a nucleic acid is introduced into the HSCs; (b) ex vivo culturing the resultant modified cells from the contacting with the vector; and (c) establishing the expression of PD-L1 on the resultant modified HSCs, thereby producing a population of modified HSCs cells expressing PD-L1. The culturing expands the number of modified cells available for therapy. In one embodiment, the sample of HSCs can be culture expanded prior to contacting with the vector described.

In one embodiment, provided herein is a population of modified HSCs where the modified HSCs carry an exogenous copy of a nucleic acid encoding a PD-L1. The modified HSCs express more PD-L1 compared to non-modified cells not carrying an an exogenous copy of a nucleic acid encoding a PD-L1.

In one embodiment, provided herein is a population of modified HSCs, wherein the cells are produced by a method comprising contacting a sample of HSCs with a vector carrying an exogenous copy of a nucleic acid encoding a PD-L1 to modify the HSCs whereby the exogenous copy of a nucleic acid is introduced into the HSCs, thereby producing a population of modified HSCs cells expressing PD-L1. In one embodiment, the sample of HSCs comprises non-modified HSCs. In one embodiment, non-modified HSCs do not carry exogenous copies of a nucleic acid encoding a PD-L1. In one embodiment, the method further comprises establishing the expression of PD-L1 on the resultant modified HSCs. In another embodiment, the method further comprises ex vivo culturing the resultant modified cells after contact with the vector and/or ex vivo culturing the resultant modified cells after establishing the expression of PD-L1 on the resultant modified HSCs. The culturing expands the number of modified cells available for therapy. In one embodiment, the sample of HSCs can be culture expanded prior to contacting with the vector described.

In one embodiment, provided herein is a population of modified HSCs, wherein the cells are produced by a method comprising (a) contacting a sample of HSCs with a vector carrying an exogenous copy of a nucleic acid encoding a PD-L1 to modify the HSCs whereby the exogenous copy of a nucleic acid is introduced into the HSCs; and (b) establishing the expression of PD-L1 on the modified HSCs, thereby producing a population of modified HSCs cells expressing PD-L1. In one embodiment, the method further comprises ex vivo culturing the resultant modified cells after contact with the vector and/or ex vivo culturing the resultant modified cells after establishing the expression of PD-L1 on the resultant modified HSCs. The culturing expands the number of modified cells available for therapy. In one embodiment, the sample of HSCs can be culture expanded prior to contacting with the vector described.

In one embodiment, provided herein is a population of modified HSCs, wherein the cells are produced by a method comprising (a) contacting a sample of HSCs with a vector carrying an exogenous copy of a nucleic acid encoding a PD-L1 to modify the HSCs whereby the exogenous copy of a nucleic acid is introduced into the HSCs; (b) ex vivo culturing the resultant modified cells from the contacting; and (c) establishing the expression of PD-L1 on the modified HSCs, thereby producing a population of modified HSCs cells expressing PD-L1. The culturing expands or increases the number of modified cells available for therapy. In one embodiment, the sample of HSCs can be culture expanded prior to contacting with the vector described.

In one embodiment, the modified HSCs are engineered modified cells, engineered to carrying an exogenous copy of a nucleic acid encoding a PD-L1 in the cell. These engineered HSCs express PD-L1 compared HSCs not carrying an an exogenous copy of a nucleic acid encoding a PD-L1. In one embodiment, these engineered HSCs express more PD-L1 compared HSCs not carrying an an exogenous copy of a nucleic acid encoding a PD-L1.

In another embodiment, provided herein is an ex vivo method of stimulating the expression of PD-L1 in a population of HSCs, the method comprising (a) contacting a sample of HSCs with prostaglandin E2 ($PGE_2$) at 10 μM concentration for about 60 min at 37° C.; (b) washing the contacted cells to remove excess $PGE_2$, and (c) establishing the expression of PD-L1 on the $PGE_2$-stimulated HSCs, thereby producing a population of $PGE_2$-stimulated HSCs cells expressing PD-L1.

In one embodiment, the $PGE_2$-stimulated HSC has increased PD-L1 expression compared to non-$PGE_2$-stimulated HSC. In one embodiment, the $PGE_2$-stimulated HSC has at least 1% increased PD-L1 expression compared to non-$PGE_2$-stimulated HSC. In other embodiments, the $PGE_2$-stimulated HSC has at least 2%, at least 3%, at least 5%, at least 8%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 1-fold, at least 2-fold, at least 5-fold, at least 10 fold, at least 100 fold higher, at least 1000-fold higher, or more increased PD-L1 expression compared to non-$PGE_2$-stimulated HSC.

In another embodiment, provided herein is an ex vivo method of stimulating the expression of PD-L1 in a population of HSCs, the method comprising (a) contacting a sample of HSCs with prostaglandin E2 ($PGE_2$) at 0.1 μM concentration for at least 24 hrs at 37° C.; (b) washing the contacted cells to remove excess $PGE_2$, and (c) establishing the expression of PD-L1 on the $PGE_2$-stimulated HSCs, thereby producing a population of $PGE_2$-stimulated HSCs cells expressing PD-L1.

In another embodiment, provided herein is an ex vivo method of stimulating the expression of PD-L1 in a population of HSCs, the method comprising contacting a sample of HSCs with prostaglandin E2 ($PGE_2$) at 0.1 μM concentration for at least 24 hrs at 37° C., thereby producing a population of $PGE_2$-stimulated HSCs cells expressing PD-L1.

In another embodiment, provided herein is an ex vivo method of stimulating the expression of PD-L1 in a population of HSCs, the method comprising contacting a sample of HSCs with prostaglandin E2 (PGE$_2$) at 10 µM concentration for about 60 min at 37° C., thereby producing a population of PGE$_2$-stimulated HSCs cells expressing PD-L1.

In one embodiment of the above described methods, the method further comprises washing the contacted cells to remove excess PGE$_2$. In one embodiment, the method further comprises establishing the expression of PD-L1 on the PGE$_2$-stimulated HSCs. In another embodiment, the method further comprises ex vivo culturing of the PGE$_2$-stimulated HSCs after contact with PGE$_2$ and/or ex vivo culturing of the PGE$_2$-stimulated HSCs after establishing the expression of PD-L1 on the PGE$_2$-stimulated HSCs. The culturing expands the number of modified cells available for therapy. In one embodiment, the sample of HSCs can be culture expanded prior to contacting with PGE$_2$.

In another embodiment, provided herein is an ex vivo method of stimulating the expression of PD-L1 in a population of HSCs, the method comprising (a) contacting a sample of HSCs with prostaglandin E2 (PGE$_2$) at 10 µM concentration for about 60 min at 37° C., and (b) establishing the expression of PD-L1 on the PGE$_2$-stimulated HSCs, thereby producing a population of PGE$_2$-stimulated HSCs cells expressing PD-L1 thereby producing a population of PGE$_2$-stimulated HSCs cells expressing PD-L1. The culturing expands the number of modified cells available for therapy. In one embodiment, the sample of HSCs can be culture expanded prior to contacting with PGE$_2$.

In another embodiment, provided herein is an ex vivo method of stimulating the expression of PD-L1 in a population of HSCs, the method comprising (a) contacting a sample of HSCs with prostaglandin E2 (PGE$_2$) at 0.1 µM concentration for at least 24 hrs at 37° C., and (b) establishing the expression of PD-L1 on the PGE$_2$-stimulated HSCs, thereby producing a population of PGE$_2$-stimulated HSCs cells expressing PD-L1 thereby producing a population of PGE$_2$-stimulated HSCs cells expressing PD-L1.

In another embodiment of the above described methods, the method further comprises ex vivo culturing of the PGE$_2$-stimulated HSCs after contact with PGE$_2$ and/or ex vivo culturing of the PGE$_2$-stimulated HSCs after establishing the expression of PD-L1 on the PGE$_2$-stimulated HSCs. The culturing expands the number of modified cells available for therapy. In one embodiment, the sample of HSCs can be culture expanded prior to contacting with PGE$_2$.

In one embodiment, provided herein is a population of PD-L1$^+$ expressing HSCs wherein the cells are produced by a method comprising (a) contacting a sample of HSCs with PGE$_2$ at 10 µM concentration for about 60 min at 37° C.; (b) washing the contacted cells to remove excess PGE$_2$, and (c) establishing the expression of PD-L1 on the contacted HSCs, thereby producing a population of HSCs cells expressing PD-L1.

In one embodiment, provided herein is a population of PD-L1$^+$ expressing HSCs wherein the cells are produced by a method comprising (a) contacting a sample of HSCs with PGE$_2$ at 0.1 µM concentration for at least 24 hrs at 37° C.; (b) washing the contacted cells to remove excess PGE$_2$, and (c) establishing the expression of PD-L1 on the contacted HSCs, thereby producing a population of HSCs cells expressing PD-L1.

In another embodiment of the above described methods, the method further comprises ex vivo culturing of the PGE$_2$-stimulated HSCs after contact with PGE$_2$ and/or ex vivo culturing of the PGE$_2$-stimulated HSCs after establishing the expression of PD-L1 on the PGE$_2$-stimulated HSCs.

In one embodiment, provided herein is a population of PD-L1$^+$ expressing HSCs where the cells have been stimulated to increase the expression of endogenous PD-L1 by an ex vivo or in vivo or in vitro contact with PGE$_2$.

In one embodiment, provided herein is a population of modified HSCs where the modified HSCs express more PD-L1 compared to non-modified cells that have not been stimulated or contacted with PGE$_2$.

In one embodiment, provided herein is a population of PD-L1$^+$ expressing HSCs wherein the cells are produced by a method comprising contacting a sample of HSCs with PGE$_2$ at 10 µM concentration for about 60 min at 37° C., thereby producing a population of HSCs cells expressing PD-L1.

In one embodiment, provided herein is a population of PD-L1$^+$ expressing HSCs wherein the cells are produced by a method comprising contacting a sample of HSCs with PGE$_2$ at 0.1 µM concentration for at least 24 hrs at 37° C., thereby producing a population of HSCs cells expressing PD-L1.

In one embodiment of the above described methods or population of PD-L1$^+$ expressing HSCs, the method further comprises washing the contacted cells to remove excess PGE$_2$. In one embodiment, the method further comprises establishing the expression of PD-L1 on the PGE$_2$-stimulated HSCs. In another embodiment, the method further comprises ex vivo culturing of the PGE$_2$-stimulated HSCs after contact with PGE$_2$ and/or ex vivo culturing of the PGE$_2$-stimulated HSCs after establishing the expression of PD-L1 on the PGE$_2$-stimulated HSCs.

In one embodiment, provided herein is a population of PD-L1+ expressing HSCs wherein the cells are produced by a method comprising (a) contacting a sample of HSCs with prostaglandin E2 (PGE$_2$) at 10 µM concentration for about 60 min at 37° C., and (b) establishing the expression of PD-L1 on the PGE$_2$-stimulated HSCs, thereby producing a population of PGE$_2$-stimulated HSCs cells expressing PD-L1 thereby producing a population of PGE$_2$-stimulated HSCs cells expressing PD-L1.

In one embodiment, provided herein is a population of PD-L1+ expressing HSCs wherein the cells are produced by a method comprising (a) contacting a sample of HSCs with prostaglandin E2 (PGE$_2$) at 0.1 µM concentration for at least 24 hrs 37° C., and (b) establishing the expression of PD-L1 on the PGE$_2$-stimulated HSCs, thereby producing a population of PGE$_2$-stimulated HSCs cells expressing PD-L1 thereby producing a population of PGE$_2$-stimulated HSCs cells expressing PD-L1.

In some embodiment of the above described methods or population of PD-L1$^+$ expressing HSCs, the HSCs are also contacted with a steroid such as dexamethasone. In some embodiments, the HSCs are ex vivo contacted with both PGE$_2$ and a steroid such as dexamethasone, ie., co-stimulated simultaneously with both PGE$_2$ and dexamethasone. For example, dexamethasone at 0.1 µM-100 µM, 0.1 µM, 0.5 µM, 1 µM, 5 µM, 10 µM, 20 µM, 30 µM, 40 µM, 50 µM, 60 µM, 70 µM, 80 µM, 90 µM or 100 µM.

In another embodiment of the above described methods or populations of PD-L1$^+$ expressing HSCs, the method further comprises ex vivo culturing of the PGE$_2$-stimulated HSCs after contact with PGE$_2$ and/or ex vivo culturing of the PGE$_2$-stimulated HSCs after establishing the expression of PD-L1 on the PGE$_2$-stimulated HSCs.

In one embodiment of the described methods or populations of PD-L1$^+$ expressing HSCs herein, the sample of HSCs is cultured ex vivo in the absence of $PGE_2$ before the addition/contact of $PGE_2$. The ex vivo culturing expands or increases the number of starting HSCs available for contact and stimulation with $PGE_2$.

In one embodiment of the described methods or populations of PD-L1$^+$ expressing HSCs herein, the ex vivo culturing in the absence of $PGE_2$ occurs for at least 48 hrs prior to the first/initial addition or contact with $PGE_2$. The ex vivo culturing expands or increases the number of starting HSCs available for contact and stimulation with $PGE_2$.

In one embodiment of the described methods or populations of PD-L1$^+$ expressing HSCs herein, the HSCs are in contact with $PGE_2$ in culture for at least 24 hrs. In other embodiments, the HSCs are in contact with $PGE_2$ in culture for at least 36 hrs, at least 48 hrs, at least 60 hrs, at least 72 hrs, at least 84 hrs, at least 96 hrs, at least 108 hrs, at least 120 hrs, at least 132 hrs, at least 144 hrs, at least 156 hrs, at least 168 hrs, at least 196 hrs and all intervening time in hours between 24-196 hrs.

In another embodiment, the HSCs are in contact with $PGE_2$ in culture for up to eight days. In other embodiments, the HSCs are in contact with $PGE_2$ in culture for up to three days, for up to four days, for up to five days, for up to six days and for up to seven days.

In other embodiments, the HSCs are in contact with $PGE_2$ in culture for about 24 hrs, about 36 hrs, about 48 hrs, about 60 hrs, about 72 hrs, about 84 hrs, about 96 hrs, about 108 hrs, about 120 hrs, about 132 hrs, about 144 hrs, about 156 hrs, about 168 hrs, about 196 hrs and all intervening time in hours between 24-196 hrs.

In one embodiment, provided herein is a composition comprising a population of modified HSCs described herein, wherein the modified HSCs express PD-L1$^+$. For example, the modified HSCs carry an exogenous copy of a nucleic acid encoding a PD-L1. In one embodiment, the composition further comprises a pharmaceutically acceptable carrier. In one embodiment, the pharmaceutically acceptable carrier does not include tissue culture media.

In one embodiment, provided herein is a pharmaceutical composition comprising a population of modified HSCs described herein and a pharmaceutically acceptable carrier.

In one embodiment, provided herein is a composition comprising a population of PD-L1$^+$ expressing HSCs described herein wherein the HSCs are modified HSCs carrying an exogenous copy of a nucleic acid encoding a PD-L1 or the HSCs are ex vivo stimulated to increase the expression of endogenous PD-L1 by an ex vivo contact with $PGE_2$. In one embodiment, the composition further comprises a pharmaceutically acceptable carrier. In one embodiment, the pharmaceutically acceptable carrier does not include tissue culture media.

In one embodiment, provided herein is a composition comprising a population of modified HSCs described herein for use in conjunction with a transplantation procedure, or for use with the treatment of an autoimmune disease or disorder, or for use in reducing or modulating an immune response, wherein the modified HSCs carry an exogenous copy of a nucleic acid encoding a PD-L1 and express PD-L1. In one embodiment, the composition further comprises a pharmaceutically acceptable carrier. In one embodiment, the pharmaceutically acceptable carrier does not include tissue culture media.

In one embodiment, provided herein is a composition comprising a population of PD-L1$^+$ expressing HSCs described herein for use in conjunction with a transplantation procedure, or for use with the treatment of an autoimmune disease or disorder, or for use in reducing or modulating an immune response, wherein the HSCs are modified HSCs carrying an exogenous copy of a nucleic acid encoding a PD-L1 or the HSCs are ex vivo stimulated to increase the expression of endogenous PD-L1 by an ex vivo contact with $PGE_2$. In one embodiment, the composition further comprises a pharmaceutically acceptable carrier. In one embodiment, the pharmaceutically acceptable carrier does not include tissue culture media.

In one embodiment, provided herein is a composition comprising a population of modified HSCs described herein for manufacture of a medicament for use in conjunction with a transplantation procedure, or for use with the treatment of an autoimmune disease or disorder, or for use in reducing or modulating an immune response, wherein the modified HSCs carry an exogenous copy of a nucleic acid encoding a PD-L1 and express PD-L1. In one embodiment, the composition further comprises a pharmaceutically acceptable carrier. In one embodiment, the pharmaceutically acceptable carrier does not include tissue culture media.

In one embodiment, provided herein is a composition comprising a population of PD-L1$^+$ expressing HSCs described herein for manufacture of a medicament for use in conjunction with a transplantation procedure, or for use with the treatment of an autoimmune disease or disorder, or for use in reducing or modulating an immune response, wherein the HSCs are modified HSCs carrying an exogenous copy of a nucleic acid encoding a PD-L1 or the HSCs are ex vivo stimulated to increase the expression of endogenous PD-L1 by an ex vivo contact with $PGE_2$. In one embodiment, the composition further comprises a pharmaceutically acceptable carrier. In one embodiment, the pharmaceutically acceptable carrier does not include tissue culture media.

In one embodiment of the population of modified HSCs, the ex vivo method, or the composition described herein, modified HSCs or $PGE_2$-contacted HSCs are further analyzed to establish the expression of PD-L1 on the respective HSCs. Methods of determining PD-L1 expression are known in the art, for example, by using immunoflowcytometry, fluorescence-activated cell sorting (FACS) or any immunoassays known in the art, and by RT-PCR.

In one embodiment of the population of modified HSCs, the ex vivo method, or the composition described herein, the modified HSCs are expressing PD-L1. In one embodiment, there is at least one fold increase in the number of PD-L1$^+$ expressing cells compared to control HSCs that were not contacted with the vector and are non-modified HSCs that is not carrying an exogenous copy of a nucleic acid encoding a PD-L1. In one embodiment, there is up to ten fold increase in the number of PD-L1$^+$ expressing cells compared to control HSCs that were not contacted with the vector and are non-modified HSCs, that is not carrying an exogenous copy of a nucleic acid encoding a PD-L1.

In one embodiment, the modified HSCs express increased amount of PD-L1. In one embodiment, there is at least one fold increase in the amount of PD-L1$^+$ expressed compared to control HSCs which are HSCs that were not contacted with the vector and are non-modified HSCs that is not carrying an exogenous copy of a nucleic acid encoding a PD-L1. In one embodiment, there is up to ten fold increase in the amount of PD-L1$^+$ expressed compared to control HSCs that were not contacted with the vector and are non-modified HSCs that is not carrying an exogenous copy of a nucleic acid encoding a PD-L1.

In one embodiment of the population of PD-L1$^+$ expressing HSCs, the ex vivo method, or the composition described herein, the PD-L1$^+$ expressing HSCs express increased amount of PD-L1. In one embodiment, there is at least one fold increase in the number of PD-L1+ expressing cells compared to control HSCs which are non-PGE$_2$ incubated and stimulated HSCs. In one embodiment, there is up to ten fold increase in the number of PD-L1+ expressing cells compared to control HSCs that are non-PGE$_2$ contacted/ incubated and stimulated HSCs.

In one embodiment, the modified HSCs exhibit an increase expression of PD-L1 over control, non-modified HSCs.

In other embodiments, the increase in the number of PD-L1+ expressing cells or the increase in the amount of PD-L1 expressed is at least 1% higher, at least 3% higher, at least 5% higher, at least 8% higher, at least 10% higher, at least 20% higher, at least 30% higher, at least 40% higher, at least 50% higher, at least 60% higher, at least 70% higher, at least 80% higher, at least 90% higher, at least 1-fold higher, at least 2-fold higher, at least 5-fold higher, at least 10 fold higher, at least 100 fold higher, at least 1000-fold higher, or more than a comparable control non-modified HSCs or non-PGE$_2$ stimulated cells.

Programmed cell death protein 1, also known as PD-1 and cluster of differentiation 279 (CD279), is a receptor protein that in humans is encoded by the PDCD1 gene. PD-1 is a cell surface receptor that belongs to the immunoglobulin superfamily and is expressed on activated T cells and pro-B cells. PD-1 binds two ligands, PD-L1 (also known as B7 homolog 1 (B7-H1) or cluster of differentiation 274 (CD 274)) and PD-L2. The two ligands of PD-1, PD-L1 and PD-L2, are members of the B7 family.

PD-1 and its ligands play an important role in down regulating the immune system by preventing the activation of T-cells. PD-L1/PD-1 interaction deactivates T cell's cytotoxic activity and leads to the inhibition of immune system. This in turn reduces autoimmunity and promotes self-tolerance. The inhibitory effect of PD-1 is accomplished through a dual mechanism of promoting apoptosis (programmed cell death) in antigen specific T-cells in lymph nodes while simultaneously reducing apoptosis in regulatory T cells (suppressor T cells).

PD-L1, one of the ligand of the receptor PD-1, is a 40 kDa type 1 transmembrane protein encoded by the CD274 gene (Gene ID: 29126). Other abbreviated symbols for PD-L1 are B7-H, B7H1, PD-L1, PDCD1L1, PDCD1LG1, and PDL1PD-L1. The human CD274 gene can be found on chromosome 9 at the location NC_000009.12 (5450381 . . . 5470567) according to the Assembly from the Genome Reference Consortium Human Build 38 patch release 2 (GRCh38.p2), under RefSeq or GENBANK assembly accession No: GCF_000001405.28, dated Dec. 5, 2014. The mRNA of the human PD-L1 can be found at GENBANK accession Nos: NM_001267706.1, NM_014143.3, BC113734.1, BC113736.1, BC074984.2 and BC069381.1.

In one embodiment, the mRNA of the human PD-L1 is the isoform b precursor of the mRNA (variant 2) having the DNA sequence of atgaggatattt gctgtcttta tattcatgac ctactggcat ttgctgaacg ccccatacaa caaaatcaac caaagaattt tggttgtgga tccagtcacc tctgaacatg aactgacatg tcaggctgag ggctacccca aggccgaagt catctggaca agcagtgacc atcaagtcct gagtggtaag accaccacca ccaattccaa gagagaggag aagcttttca atgtgaccag cacactgaga atcaacacaa caactaatga gatttctct tgcacttta ggagatttaga tcctgaggaa aaccatacag ctgaattggt catcccagaa ctacctctgg cacatcctcc aaatgaaagg actcacttgg taattctggg agccatctta ttatgccttg gtgtagcact gacattcatc ttccgtttaa gaaagggag aatgatggat gtgaaaaat gtggcatcca agatacaaac tcaaagaagc aaagtgatac acatttggag gagacgtaa (SEQ. ID. NO: 1). This variant 2 represents the shorter transcript and encodes the shorter isoform b.

In one embodiment, the mRNA of the human PD-L1 is the isoform a precursor of the mRNA (variant 1) having the DNA sequence of atgaggatattt gctgtcttta tattcatgac ctactggcat ttgctgaacg catttactgt cacggttccc aaggacctat atgtggtaga gtatggtagc aatatgacaa ttgaatgcaa attcccagta gaaaaacaat tagacctggc tgcactaatt gtctattggg aaatggagga taagaacatt attcaatttg tgcatggaga ggaagacctg aaggttcagc atagtagcta cagacagagg gcccggctgt tgaaggacca gctctccctg ggaaatgctg cacttcagat cacagatgtg aaattgcagg atgcagggt gtaccgctgc atgatcagct atggtggtgc cgactacaag cgaattactg tgaaagtcaa tgccccatac aacaaaatca accaaagaat tttggttgtg gatccagtca cctctgaaca tgaactgaca tgtcaggctg agggctaccc caaggccgaa gtcatctgga caagcagtga ccatcaagtc ctgagtggta agaccaccac caccaattcc aagagagagg agaagcttlt caatgtgacc agcacactga gaatcaacac aacaactaat gagallllict actgcacttt taggagatta gatcctgagg aaaaccatac agctgaattg gtcatcccag aactacctct ggcacatcct ccaaatgaaa ggactcactt ggtaattctg ggagccatct tattatgcct tggtgtagca ctgacattca tcttccgttt aagaaaaggg agaatgatgg atgtgaaaaa atgtggcatc caagatacaa actcaaagaa gcaaagtgat acacatttgg aggagacgta a (SEQ. ID. NO: 2). This variant 1 represents the longest transcript and encodes the longer isoform a.

PD-L1 plays a major role in suppressing the immune system during particular events such as pregnancy, tissue allografts, autoimmune disease and other disease states such as hepatitis. Normally the immune system reacts to foreign antigens where there is some accumulation in the lymph nodes or spleen which triggers a proliferation of antigen-specific CD8+ T cell. The formation of PD-1 receptor/PD-L1 or B7.1 receptor/PD-L1 ligand complex transmits an inhibitory signal which reduces the proliferation of these CD8+ T cells at the lymph nodes and supplementary to that PD-1 is also able to control the accumulation of foreign antigen specific T cells in the lymph nodes through apoptosis which is further mediated by a lower regulation of the gene BCL-2.

PD-L1 protein is upregulated on macrophages and dendritic cells (DC) in response to LPS and GM-CSF treatment, and on T cells and B cells upon TCR and B cell receptor signaling. PD-L1 is expressed in a variety of tissues and cells, e.g., heart, lung, thymus, spleen, kidney and HSCs. PD-L1 is expressed on almost all murine tumor cell lines, including PA1 myeloma, P815 mastocytoma, and B16 melanoma upon treatment with IFN-γ.

In one embodiment, the nucleic acid encoding a PD-L1 encodes a human PD-L1.

In one embodiment of the population of modified HSCs, the ex vivo method, or the composition described herein, the nucleic acid encoding PD-L1 is a copy DNA (cDNA). In one embodiment, the cDNA encoding PD-L1 is an mRNA. In one embodiment, the mRNA is SEQ. ID. NO: 1 or 2. In other embodiments, the mRNA is derived from the GenBank accession Nos: NM_001267706.1, NM_014143.3, BC113734.1, BC113736.1, BC074984.2 or BC069381.1.

In another embodiment of the population of modified HSCs, the ex vivo method, or the composition described herein, the nucleic acid encoding PD-L1 is a genomic DNA. In one embodiment, the genomic DNA encoding PD-L1 is derived from the GenBank assembly accession No: GCF_000001405.28.

In one embodiment of the population of modified HSCs, the ex vivo method, or the composition described herein, the nucleic acid is integrated into the genome of the HSC cells.

In one embodiment of the population of modified HSCs, the ex vivo method, or the composition described herein, the nucleic acid is introduced into the cells via a vector.

In one embodiment of the population of modified HSCs, the ex vivo method, or the composition described herein, the vector is a viral vector.

In one embodiment of the population of modified HSCs, the ex vivo method, or the composition described herein, the viral vector is a lentiviral vector, an avian virus vector or an adeno-associated virus.

In one aspect of any method, the lentivirus is selected from the group consisting of: human immunodeficiency virus type 1 (HIV-1), human immunodeficiency virus type 2 (HIV-2), caprine arthritis-encephalitis virus (CAEV), equine infectious anemia virus (EIAV), feline immunodeficiency virus (FIV), bovine immune deficiency virus (BIV), and simian immunodeficiency virus (SIV).

In particular embodiments, cells transduced with the vectors contemplated herein are genetically modified.

In various embodiments, the genetically modified cells contemplated herein are transduced in vitro or ex vivo with vectors carrying an exogenous copy of a nucleic acid encoding a PD-L1, and optionally culture expanded ex vivo. The transduced cells are then administered to a subject in need of gene therapy. Alternatively, the transduced cells can be cryopreserved prior to administered to a subject in need of gene therapy.

In one embodiment of the population of modified HSCs, the ex vivo method, or the composition described herein, the cells are mammalian cells.

In one embodiment of the population of modified HSCs, the ex vivo method, or the composition described herein, the mammalian cells are human cells.

HSCs are known to give rise to committed hematopoietic progenitor cells (HPCs) that are capable of generating the entire repertoire of mature blood cells over the lifetime of an organism. The term "hematopoietic stem cell" or "HSC" generally refers to multipotent stem cells that give rise to the all the blood cell types of an organism, including myeloid (e.g., monocytes and macrophages, neutrophils, basophils, eosinophils, erythrocytes, megakaryocytes/platelets, dendritic cells), and lymphoid lineages (e.g., T-cells, B-cells, NK-cells), and others known in the art (See Fei, R., et al., U.S. Pat. No. 5,635,387; McGlave, et al., U.S. Pat. No. 5,460,964; Simmons, P., et al., U.S. Pat. No. 5,677,136; Tsukamoto, et al., U.S. Pat. No. 5,750,397; Schwartz, et al., U.S. Pat. No. 5,759,793; DiGuisto, et al., U.S. Pat. No. 5,681,599; Tsukamoto, et al., U.S. Pat. No. 5,716,827). When transplanted into lethally irradiated animals or humans, hematopoietic stem and progenitor cells can repopulate the erythroid, neutrophil-macrophage, megakaryocyte and lymphoid hematopoietic cell pool.

Mature blood cells have a finite lifespan and must be continuously replaced throughout life. Blood cells are produced by the proliferation and differentiation of a very small population of pluripotent HSCs that also have the ability to replenish themselves by self-renewal. HSCs are multipotent, self-renewing progenitor cells that develop from mesodermal hemangioblast cells. HSCs are the blood cells that give rise to all the other blood cells, that includes all the differentiated blood cells from the erythroid, lymphoid and myeloid lineages. HSCs are located in the adult bone marrow, peripheral blood, and umbilical cord blood.

During differentiation, the progeny of HSCs progress through various intermediate maturational stages, generating multi-potential hematopoietic progenitor cells and lineage-committed hematopoietic progenitor cells, prior to reaching maturity. Bone marrow (BM) is the major site of hematopoiesis in humans and, under normal conditions, only small numbers of HSCs and hematopoietic progenitor cells can be found in the peripheral blood (PB). Treatment with cytokines (in particular granulocyte colony-stimulating factor; G-CSF), myelosuppressive drugs used in cancer treatment, and compounds that disrupt the interaction between hematopoietic cells and BM stromal cells can rapidly mobilize large numbers of stem and progenitor cells into the circulation.

"Hematopoietic progenitor cell" as the term is used herein, refers to cells of a hematopoietic stem cell lineage that give rise to all the blood cell types including the myeloid (monocytes and macrophages, neutrophils, basophils, eosinophils, erythrocytes, megakaryocytes/platelets, dendritic cells), and the lymphoid lineages (T-cells, B-cells, NK-cells). A "cell of the erythroid lineage" indicates that the cell being contacted is a cell that undergoes erythropoeisis such that upon final differentiation it forms an erythrocyte or red blood cell (RBC). Such cells belong to one of three lineages, erythroid, lymphoid, and myeloid, originating from bone marrow hematopoietic progenitor cells. Upon exposure to specific growth factors and other components of the hematopoietic microenvironment, hematopoietic progenitor cells can mature through a series of intermediate differentiation cellular types, all intermediates of the erythroid lineage, into RBCs. Thus, cells of the "erythroid lineage," as the term is used herein, comprise hematopoietic progenitor cells, rubriblasts, prorubricytes, erythroblasts, metarubricytes, reticulocytes, and erythrocytes.

The HSCs, similar to the hematopoietic progenitor cells, are capable of proliferation and giving rise to more progenitor cells having the ability to generate a large number of mother cells that can in turn give rise to differentiated or differentiable daughter cells. The daughter cells themselves can be stimulated to proliferate and produce progeny that subsequently differentiate into one or more mature cell types, while also retaining one or more cells with parental developmental potential. The term "stem cell" refers then, to a cell with the capacity or potential, under particular circumstances, to differentiate to a more specialized or differentiated phenotype, and which retains the capacity, under certain circumstances, to proliferate without substantially differentiating. In one embodiment, the term progenitor or stem cell refers to a generalized mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "multipotent" because they can produce progeny of more than one distinct cell type, but this is not required for "stem-ness." Self-renewal is the other classical part of the stem cell definition, and it is essential as used in this document. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Generally, "progenitor cells" have a cellular phenotype that is more primitive (i.e., is at an earlier step along a developmental pathway or progression than is a fully differentiated cell). Often, progenitor cells also have significant or very high proliferative potential. Progenitor cells can give rise to multiple distinct differentiated cell types or to a single differentiated cell type, depending on the developmental pathway and on the environment in which the cells develop and differentiate.

Peripheral blood progenitor cells (PBPC) have become the preferred source of hematopoetic progenitor cells and HSCs for allogeneic and autologous transplantation because of technical ease of collection and shorter time required for engraftment. Traditionally, granulocyte-colony stimulating factor (G-CSF) has been used to stimulate more PBPC and release of hematopoetic progenitor cells from the bone marrow. Although regimens using G-CSF usually succeed in collecting adequate numbers of PBPC from healthy donors, 5%-10% will mobilize stem cells poorly and may require multiple large volume apheresis or bone marrow harvesting.

In one embodiment of the population of modified HSCs, the ex vivo method, or the composition described herein, prior to the modification, the sample of HSCs is obtained from the bone marrow, umbilical cord, chorionic villi, amniotic fluid, placental blood, cord blood or peripheral blood. In one embodiment, the HSCs are isolated from the bone marrow, umbilical cord, chorionic villi, amniotic fluid, placental blood, cord blood or peripheral blood.

In one embodiment of the population of modified HSCs, the ex vivo method, or the composition described herein, the sample of HSCs is obtained from mobilized peripheral blood. Methods of mobilizing HSCs from the places of origin or storage are known in the art. For example, treatment with cytokines, in particular granulocyte colony-stimulating factor (G-CSF) and compounds (e.g., plerixafor, a chemokine CXCR4 antagonist) that disrupt the interaction between HSCs and bone marrow (BM) stromal cells can rapidly mobilize large numbers of hematopoietic stem and hematopoietic progenitor cells into the circulation. In one embodiment of the population of modified HSCs, the ex vivo method, or the composition described herein, the sample of HSCs is CD34$^+$ selected cells obtained from the bone marrow, umbilical cord, chorionic villi, amniotic fluid, placental blood, cord blood or peripheral blood, or mobilized peripheral blood.

In one embodiment of the population of modified HSCs, the ex vivo method, or the composition described herein, the HSCs are CD34$^+$ cells. In other embodiments, the HSCs are CD38$^{lo/-}$ cells. In other embodiments, the HSCs are c-kit$^+$ cells.

In one embodiment of the population of modified HSCs, the ex vivo method, or the composition described herein, the HSCs are hematopoietic progenitor cells. In one embodiment, these hematopoietic progenitor cells are CD34$^+$ cells. In other embodiments, these hematopoietic progenitor cells are CD38$^{lo/-}$ cells. In other embodiments, these hematopoietic progenitor cells are c-kit$^+$ cells.

In one embodiment of the population of modified HSCs, the ex vivo method, or the composition described herein, the HSCs are erythroid progenitor cells. In one embodiment, these erythroid progenitor cells are CD34$^+$ cells.

In one embodiment of the population of modified HSCs, the ex vivo method, or the composition described herein, the HSCs are erythroid cells. In one embodiment, these erythroid cells are CD34$^+$ cells.

In one embodiment of the population of modified HSCs, the ex vivo method, or the composition described herein, the HSC is selected for the CD34$^+$ surface marker prior to the contacting with the vector carrying the exogenous copy of the nucleic acid described herein.

In other embodiment of the population of modified HSCs, the ex vivo method, or the composition described herein, the HSC is selected for the CD38$^{lo/-}$ surface marker prior to the contacting with the vector carrying the exogenous copy of the nucleic acid described herein.

In one embodiment of the population of modified HSCs, the ex vivo method, or the composition described herein, the HSC is selected for the c-kit$^+$ surface marker prior to the contacting with the vector carrying the exogenous copy of the nucleic acid described herein. Positive or negative selection for the described surface markers can be performed by any method known in the art, e.g., using the anti-CD34 immunomagnetic bead described in the Example section.

It one embodiment of the population of modified HSCs, the ex vivo method, or the composition described herein, the isolated CD34$^+$ HSC is contacted with the PGE$_2$ composition described herein or contacted with the vector carrying the exogenous copy of the nucleic acid described herein.

In one embodiment of the population of modified HSCs, the ex vivo method, or the composition described herein, the HSC has at least one of the cell surface marker characteristic of HSCs: CD34$^+$, CD59$^+$, Thy1/CD90$^+$, CD38$^{lo/-}$, and C-kit/CD117$^+$. Preferably, the HSCs have several of these markers.

In one embodiment of the population of modified HSCs, the ex vivo method, or the composition described herein, the HSCs are CD34$^+$, CD59$^+$, Thy1/CD90$^+$, CD38$^{lo/-}$, and C-kit/CD117$^+$.

In one embodiment of the population of modified HSCs, the ex vivo method, or the composition described herein, the HSCs are CD 133$^+$.

In one embodiment of the population of modified HSCs, the ex vivo method, or the composition described herein, the hematopoietic progenitor cells are CD 133$^+$.

In one embodiment of the population of modified HSCs, the ex vivo method, or the composition described herein, the hematopoietic progenitor cells of the erythroid lineage have the cell surface marker characteristic of the erythroid lineage: CD71 and Ter119.

In one embodiment of the population of modified HSCs, the ex vivo method, or the composition described herein, the HSCs have the cell surface marker characteristic of the erythroid lineage: CD71 and Ter119.

In one embodiment of the population of modified HSCs, the ex vivo method, or the composition described herein, the HSCs have at least one of the cell surface marker selected from the group consisting of CD34$^+$, CD59$^+$, Thy1/CD90$^+$, CD38$^{lo/-}$, and C-kit/CD117$^+$.

In one embodiment of the population of modified HSCs, the ex vivo method, or the composition described herein, the HSCs are positively selected for at least one of the cell surface marker selected from the group consisting of CD34$^+$, CD59$^+$, Thy1/CD90$^+$, and C-kit/CD117$^+$. In another embodiment of the population of modified HSCs, the ex vivo method, or the composition described herein, the HSCs are negatively selected for CD38$^{lo/-}$.

In one embodiment of the population of modified HSCs, the ex vivo method, or the composition described herein, the sample of HSCs is obtained from a healthy individual or subject.

In one embodiment of the population of modified HSCs, the ex vivo method, or the composition described herein, the HSCs are obtained or isolated from an individual with a diagnosed disease or disorder or an individual who is an organ or bone marrow transplant recipient.

In one embodiment of the population of modified HSCs, the ex vivo method, or the composition described herein, the HSCs are obtained or isolated from an individual who is newly diagnosed with T1D.

In one embodiment of the population of modified HSCs, the ex vivo method, or the composition described herein, the diagnosed disease or disorder is an autoimmune disease or disorder.

In one embodiment of the population of modified HSCs, the ex vivo method, or the composition described herein, the autoimmune disease or disorder is T1D.

In one embodiment of the population of modified HSCs, the ex vivo method, or the composition described herein, the contacting of the HSCs with the vector carrying the exogenous copy of the nucleic acid described herein is repeated at least once. That is, after the initial first contacting of the HSC with the virus or vector described herein, the cell is washed and collected, and the washed cell is then contacted for a second time with the virus or vector carrying a nucleic acid molecule described herein. These cells are then washed a second time and collected.

In other embodiments of the population of modified HSCs, the ex vivo method, or the composition described herein, the contacting is repeated at least twice after the initial first contacting.

In one embodiment of the population of modified HSCs, the ex vivo method, or the composition described herein, the isolated or collected HSCs are ex vivo cultured before and/or after the introduction of the exogenous copy of a nucleic acid encoding a PD-L1. In one embodiment, the ex vivo culturing serve to expand or grow the population of present cells, that is, to increase the number of similar cells.

In one embodiment of the population of modified HSCs, the ex vivo method, or the composition described herein, the isolated or collected HSCs are ex vivo cultured before contacting, incubation or stimulation with $PGE_2$.

In one embodiment of the population of modified HSCs, the ex vivo method, or the composition described herein, the isolated or collected HSCs are ex vivo cultured after contacting, incubation or stimulation with $PGE_2$.

In one embodiment of the population of modified HSCs, the ex vivo method, or the composition described herein, the isolated or collected HSCs are ex vivo cultured before and after contacting, incubation or stimulation with $PGE_2$.

In another embodiment, the ex vivo culture expansion take place prior to use, for example, use in cryopreservation, or use in implantation/engraftment into a recipient subject.

In one embodiment of the population of modified HSCs, the ex vivo method, or the composition described herein, the HSCs are cryopreserved prior to the introduction of the exogenous copy of a nucleic acid encoding a PD-L1.

In one embodiment of the population of modified HSCs, the ex vivo method, or the composition described herein, the HSCs are cryopreserved after the introduction of the exogenous copy of a nucleic acid encoding a PD-L1.

In one embodiment of the population of modified HSCs, the ex vivo method, or the composition described herein, the HSCs are cryopreserved prior to and after the introduction of the exogenous copy of a nucleic acid encoding a PD-L1.

In one embodiment of the population of modified HSCs, the ex vivo method, or the composition described herein, the HSCs are cryopreserved prior to contacting, incubation or stimulatiot with $PGE_2$, or after contacting, incubation or stimulatiot with $PGE_2$, or both prior to and after contacting, incubation or stimulatiot with $PGE_2$.

In one embodiment of the population of modified HSCs, the ex vivo method, or the composition described herein, the modified PD-L1$^+$ expressing HSCs are ex vivo culture expanded and then cryopreserved prior to use. For example, ex vivo cell expansion and/or implantation/engraftment into a subject.

The cells described herein can be cryopreserved by any methods known in the art. As used herein, "cryopreserving" refers to the preservation of cells by cooling to low sub-zero temperatures, such as (typically) 77 K or −196° C. (the boiling point of liquid nitrogen). Cryopreservation also refers to preserving cells at a temperature between 4-10° C. At these low temperatures, any biological activity, including the biochemical reactions that would lead to cell death, is effectively stopped. Cryoprotective agents are often used at sub-zero temperatures to prevent the cells being preserved from damage due to freezing at low temperatures or warming to room temperature.

Freezing is destructive to most living cells. Upon cooling, as the external medium freezes, cells equilibrate by losing water, thus increasing intracellular solute concentration. Below about 10°-15° C., intracellular freezing will occur. Both intracellular freezing and solution effects are responsible for cell injury (Mazur, P., 1970, Science 168:939-949). It has been proposed that freezing destruction from extracellular ice is essentially a plasma membrane injury resulting from osmotic dehydration of the cell (Meryman, H. T., et al., 1977, Cryobiology 14:287-302).

Cryoprotective agents and optimal cooling rates can protect against cell injury. Cryoprotective agents which can be used include but are not limited to dimethyl sulfoxide (DMSO) (Lovelock, J. E. and Bishop, M. W. H., 1959, Nature 183:1394-1395; Ashwood-Smith, M. J., 1961, Nature 190:1204-1205), glycerol, polyvinylpyrrolidine (Rinfret, A. P., 1960, Ann. N.Y. Acad. Sci. 85:576), Dextran, trehalose, CryoSoFree (Signa Aldrich Co.) and polyethylene glycol (Sloviter, H. A. and Ravdin, R. G., 1962, Nature 196:548). The preferred cooling rate is 1° to 3° C./minute. After at least two hours, the T-cells have reached a temperature of −80° C. and can be placed directly into liquid nitrogen (−196° C.) for permanent storage such as in a long-term cryogenic storage vessel.

In one embodiment of the population of modified HSCs, the ex vivo method, or the composition described herein, the $PGE_2$ is 16,16-Dimethyl prostaglandin E2 (dm$PGE_2$).

Uses of PD-L1 Expressing HSCs and Compositions Comprising these HSCs

The modified PD-L1 expressing HSCs described herein can be used to treat an autoimmune disorder, getting to the root cause of an autoimmune disorder, a defect in immuno-regulation. The modified PD-L1 expressing HSCs are used to modulate or suppress an immune response in a subject having the autoimmune disorder. In one embodiment, the autoimmune disorder is T1D. Subjects with T1D have defects in producing PD-L1 expression HSCs. The modified PD-L1 expressing HSCs are used to supplement this defect and modulate or suppress the immune response against the β islet cells of the panceaus of the subject having T1D. In one embodiment, the modified PD-L1 expressing HSCs described herein are used to treat T1D in a subject diagnosed with T1D. In one embodiment, the subject is newly diagnosed with T1D. As used herein, the term "newly diagnosed" refers to diagnosis for the disorder for less than one calendar year. In one embodiment, the subject is newly been detected to have self-autoantibodies associated with T1D, e.g., GAD65 autoantibody, and islet antigen 2 autoantibody.

As used herein, the term "newly detected" refers to the detection of self-autoantibodies associated with T1D in the last 6 calender months.

For example, a human subject has been newly diagnosed with T1D. A sample of HSCs can be harvested from this subject. The HSCs obtained can be ex vivo expanded to increase the number of available HSCs for the procedures described herein to increase PD-L1 expression. A sample of HSCs can be transfected with an exogenous of a PD-L1 cDNA to bring about overexpression of PD-L1 in the transfected HSCs. Alternatively, a sample of HSCs can be contacted ex vivo with $PGE_2$ as described herein to stimulate increased PD-L1 expression in the $PGE_2$-contacted HSCs. Both $PGE_2$ and steroids such as dexamethasome also can be use together to stimulate PD-L1 expression. Either method of increasing PD-L1 expression and increasing the pool of PD-L1 expressing HSCs can be used. The resultant HSCs are then analysed to confirmed increased PD-L1 expression compared to non-transfected HSCs or non-$PGE_2$-contacted HSCs respectively. The resultant HSCs can be further ex vivo expanded to increase the number of available HSCs for transplantation back into the subject. The resultant HSCs can also be ex vivo expanded to increase the number of available PD-L1 expressing HSCs for cryopreservation and for transplantation back into the subject, i.e., have a portion of PD-L1 expressing HSCs kept in cryostorage and another portion for transplantation back into the subject. The PD-L1 expressing HSCs are autologous to the recipient subject because the original HSCs were obtained from the same subject, therefore the HSCs are HLA matched to the subject.

For example, a human subject has been newly been detected to have self-autoantibodies associated with T1D, e.g., GAD65 autoantibody, and islet antigen 2 autoantibody. The four autoantibodies that are markers of beta cell autoimmunity in type 1 diabetes are: islet cell antibodies (ICA, against cytoplasmic proteins in the beta cell), antibodies to glutamic acid decarboxylase (GAD-65), insulin autoantibodies (IAA), and IA-2A, to protein tyrosine phosphatase. Autoantibodies against GAD 65 are found in 80% of type 1 diabetics at clinical presentation. Presence of ICA and IA-2A at diagnosis for type 1 diabetes range from 69-90% and 54-75%, respectively. IAA prevalence correlates inversely with age at onset of diabetes; it is usually the first marker in young children at risk for diabetes and found in approximately 70% of young children at time of diagnosis. The subject is not yet symptomatic for T1D (ie., hyperglycemia). The therapeutic methods using the PD-L1 expressing HSCs are used to delay onset of hyperglycemia for such an individual. Hyperglycemia, or high blood sugar is a condition in which an excessive amount of glucose circulates in the blood plasma. This is generally a blood sugar level higher than 11.1 mmol/l (200 mg/dl), but symptoms may not start to become noticeable until even higher values such as 15-20 mmol/l (~250-300 mg/dl). A subject with a consistent range between ~5.6 and ~7 mmol/l (100-126 mg/dl) (American Diabetes Association guidelines) is considered hyperglycemic, while above 7 mmol/l (126 mg/dl) is generally held to have diabetes. In one embodiment, the subject has blood sugar below 11.1 mmol/l (200 mg/dl). In another embodiment, the blood sugar below 15 mmol/l (~250 mg/dl) or below 20 mmol/l 300 mg/dl). Administering the PD-L1$^+$ cells can delay the onset of diabetes.

The modified PD-L1 expressing HSCs described herein can also be used to suppress an immune response in a subject who is an organ or bone marrow transplant recipient, or a subject who is going to be recipient in the near further. The modified PD-L1 expressing HSCs are used to prevent or treat or both prevent and treat host-versus-graft disease (GVHD). GvHD is a medical complication following the receipt of transplanted tissue from a genetically different person. GvHD is commonly associated with stem cell or bone marrow transplant but the term also applies to other forms of tissue graft. A sample of HSCs can be harvested from this subject. The HSCs obtained can be ex vivo expanded to increase the number of available HSCs for the procedures described herein to increase PD-L1 expression. A sample of HSCs can be transfected with an exogenous of a PD-L1 cDNA to bring about overexpression of PD-L1 in the transfected HSCs. Alternatively, a sample of HSCs can be contacted ex vivo with $PGE_2$ as described herein to stimulate increase PD-L1 in the $PGE_2$-contacted HSCs. Both $PGE_2$ and a steroid such as dexamethasome can be use together to stimulate PD-L1 expression. Either method of increasing PD-L1 expression and increasing the pool of PD-L1 expressing HSCs can be used. The resultant HSCs are then analysed to confirmed increased PD-L1 expression compared to non-transfected HSCs or non-$PGE_2$-contacted HSCs respectively. The resultant HSCs can be further ex vivo expanded to increase the number of available HSCs for transplantation back into the subject. The resultant HSCs can also be ex vivo expanded to increase the number of available PD-L1 expressing HSCs for cryopreservation and for transplantation back into the subject.

Accordingly, in one embodiment, provided herein is a composition comprising the PD-L1 expressing hematopoietic stem cells described herein or PD-L1$^+$ HSCs produced by any one of the method described herein for use in the prevention or treatment of an autoimmune disease or disorder, for use in suppressing an immune response in a subject, for use in the delay of the onset of T1D in a subject at risk of developing T1D, for use in the prevention and delay of an allogenic tissue or organ transplant rejection, and for the treatment of T1D in adult and pediatric subjects.

In one embodiment, provided herein is a composition comprising the PD-L1 expressing HSCs described herein or PD-L1$^+$ HSCs produced by any one of the method described herein for the manufacture of medicament for use in the prevention or treatment of an autoimmune disease or disorder, in the suppression of an immune response in a subject, in the delay of the onset of T1D in a subject at risk of developing T1D, in the prevention and delay of an allogenic tissue or organ transplant rejection, and for the treatment of T1D in adult and pediatric subjects.

In another embodiment, provided herein is a population of PD-L1 expressing HSCs described herein or PD-L1$^+$ HSCs produced by any one of the method described herein for use in the prevention or treatment of an autoimmune disease or disorder, for use in suppressing an immune response in a subject, for use in the delay of the onset of T1D in a subject at risk of developing T1D, for use in the prevention and delay of an allogenic tissue or organ transplant rejection, and for the treatment of T1D in adult and pediatric subjects.

In another embodiment, provided herein is a population of PD-L1 expressing HSCs described herein or PD-L1$^+$ HSCs produced by any one of the method described herein for the manufacture of medicament for use in the prevention or treatment of an autoimmune disease or disorder, in the suppression of an immune response in a subject, in the delay of the onset of T1D in a subject at risk of developing T1D, in the prevention and delay of an allogenic tissue or organ transplant rejection, and for the treatment of T1D in adult and pediatric subjects.

Accordingly, in one embodiment, provided herein is a method of treating an autoimmune disorder or suppressing an immune response in a subject in need thereof, the method comprising administering to a subject a composition comprising a population of modified HSCs described herein. In one embodiment, the modified HSCs express PD-L1. In one embodiment, the modified HSCs exhibit increase expression of PD-L1 over the control, non-modified HSCs. In one embodiment, the method further comprises identifying a subject afflicted with an autoimmune disease or disorder. In another embodiment, the method further comprises selecting a subject having an autoimmune disease or disorder, or or an individual who is an organ or bone marrow transplant recipient.

In one embodiment, provided herein is a method of preventing host-versus-graft disease, or organ or tissue graft rejection in a subject in need thereof, the method comprising administering to a subject a composition comprising a population of modified HSCs described herein. In one embodiment, the subject has received an allogenic tissue or organ graft. In one embodiment, the modified HSCs carry an exogenous copy of a nucleic acid encoding a PD-L1. In one embodiment, the modified HSCs express PD-L1. In one embodiment, the modified HSCs exhibit increase expression of PD-L1 over the control, non-modified HSCs.

In one embodiment, the modified HSCs are $PGE_2$-stimulated, PD-L1$^+$ expressing HSCs described herein. In one embodiment, the modified HSCs are $PGE_2$ and dexamethasone-stimulated, PD-L1+ expressing HSCs described herein.

In one embodiment, provided herein is a method of delaying the onset of Type 1 diabetes in a subject in need thereof, the method comprising administering to a subject a composition comprising a population of modified HSCs described herein. In one embodiment, the subject is newly been noted to have detectable amounts of a self-autoantibody associated with T1D. In one embodiment, the subject does not have clinical hyperglycemia. In one embodiment, the subject is a pediatric patient under the age of 20 years old. In other embodiments, the subject is a pediatric patient under the age of 15 years old, 10 years old, 5 years old, and 1 years old. In one embodiment, the modified HSCs carry an exogenous copy of a nucleic acid encoding a PD-L1. In one embodiment, the modified HSCs express PD-L1. In one embodiment, the modified HSCs exhibit increase expression of PD-L1 over the control, non-modified HSCs.

In one embodiment, the modified HSCs are $PGE_2$-stimulated, PD-L1$^+$ expressing HSCs described herein. In one embodiment, the modified HSCs are $PGE_2$ and dexamethasone-stimulated, PD-L1+ expressing HSCs described herein.

A variety of autoimmune diseases or disorders are known in the art, for example, those described in the definition section. The skilled physician would be able to diagnose an autoimmune disease or disorder that is known in the art.

In another embodiment, the method further comprises selecting a subject in need of immune response suppression. In general, deliberately induced immunosuppression is performed to prevent the body from rejecting an organ transplant or an allograft transplant, treating GVHD after an organ or bone marrow transplant, or for the treatment of autoimmune diseases such as systemic lupus erythematosus, rheumatoid arthritis or Crohn's disease. In some embodiments, an organ transplantation include liver, skin, lung transplantation, pancreas, kidney, ovary, colon, intestine, and heart transplantation.

In one embodiment, provided herein is a method of treating an autoimmune disorder or suppressing an immune response in a subject in need thereof, the method comprising administering to a subject a composition comprising a population of modified HSCs where the modified HSCs carry an exogenous copy of a nucleic acid encoding a PD-L1. In one embodiment, the modified HSCs express PD-L1. In one embodiment, the modified HSCs exhibit increase expression of PD-L1 over the control, non-modified HSCs.

In one embodiment, provided herein is a method of treating an autoimmune disorder or suppressing an immune response in a subject in need thereof, the method comprising administering to a subject a composition comprising a population of modified PD-L1$^+$ expressing HSCs where the modified HSCs are produced by an ex vivo method comprising contacting a sample of HSCs with a vector carrying an exogenous copy of a nucleic acid encoding a PD-L1 to modify the HSCs whereby the exogenous copy of a nucleic acid is introduced into the HSCs, thereby producing a population of modified HSCs cells expressing PD-L1. In one embodiment, the method further comprises establishing the expression of PD-L1 on the resultant modified HSCs.

In another embodiment, the method further comprises ex vivo culturing the resultant modified cells after contact with the vector. In another embodiment, the method further comprises ex vivo culturing the resultant modified cells after establishing the expression of PD-L1 on the resultant modified HSCs. In another embodiment, the method further comprises ex vivo culturing the resultant modified cells after contact with the vector and ex vivo culturing the resultant modified cells after establishing the expression of PD-L1 on the resultant modified HSCs.

In one embodiment, provided herein is a method of treating an autoimmune disorder or suppressing an immune response in a subject in need thereof, the method comprising administering to a subject a composition comprising a population of $PGE_2$-stimulated, PD-L1+ expressing HSCs described herein. In one embodiment, the method further comprises identifying a subject afflicted with an autoimmune disease or disorder.

In another embodiment, the method further comprises selecting a subject having an autoimmune disease or disorder, or a subject who is an organ or bone marrow transplant recipient, or a subject who is an organ or bone marrow transplant recipient and is at risk of developing GVHD. For example, a subject who has received an allogenic graft transplant. In another embodiment, the method further comprises selecting a subject in need of immune response suppression. For example, a subject who an organ or bone marrow transplant recipient and is at risk of developing GVHD.

In one embodiment, provided herein is a method of treating an autoimmune disorder or suppressing an immune response in a subject in need thereof, the method comprising administering to a subject a composition comprising a population of PD-L1$^+$ expressing HSCs wherein the HSCs are stimulated to express PD-L1$^+$ by contacting with $PGE_2$. In one embodiment, the stimulated HSCs exhibit an increase expression of PD-L1 over the control, non-$PGE_2$-stimulated HSCs.

In one embodiment, provided herein is a method of treating an autoimmune disorder or suppressing an immune response in a subject in need thereof, the method comprising administering to a subject a composition comprising a population of PD-L1$^+$ expressing HSCs where the PD-L1$^+$ expressing HSCs are produced by an ex vivo method comprising contacting a sample of HSCs with $PGE_2$ at 10

μM concentration for about 60 min at 37° C., thereby producing a population of PGE$_2$-stimulated HSCs cells expressing PD-L1.

In one embodiment, provided herein is a method of treating an autoimmune disorder or suppressing an immune response in a subject in need thereof, the method comprising administering to a subject a composition comprising a population of PD-L1$^+$ expressing HSCs where the PD-L1$^+$ expressing HSCs are produced by an ex vivo method comprising contacting a sample of HSCs with PGE$_2$ at 0.1 μM concentration for at least 24 hrs at 37° C., thereby producing a population of PGE$_2$-stimulated HSCs cells expressing PD-L1.

In one embodiment of the above described method, the method further comprises washing the contacted cells to remove excess PGE$_2$. In one embodiment, the method further comprises establishing the expression of PD-L1 on the PGE$_2$-stimulated HSCs. In another embodiment, the method further comprises ex vivo culturing of the sample of HSCs prior to PGE$_2$-stimulation. This ex vivo culturing expands the number of cells available for PGE$_2$-stimulation. In another embodiment, the method further comprises ex vivo culturing of the PGE$_2$-stimulated HSCs after contact with PGE$_2$, or ex vivo culturing of the PGE$_2$-stimulated HSCs after establishing the expression of PD-L1 on the PGE$_2$-stimulated HSCs, or both ex vivo culturing of the PGE$_2$-stimulated HSCs after contact with PGE$_2$ and ex vivo culturing of the PGE$_2$-stimulated HSCs after establishing the expression of PD-L1 on the PGE$_2$-stimulated HSCs. This ex vivo culturing expands the number of PD-L1 expressing cells available for therapy.

In one embodiment, provided herein is a method of treating an autoimmune disorder or suppressing an immune response in a subject in need thereof, the method comprising providing a population of HSCs; contacting the sample of HSCs with a vector carrying an exogenous copy of a nucleic acid encoding a PD-L1 to produce a population of modified HSCs cells expressing PD-L1; and adminstering the population of modified, PD-L1$^+$ expressing HSCs into a recipient subject to promote immunoregulation and immuneself-tolerance in the recipient subject. In one embodiment, the method further comprises establishing the expression of PD-L1 on the resultant modified HSCs. In another embodiment, the method further comprises ex vivo culturing the resultant modified cells after contact with the vector and/or ex vivo culturing the resultant modified cells after establishing the expression of PD-L1 on the resultant modified HSCs. In one embodiment, the treatment method further comprises identifying a recipient subject afflicted with an autoimmune disease or disorder and is in need of increased immunoregulation and immune self-tolerance. In another embodiment, the treatment method further comprises selecting a recipient subject having an autoimmune disease or disorder or is in need of suppressing an immune response. In another embodiment, the treatment method further comprises identifying and selecting a donor subject to provide the sample of HSCs for contacting with the described vector or stimulation with PGE$_2$. In one embodiment, the donor subject and recipient subject are the same subject, that is the recipient subject would be administered autologous HSCs. In another embodiment, the donor subject and recipient subject are different subjects. In another embodiment, the donor subject and recipient subject at the minimum HLA type matched.

In one embodiment, provided herein is a method of treating an autoimmune disorder or suppressing an immune response in a subject in need thereof, the method comprising providing a population of HSCs; contacting sample of HSCs with PGE$_2$ at 10 μM concentration for about 60 min at 37° C. to produce a population of PGE$_2$-stimulated HSCs cells expressing PD-L1; and adminstering the population of PGE$_2$-stimulated PD-L1$^+$ expressing HSCs into a recipient subject to promote immunoregulation and immuneself-tolerance in the recipient subject. In one embodiment, the method further comprises establishing the expression of PD-L1 on the resultant PGE$_2$-stimulated HSCs.

In one embodiment, provided herein is a method of treating an autoimmune disorder or suppressing an immune response in a subject in need thereof, the method comprising providing a population of HSCs; contacting sample of HSCs with PGE$_2$ at 0.1 μM concentration for at least 24 hrs at 37° C. to produce a population of PGE$_2$-stimulated HSCs cells expressing PD-L1; and adminstering the population of PGE$_2$-stimulated PD-L1$^+$ expressing HSCs into a recipient subject to promote immunoregulation and immuneself-tolerance in the recipient subject. In one embodiment, the method further comprises establishing the expression of PD-L1 on the resultant PGE$_2$-stimulated HSCs.

In another embodiment of the above described methods, the PGE$_2$-stimulated HSCs are also contacted with steroids such as dexamethasone.

In another embodiment of the above described methods, the method further comprises ex vivo culturing the resultant PGE$_2$-stimulated cells after contact with PGE$_2$, or ex vivo culturing the resultant PGE$_2$-stimulated cells after establishing the expression of PD-L1 on the resultant PGE$_2$-stimulated HSCs, or both ex vivo culturing the resultant PGE$_2$-stimulated cells after contact with PGE$_2$ and ex vivo culturing the resultant PGE$_2$-stimulated cells after establishing the expression of PD-L1 on the resultant PGE$_2$-stimulated HSCs.

In one embodiment, the method further comprises identifying a recipient subject afflicted with an autoimmune disease or disorder and is in need of increased immunoregulation and immune self-tolerance. In one embodiment, the method further comprises identifying a recipient subject who is an organ or bone marrow transplant recipient, and is in need of increased immunoregulation and immune self-tolerance. In another embodiment, the method further comprises selecting a recipient subject having an autoimmune disease or disorder or who is an organ or bone marrow transplant recipient. In another embodiment, the treatment method further comprises identifying and selecting a donor subject to provide the sample of HSCs for contacting with PGE$_2$. In one embodiment, the donor subject and recipient subject are the same subject, that is the recipient subject would be administered autologous HSCs. In another embodiment, the donor subject and recipient subject are different subjects. In another embodiment, the donor subject and recipient subject at the minimum HLA type matched.

In one embodiment, the HSCs are isolated from a host subject, transfected with a vector, cultured (optional), and transplanted back into the same host, i.e. an autologous cell transplant. In another embodiment, the HSCs are isolated from a donor who is an HLA-type match with a host (recipient) who is diagnosed with an autoimmune disease or disorder, or T1D. Donor-recipient antigen type-matching is well known in the art. The HLA-types include HLA-A, HLA-B, HLA-C, and HLA-D. These represent the minimum number of cell surface antigen matching required for transplantation. That is the transfected cells are transplanted into a different host, i.e., allogeneic to the recipient host subject. The donor's or subject's HSCs can be transfected with a vector or nucleic acid comprising the nucleic acid molecule described herein, the transfected cells are culture expanded ex vivo, and then transplanted into the host subject. In one embodiment, the transplanted cells engrafts in the host subject. The transfected HSCs can also be cryopreserved after transfected and stored, or cryopreserved after cell expansion and stored.

In one embodiment of any one of the method described, the autoimmune disorder is selected from the group consisting of thyroiditis, type 1 diabetes mellitus, Hashimoto's thyroidits, Graves' disease, celiac disease, multiple sclerolsis, Guillain-Barre syndrome, Addison's disease, and Raynaud's phenomenon, Goodpasture's disease, arthritis (rheumatoid arthritis such as acute arthritis, chronic rheumatoid arthritis, gout or gouty arthritis, acute gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, and juvenile-onset rheumatoid arthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, atopy including atopic diseases such as hay fever and Job's syndrome, dermatitis including contact dermatitis, chronic contact dermatitis, exfoliative dermatitis, allergic dermatitis, allergic contact dermatitis, dermatitis herpetiformis, nummular dermatitis, seborrheic dermatitis, non-specific dermatitis, primary irritant contact dermatitis, and atopic dermatitis, x-linked hyper IgM syndrome, allergic intraocular inflammatory diseases, urticaria such as chronic allergic urticaria and chronic idiopathic urticaria, including chronic autoimmune urticaria, myositis, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, ataxic sclerosis, neuromyelitis optica (NMO), inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), bowel inflammation, pyoderma gangrenosum, erythema nodosum, primary sclerosing cholangitis, respiratory distress syndrome, including adult or acute respiratory distress syndrome (ARDS), meningitis, inflammation of all or part of the uvea, iritis, choroiditis, an autoimmune hematological disorder, rheumatoid spondylitis, rheumatoid synovitis, hereditary angioedema, cranial nerve damage as in meningitis, herpes gestationis, pemphigoid gestationis, pruritis scroti, autoimmune premature ovarian failure, sudden hearing loss due to an autoimmune condition, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, proliferative nephritis, autoimmune polyglandular endocrine failure, balanitis including balanitis circumscripta plasmacellularis, balanoposthitis, erythema annulare centrifugum, erythema dyschromicum perstans, eythema multiform, granuloma annulare, lichen nitidus, lichen sclerosus et atrophicus, lichen simplex chronicus, lichen spinulosus, lichen planus, lamellar ichthyosis, epidermolytic hyperkeratosis, premalignant keratosis, pyoderma gangrenosum, allergic conditions and responses, allergic reaction, eczema including allergic or atopic eczema, asteatotic eczema, dyshidrotic eczema, and vesicular palmoplantar eczema, asthma such as asthma bronchiale, bronchial asthma, and autoimmune asthma, conditions involving infiltration of T cells and chronic inflammatory responses, immune reactions against foreign antigens such as fetal A-B-O blood groups during pregnancy, chronic pulmonary inflammatory disease, autoimmune myocarditis, leukocyte adhesion deficiency, lupus, including lupus nephritis, lupus cerebritis, pediatric lupus, non-renal lupus, extra-renal lupus, discoid lupus and discoid lupus erythematosus, alopecia lupus, systemic lupus erythematosus (SLE) such as cutaneous SLE or subacute cutaneous SLE, neonatal lupus syndrome (NLE), and lupus erythematosus disseminatus, juvenile onset (Type I) diabetes mellitus, including pediatric insulin-dependent diabetes mellitus (IDDM), adult onset diabetes mellitus (Type II diabetes), autoimmune diabetes, idiopathic diabetes insipidus, diabetic retinopathy, diabetic nephropathy, diabetic large-artery disorder, immune responses associated with acute and delayed hypersensitivity mediated by cytokines and T-lymphocytes, sarcoidosis, granulomatosis including lymphomatoid granulomatosis, Wegener's granulomatosis, agranulocytosis, vasculitides, including vasculitis, large-vessel vasculitis (including polymyalgia rheumatica and giant-cell (Takayasu's) arteritis), medium-vessel vasculitis (including Kawasaki's disease and polyarteritis nodosa/periarteritis nodosa), microscopic polyarteritis, immunovasculitis, CNS vasculitis, cutaneous vasculitis, hypersensitivity vasculitis, necrotizing vasculitis such as systemic necrotizing vasculitis, and ANCA-associated vasculitis, such as Churg-Strauss vasculitis or syndrome (CSS) and ANCA-associated small-vessel vasculitis, temporal arteritis, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Behcet's disease/syndrome, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, an immune complex disorder such as immune complex nephritis, antibody-mediated nephritis, polyneuropathies, chronic neuropathy such as IgM polyneuropathies or IgM-mediated neuropathy, and autoimmune or immune-mediated thrombocytopenia such as idiopathic thrombocytopenic purpura (ITP) including chronic or acute ITP, scleritis such as idiopathic cerato-scleritis, episcleritis, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, lupoid hepatitis, giant-cell hepatitis, autoimmune chronic active hepatitis, lymphoid interstitial pneumonitis (LIP), bronchiolitis obliterans (non-transplant) vs NSIP, Guillain-Barre syndrome, Berger's disease (IgA nephropathy), idiopathic IgA nephropathy, linear IgA dermatosis, acute febrile neutrophilic dermatosis, subcorneal pustular dermatosis, transient acantholytic dermatosis, cirrhosis such as primary biliary cirrhosis and pneumonocirrhosis, autoimmune enteropathy syndrome, Celiac or Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, polychondritis such as refractory or relapsed or relapsing polychondritis, pulmonary alveolar proteinosis, Cogan's syndrome/nonsyphilitic interstitial keratitis, Bell's palsy, Sweet's disease/syndrome, rosacea autoimmune, zoster-associated pain, amyloidosis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies including channelopathies of the CNS, autism, inflammatory myopathy, focal or segmental or focal segmental glomerulosclerosis (FSGS), endocrine opthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases and chronic inflammatory demyelinating polyneuropathy, Dressler's syndrome, alopecia areata, alopecia totalis, CREST syndrome (calcinosis, Raynaud's phenomenon, esophageal dysmotility, sclerodactyly, and telangiectasia), male and female autoimmune infertility, e.g., due to anti-spermatozoan antibodies, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, Sampter's syndrome, Caplan's syndrome, endocarditis, endomyocardial fibrosis, diffuse interstitial pulmonary fibrosis, interstitial lung fibrosis, pulmonary fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, cyclitis such as chronic cyclitis, heterochronic cyclitis, iridocyclitis (acute or chronic), or Fuch's cyclitis, Henoch-Schonlein purpura, SCID, sepsis, endotoxemia, post-vaccination syndromes, Evan's syndrome, autoimmune gonadal failure, Sydenham's chorea, post-streptococcal nephritis, thromboangitis ubiterans, thyrotoxicosis, tabes dorsalis, chorioiditis, giant-cell polymyalgia, chronic hypersensitivity pneumonitis, keratoconjunctivitis sicca, idiopathic nephritic syndrome, minimal change nephropathy, benign familial and ischemia-reperfusion injury, transplant organ reperfusion, retinal autoimmunity, aphthae, aphthous stomatitis, arteriosclerotic disorders, aspermiogenesis, autoimmune hemolysis, Boeck's disease, enteritis allergica, erythema nodosum leprosum, idiopathic facial paralysis, chronic fatigue syndrome, febris rheumatica, Hamman-Rich's disease, sensoneural hearing loss, ileitis regionalis, leucopenia, transverse myelitis, primary idiopathic myxedema, ophthalmia symphatica, polyradiculitis acuta, pyoderma gangrenosum, acquired spenic atrophy, vitiligo, toxic-shock syndrome, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, rheumatic diseases, mixed connective tissue disease, nephrotic syndrome, insulitis, polyendocrine failure, autoimmune polyglandular syndrome type I, adult-onset idiopathic hypoparathyroidism (AOIH), myocarditis, nephrotic syndrome, primary sclerosing cholangitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, granulomas containing eosinophils, seronegative spondyloarthritides, polyendocrine autoimmune disease, sclerosing cholangitis, sclera, episclera, Bruton's syndrome, transient hypogammaglobulinemia of infancy, Wiskott-Aldrich syndrome, ataxia telangiectasia syndrome, angiectasis, autoimmune disorders associated with collagen disease, rheumatism, allergic hypersensitivity disorders, glomerulonephritides, reperfusion injury, ischemic reperfusion disorder, lymphomatous tracheobronchitis, inflammatory dermatoses, dermatoses with acute inflammatory components, and autoimmune uveoretinitis (AUR).

In another embodiment of the above described methods, the method further comprises identifying a subject who is at risk of developing T1D, so as to prevent or delay onset of diabetes symptoms. For example, an individual who has detectable amount of self-autoantibodies associated with T1D that is known in the art. See the risk factors and markers described by Ping Xu and Jeffrey P. Krischer in "Prognostic classification factors associated with development of multiple autoantibodies, dysglycemia, and Type 1 Diabetes—A recursive partitioning analysis" in Diabetes Care, 2016, 39(6): 1036-1044.

In one embodiment of any one of the method described, the autoimmune disorder is Type 1 diabetes (T1D).

In one embodiment of any one of the method described, the subject has been newly diagnosed with T1D.

In one embodiment of any one of the method described, the subject has been newly been detected to have self-autoantibodies associated with T1D, e.g., GAD65 autoantibody, and islet antigen 2 autoantibody.

In one embodiment of any one of the method described, the HSCs are autologous to the recipient subject.

In one embodiment of any one of the method described, the HSCs are non-autologous and allogenic to the recipient subject.

In one embodiment of any one of the method described, the HSCs are non-autologous and xenogeneic to the recipient subject.

In one embodiment of any one of the method described, the population of HSCs is obtained from the bone marrow, umbilical cord, amniotic fluid, chorionic villi, cord blood, placental blood or peripheral blood.

In one embodiment of any one of the method described, the population of HSCs is obtained from mobilized peripheral blood.

In one embodiment of any one of the method described, the population of HSCs comprises $CD34^+$ cells. In another embodiment, the population of HSCs comprises $CD34^+$ selected cells obtained from the bone marrow, umbilical cord, amniotic fluid, chorionic villi, cord blood, placental blood or peripheral blood or mobilized peripheral blood.

In one embodiment of any one of the method described, the population of HSCs is autologous to the recipient subject.

In one embodiment of any one of the method described, the population of HSCs is at the minimum HLA type matched to the recipient subject.

In one embodiment of any one of the method described, the population of HSCs are cryopreserved after the removal of excess $PGE_2$ or after post-transfection with the vector, ex vivo cultured to expand the population of modified HSCs, prior to transplantation into the recipient subject.

In other embodiments of the compositions and methods described herein, the HSCs can be ex vivo culture expanded any time to increase the number of starting HSCs for transduction with a vector described herein or stimulation with $PGE_2$ or for use in therapy. For example, ex vivo culture cell expansion can take place after harvesting from a donor subject, after transduction with the vector described herein, after contact with $PGE_2$, after any cryopreservation step described herein.

In other embodiments of the compositions and methods described herein, cryopreservation of the HSCs can take place any time after harvesting from a donor subject, after culture expansion following harvesting from a donor subject, after transduction with the vector described herein, after contact with $PGE_2$, after the removal of excess $PGE_2$, after culture expansion following transduction with the vector described herein or after contact with $PGE_2$.

In one embodiment of any one of the method described, the population of HSCs are ex vivo culture expanded after the removal of excess $PGE_2$ or after post-transfection with the vector, prior to transplantation into the recipient subject.

In one embodiment of any one of method described herein, after the contacting, the HSC is cryopreserved prior to use, for example, ex vivo expansion and/or implantation into a subject.

In one embodiment of any one of the method described herein, after the contacting, the HSC is culture expanded ex vivo prior to use, for example, cryopreservation, and/or implantation/engraftment into a subject.

In one embodiment of any one of the method described, the method further comprises identifying a subject afflicted with an autoimmune disease or disorder or an individual who is an organ or bone marrow transplant recipient.

In another embodiment of any one of the method described, the method further comprises selecting a subject having an autoimmune disease or disorder or an individual who is an organ or bone marrow transplant recipient.

In one embodiment of any one of the method described, the method further comprises selecting a recipient subject in need of immune response modulation. Such as an individual who is an organ or bone marrow transplant recipient who has received an allogenic graft.

In another embodiment of any one of the method described, the method further comprises identifying a subject in need of immune response suppression. Such as an individual who is an organ or bone marrow transplant recipient who has received an allogenic graft.

In another embodiment of any one of the method described, the method further comprises selecting a subject in need of immune response suppression. Such as an individual who is an organ or bone marrow transplant recipient who has received an allogenic graft.

In one embodiment of any one of the method described, the method further comprises allowing the population of $PD-L1^+$ expressing HSCs to differentiate in vivo into $PD-L1^+$ expressing progeny cells.

In one embodiment of any one of the method described herein, after the contacting, the HSC is differentiated in culture ex vivo prior to use, for example, cryopreservation, and/or implantation/engraftment into a subject.

In one embodiment of any one of the therapeutic method described herein, the chemotherapy and/or radiation is to reduce endogenous stem cells to facilitate engraftment and/or reconstitution of the implanted cells.

In one aspect of of any one of the method described herein, the PD-L1 expressing HSCs or progeny cells thereof are further treated ex vivo with prostaglandin E2 and/or antioxidant N-acetyl-L-cysteine (NAC) to promote subsequent engraftment and/or reconstitution of the cells when implanted in a recipient subject.

In one embodiment of any one of the method described, the method further comprises administering an additional immunosuppression therapy to the subject.

In one embodiment of any one of the method described, the additional immunosuppression therapy comprises thymoglobulin, cyclophosphamide, or both thymoglobulin plus cyclophosphamide.

In one embodiment of any one of the method described, the additional immunosuppression therapy comprises anti-thymocyte antigens (ATG), or CTLA4-fusion immunoglobulins, or both.

In some embodiments, non-limiting examples of additional immunosuppression therapy are calcineurin inhibitors (such as cyclosporine, voclosporin and tacrolimus); CD80/86:CD28 costimulation inhibitors (CTLA4-fusion immunoglobulins such as abatacept and belatacept); CD154:CD40 costimulation inhibitors (anti-CD40 monoclonal antibodies such as ASKP1240; Astellas); CD20 inhibitors (anti-CD20 antibodies such as rituximab, ocrelizumab, ofatumumab, and veltuzumab); CD22 inhibitors (anti-CD22 antibodies such as epratuzumab); B cell differentiation inhibitors (such as belimumab and atacicept); antibody-producing plasma cell inhibitors (such as bortezomib); inhibitor of the complement process (such as eculizumab); inhibitors of cytokines that are involved in the immune response with the T or B cells (such as steroids e.g. dexamethasome, glucocorticoid and corticosteroid; Janus kinase inhibitor e.g. tofacitinib; IL-6 receptor inhibitor, e.g. basiliximab; TNF inhibitors e.g. infliximab, adalimumab, golimumab, and certolizumab; IL-1 inhibitors e g anikinra, rilonacept, and canakinumab; and IL-17 inhibitor e.g. secukinumab); inhibitors of chemokines and cell adhesion (such as CCR5 receptor antagonist maraviroc, CXCR4 antagonist plerixafor, CCR4 humanized mAb mogamulizumab, and CCL2 (also known as monocyte chemotactic protein 1) inhibitor emapticap; pooled intravenous immunoglobulins (IVIG) from from several thousand plasma donors; polyclonal antithymocyte globulin(ALG) and antithymocyte antigens (ATG); CD52 inhibitors (anti-CD25 e.g. alemtuzumab); mTOR inhibitors (e.g., rapamycin, sirolimus and everolimus); and other antimetabolites such as DNA synthesis inhibitor e.g., azathioprine (AZA), mycophenolate, leflunomide, and cytotoxic agents such as cyclophosphamide.

Lentiviral vectors of the disclosure include, but are not limited to, human immunodeficiency virus (e.g., HIV-1, HIV-2), feline immunodeficiency virus (FIV), simian immunodeficiency virus (SIV), bovine immunodeficiency virus (BIV), and equine infectious anemia virus (EIAV). These vectors can be constructed and engineered using art-recognized techniques to increase their safety for use in therapy and to include suitable expression elements and therapeutic genes, such as described above.

In consideration of the potential toxicity of virus-based vectors, the vectors can be designed in different ways to increase their safety in gene therapy applications. For example, the vector can be made safer by separating the necessary lentiviral genes (e.g., gag and pol) onto separate vectors as described, for example, in U.S. Pat. No. 6,365, 150, the contents of which are incorporated by reference herein. Thus, recombinant retrovirus can be constructed such that the retroviral coding sequence (gag, pol, env) is replaced by a gene of interest rendering the retrovirus replication defective. The replication defective retrovirus is then packaged into virions through the use of a helper virus or a packaging cell line, by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals.

A major prerequisite for the use of viruses as gene delivery vectors is to ensure the safety of their use, particularly with regard to the possibility of the spread of wild-type virus in the cell population. The development packaging cell lines, which produce only replication-defective retroviruses, has increased the utility of retroviruses for gene therapy, and defective retroviruses are well characterized for use in gene transfer for gene therapy purposes (for a review see Miller, A. D. (1990) Blood 76:271). Accordingly, in one embodiment of the disclosure, packaging cell lines are used to propagate vectors (e.g., lentiviral vectors) of the disclosure to increase the titer of the vector virus. The use of packaging cell lines is also considered a safe way to propagate the virus, as use of the system reduces the likelihood that recombination will occur to generate wild-type virus. In addition, to reduce toxicity to cells that caused by expression of packaging proteins, packaging systems can be use in which the plasmids encoding the packaging functions of the virus are only transiently transfected by, for example, chemical means.

In another embodiment, the vector can be made safer by replacing certain lentiviral sequences with non-lentiviral sequences. Thus, lentiviral vectors of the present disclosure may contain partial (e.g., split) gene lentiviral sequences and/or non-lentiviral sequences (e.g., sequences from other retroviruses) as long as its function (e.g., viral titer, infectivity, integration and ability to confer high levels and duration of therapeutic gene expression) are not substantially reduced. Elements which may be cloned into the viral vector include, but are not limited to, promoter, packaging signal, LTR(s), polypurine tracts, and a reverse response element (RRE).

In one embodiment of the disclosure, the LTR region is modified by replacing the viral LTR promoter with a heterologous promoter. In one embodiment, the promoter of the 5' LTR is replaced with a heterologous promoter. Examples of heterologous promoters which can be used include, but are not limited to, a spleen focus-forming virus (SFFV) promoter, a tetracycline-inducible (TET) promoter, ar3-globin locus control region and β-globin promoter (LCR), and a cytomegalovirus (CMV) promoter. In some embodiments, the promoter is a regulatable promoter, an inducible promoter, for the regulating the production of PD-L1. For example, a Tetracyclin-inducible or Doxycyclin-inducible promoter.

In some embodiments, the viral vectors such as lentiviral vector or AAV or avian viral vectors of the disclosure also include vectors which have been modified to improve upon safety in the use of the vectors as gene delivery agents in gene therapy. In one embodiment of this disclosure, an LTR region, such as the 3' LTR, of the vector is modified in the U3 and/or U5 regions, wherein a SIN vector is created. Such modifications contribute to an increase in the safety of the vector for gene delivery purposes. In one embodiment, the vector comprises a deletion in the 3' LTR wherein a portion of the U3 region is replaced with an insulator element. The insulator prevents the enhancer/promoter sequences within the vector from influencing the expression of genes in the nearby genome, and vice/versa, to prevent the nearby genomic sequences from influencing the expression of the genes within the vector. In a further embodiment of this disclosure, the 3' LTR is modified such that the U5 region is replaced, for example, with an ideal poly(A) sequence. It should be noted that modifications to the LTRs such as modifications to the 3' LTR, the 5' LTR, or both 3' and 5' LTRs, are also included in the disclosure.

The promoter of the lentiviral vector can be one which is naturally (i.e., as it occurs with a cell in vivo) or non-naturally associated with the 5' flanking region of a particular gene. Promoters can be derived from eukaryotic genomes, viral genomes, or synthetic sequences. Promoters can be selected to be non-specific (active in all tissues) (e.g., SFFV), tissue specific (e.g., (LCR), regulated by natural regulatory processes, regulated by exogenously applied drugs (e.g., TET), or regulated by specific physiological states such as those promoters which are activated during an acute phase response or those which are activated only in replicating cells. Non-limiting examples of promoters in the present disclosure include the spleen focus-forming virus promoter, a tetracycline-inducible promoter, a β-globin locus control region and a β-globin promoter (LCR), a cytomegalovirus (CMV) promoter, retroviral LTR promoter, cytomegalovirus immediate early promoter, SV40 promoter, and dihydrofolate reductase promoter. The promoter can also be selected from those shown to specifically express in the select cell types such as HSCs and their progenies. In one embodiment, the promoter of the vecter is cell specific such that gene expression is restricted to red blood cells. Erythrocyte-specific expression is achieved by using the human β-globin promoter region and locus control region (LCR).

Skilled practitioners will recognize that selection of the promoter to express the polynucleotide of interest will depend on the vector, the nucleic acid cassette, the cell type to be targeted, and the desired biological effect. Skilled practitioners will also recognize that in the selection of a promoter, the parameters can include: achieving sufficiently high levels of gene expression to achieve a physiological effect; maintaining a critical level of gene expression; achieving temporal regulation of gene expression; achieving cell type specific expression; achieving pharmacological, endocrine, paracrine, or autocrine regulation of gene expression; and preventing inappropriate or undesirable levels of expression. Any given set of selection requirements will depend on the conditions but can be readily determined once the specific requirements are determined. In one embodiment of this disclosure, the promoter is cell-specific such that gene expression is restricted to red blood cells. Erythrocyte-specific expression is achieved by using the human β-globin promoter region and locus control region (LCR).

Standard techniques for the construction of expression vectors suitable for use in the present disclosure are well-known to those of ordinary skill in the art and can be found in such publications as Michael R. Green and Joseph Sambrook, Molecular Cloning: A Laboratory Manual, Cold Spring Harbor Laboratory Press, Cold Spring Harbor, N.Y., USA (2012). A variety of strategies are available for ligating fragments of DNA, the choice of which depends on the nature of the termini of the DNA fragments and which choices can be readily made by the skilled artisan.

The step of facilitating the production of infectious viral particles in the cells may be carried out using conventional techniques, such as standard cell culture growth techniques. If desired by the skilled practitioner, lentiviral stock solutions may be prepared using the vectors and methods of the present disclosure. Methods of preparing viral stock solutions are known in the art and are illustrated by, e.g., Y. Soneoka et al. (1995) Nucl. Acids Res. 23:628-633, and N. R. Landau et al. (1992) J. Virol. 66:5110-5113. In the method of producing a stock solution in the present disclosure, lentiviral-permissive cells (referred to herein as producer cells) are transfected with the vector system of the present disclosure. The cells are then grown under suitable cell culture conditions, and the lentiviral particles collected from either the cells themselves or from the cell media as described above. Suitable producer cell lines include, but are not limited to, the human embryonic kidney cell line 293, the equine dermis cell line NBL-6, and the canine fetal thymus cell line Cf2TH.

The step of collecting the infectious virus particles also can be carried out using conventional techniques. For example, the infectious particles can be collected by cell lysis, or collection of the supernatant of the cell culture, as is known in the art. Optionally, the collected virus particles may be purified if desired. Suitable purification techniques are well known to those skilled in the art.

Other methods relating to the use of viral vectors in gene therapy can be found in, e.g., Kay, M. A. (1997) Chest 111(6 Supp.):138S-142S; Ferry, N. and Heard, J. M. (1998) Hum. Gene Ther. 9:1975-81; Shiratory, Y. et al. (1999) Liver 19:265-74; Oka, K. et al. (2000) Curr. Opin. Lipidol. 11:179-86; Thule, P. M. and Liu, J. M. (2000) Gene Ther. 7:1744-52; Yang, N. S. (1992) Crit. Rev. Biotechnol. 12:335-56; Alt, M. (1995) J. Hepatol. 23:746-58; Brody, S. L. and Crystal, R. G. (1994) Ann. N.Y. Acad. Sci. 716:90-101; Strayer, D. S. (1999) Expert Opin. Investig. Drugs 8:2159-2172; Smith-Arica, J. R. and Bartlett, J. S. (2001) Curr. Cardiol. Rep. 3:43-49; and Lee, H. C. et al. (2000) Nature 408:483-8.

In one embodiment, the sample of HSCs is contacted with at least $10^3$ vectors or viral vectors or particles per $10^6$ HSC cells in the ex vivo transfection or transduction procedure. The vector carries an exogenous copy of a nucleic acid encoding a PD-L1. Other vector dosage ranges set forth herein for contacting with the sample of HSCs is exemplary only and are not intended to limit the scope or practice of the claimed composition or methods described herein. In one embodiment, the vector dosage is ranges from $10^3$-$10^8$ viral particles/$10^6$ HSC cells. In other embodiments, the vector dosage is ranges from $10^3$-$10^5$ viral particles/$10^6$ HSC cells, $10^4$-$10^6$ viral particles/$10^6$ HSC cells, $10^5$-$10^7$ viral particles/$10^6$ HSC cells, $10^3$-$10^8$ viral particles/$10^6$ HSC cells. In one embodiment, the dosage is about $10^4$ viral particles/$10^6$ HSC cells.

The retroviral or lentiviral vectors, or avian viral vector or adeno-associated viral vectors are ex vivo contacted with the HSCs using standard transfection techniques well known in the art.

In one embodiment, the retroviral or lentiviral vectors or avian viral vector or adeno-associated viral vectors are transduced into HSCs, hematopoietic progenitor cells or precursors of erythrocytes.

Another aspect of the disclosure pertains to compositions comprising the vectors described. In one embodiment, the composition includes a lentiviral vector or avian viral vector or adeno-associated viral vectors in an effective amount sufficient to transduce a sample of HSCs and a pharmaceutically acceptable carrier. An "effective amount" with respect to vector transduction refers to an amount effective, at dosages and for periods of time necessary, to achieve the desired result of introducing the exogenous PD-L1 encoding nucleic acid into HSCs. An effective amount of viral vector may vary according to factors such as the disease state, age, sex, and weight of the donor individual, and the ability of the viral vector to elicit a desired response in the transduced HSCs. Dosage regimens may be adjusted to provide the optimum response. An effective amount is also one in which any toxic or detrimental effects of the viral vector are outweighed by the beneficial effects. The potential toxicity of the viral vectors of the disclosure can be assayed using cell-based assays or art recognized animal models and an effective modulator can be selected which does not exhibit significant toxicity.

Sterile solutions can be prepared by incorporating lentiviral vector in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile solutions, the preferred methods of preparation are vacuum drying and freeze-drying which yields a powder of the active ingredient plus any additional desired ingredient from a previously sterile-filtered solution thereof.

In some embodiments, the PD-L1$^+$ HSC cells or compositions comprising the PD-L1$^+$ HSC cells are sterile and are formulated for therapy in a subject. In one embodiment, the subject is a mammal, e.g., a human.

In some embodiments, the PD-L1$^+$ HSC cells or compositions comprising the PD-L1$^+$ HSC cells comprise serum or plasma. Alternatively, the compositions comprise a cryopreservative, e.g., DMSO.

In some embodiments, the compositions or pharmaceutical compositions are formulated for systemic delivery. In some embodiments, the compositions can be formulated for delivery to specific organs, for example but not limited to the liver, spleen, the bone marrow, and the skin. Pharmaceutical compositions comprise pharmaceutically acceptable carrier.

In addition, the compositions or pharmaceutical compositions described herein can be administered together with other components of biologically active agents, such as pharmaceutically acceptable surfactants (e.g., glycerides), excipients (e.g., lactose), carriers, serum, plasma, diluents and vehicles.

In some embodiments, the compositions or pharmaceutical compositions described herein contain about $1\times10^6$ cells to about $3\times10^6$ cells; about $1.0\times10^6$ cells to about $5\times10^6$ cells; about $1.0\times10^6$ cells to about $10\times10^6$ cells, about $10\times10^6$ cells to about $20\times10^6$ cells, about $10\times10^6$ cells to about $30\times10^6$ cells, or about $20\times10^6$ cells to about $30\times10^6$ PD-L1 expressing cells or HSCs or their progeny.

In some embodiments, the compositions or pharmaceutical compositions described herein contain about $1\times10^6$ cells to about $30\times10^6$ cells; about $1.0\times10^6$ cells to about $20\times10^6$ cells; about $1.0\times10^6$ cells to about $10\times10^6$ cells, about $2.0\times10^6$ cells to about $30\times10^6$ cells, about $2.0\times10^6$ cells to about $20\times10^6$ cells, or about $2.0\times10^6$ cells to about $10\times10^6$ PD-L1 expressing cells or HSCs or their progeny.

In some embodiments, the compositions or pharmaceutical compositions described herein contain about $1\times10^6$ hematopoietic stem or progenitor cells, about $2\times10^6$ cells, about $5\times10^6$ cells, about $7\times10^6$ cells, about $10\times10^6$ cells, about $15\times10^6$ cells, about $17\times10^6$ cells, about $20\times10^6$ cells about $25\times10^6$ cells, or about $30\times10^6$ PD-L1 expressing cells or HSCs or their progeny.

The dosage of PD-L1+ HSC cells administered to a recipient subject will vary depending upon a variety of factors, including the number of PD-L1+ HSCs available, the level of expression of PD-L1 in the HSCs, route of administration, size, age, sex, health, body weight and diet of the recipient; nature and extent of symptoms of the disease being treated, kind of concurrent treatment, frequency of treatment, and the effect desired.

In one embodiment, the dosage of PD-L1 expressing HSCs should be large enough a cell population transplanted to ensure sufficient engraftment and reconstitution in vivo after implantation into the subject.

In one embodiment, the dosage is at least $1\times10^4$ cells per implantation. In other embodiments, the dosage is at least $5\times10^4$ cells, at least $1\times10^5$ cells, at least $5\times10^5$ cells, at least $1\times10^6$ cells, at least $5\times10^6$ cells, at least $1\times10^7$ cells, at least $5\times10^7$ cells, at least $1\times10^8$ cells, at least $5\times10^8$ cells, at least $1\times10^9$ cells, at least $5\times10^9$ cells, or at least $1\times10^{10}$ cells or more per implantation into a subject. Second or subsequent administrations can be administered at a dosage which is the same, less than or greater than the initial or previous dose administered to the individual.

In some embodiments, the dosage of PD-L1+ HSC cells administered to a recipient subject is about at least $0.1\times10^5$ cells/kg of bodyweight, at least $0.5\times10^5$ cells/kg of bodyweight, at least $1\times10^5$ cells/kg of bodyweight, at least $5\times10^5$ cells/kg of bodyweight, at least $10\times10^5$ cells/kg of bodyweight, at least $0.5\times10^6$ cells/kg of bodyweight, at least $0.75\times10^6$ cells/kg of bodyweight, at least $1\times10^6$ cells/kg of bodyweight, at least $1.25\times10^6$ cells/kg of bodyweight, at least $1.5\times10^6$ cells/kg of bodyweight, at least $1.75\times10^6$ cells/kg of bodyweight, at least $2\times10^6$ cells/kg of bodyweight, at least $2.5\times10^6$ cells/kg of bodyweight, at least $3\times10^6$ cells/kg of bodyweight, at least $4\times10^6$ cells/kg of bodyweight, at least $5\times10^6$ cells/kg of bodyweight, at least $10\times10^6$ cells/kg of bodyweight, at least $15\times10^6$ cells/kg of bodyweight, at least $20\times10^6$ cells/kg of bodyweight, at least $25\times10^6$ cells/kg of bodyweight, or at least $30\times10^6$ cells/kg of bodyweight of the subject recipient.

In another embodiment, the dosage is at least $2\times10^6$ cells/kg bodyweight of the recipient subject. In other embodiments, the dosage is at least $3\times10^6$ cells/kg of bodyweight, at least $4\times10^6$ cells/kg of bodyweight, at least $5\times10^6$ cells/kg of bodyweight, at least $6\times10^6$ cells/kg of bodyweight, at least $7\times10^6$ cells/kg of bodyweight, at least $8\times10^6$ cells/kg of bodyweight, at least $9\times10^6$ cells/kg of bodyweight, at least $10\times10^6$ cells/kg of bodyweight, at least $15\times10^6$ cells/kg of bodyweight, at least $20\times10^6$ cells/kg of bodyweight, at least $25\times10^6$ cells/kg of bodyweight, or at least $30\times10^6$ cells/kg of bodyweight of the subject recipient.

In another embodiment, the dosage is at least greater than $5\times10^6$ cells/kg bodyweight of the recipient subject.

In another embodiment, the dosage is at least greater than $10\times10^6$ cells/kg bodyweight of the recipient subject.

A second or subsequent administration is preferred. For example, second and subsequent administrations can be given between about one day to 30 weeks from the previous administration. Two, three, four or more total administrations can be delivered to the individual, as needed.

The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

Efficacy testing can be performed during the course of treatment using the methods described herein. Measurements of the degree of severity of a number of symptoms associated with a particular ailment are noted prior to the start of a treatment and then at later specific time period after the start of the treatment. For example, the amount of insulin in the blood or blood glucose after a meal.

The present disclosure can be defined in any of the following numbered paragraphs:

[1] A population of modified HSCs where the cells carry an exogenous copy of a nucleic acid encoding a PD-L1.

[2] The population of modified HSCs of paragraph 1, wherein the cells are expressing PD-L1.

[3] The population of modified HSCs of paragraph 1 or 2, wherein the nucleic acid is a cDNA.

[4] The population of modified HSCs of paragraph 1 or 2, wherein the nucleic acid is a genomic DNA.

[5] The population of modified HSCs of paragraph 4, wherein the nucleic acid is integrated into the genome of the cells.

[6] The population of modified HSCs of any one of the preceding paragraphs, wherein the nucleic acid is introduced into the cells via a vector.

[7] The population of modified HSCs of paragraph 6, wherein the vector is a viral vector.

[8] The population of modified HSCs of paragraph 7, wherein the viral vector is a lentiviral vector.

[9] The population of modified HSCs of any one of the preceding paragraphs, wherein the cells are mammalian cells.

[10] The population of modified HSCs of paragraph 9, wherein the mammalian cells are human cells.

[11] The population of modified HSCs of any one of the preceding paragraphs, wherein prior to the modification, the HSCs are obtained from the bone marrow, umbilical cord, amniotic fluid, chorionic villi, cord blood, placental blood or peripheral blood.

[12] The population of modified HSCs of paragraph 11, wherein the HSCs are obtained from mobilized peripheral blood.

[13] The population of modified HSCs of any one of the preceding paragraphs, wherein the HSCs are derived from a healthy individual.

[14] The population of modified HSCs of any one of the preceding paragraphs, wherein the HSCs are derived from an individual with a diagnosed disease or disorder.

[15] The population of modified HSCs of paragraph 14, wherein the diagnosed disease or disorder is an autoimmune disease or disorder.

[16] The population of modified HSCs of paragraph 15, wherein the autoimmune disease or disorder is Type 1 diabetes (T1D).

[17] The population of modified HSCs of any one of the preceding paragraphs, wherein the cells are ex vivo cultured before or after or both before and after the introduction of the exogenous copy of a nucleic acid encoding a PD-L1.

[18] The population of modified HSCs of any one of the preceding paragraphs, wherein the cells are cryopreserved prior to or after or both before and after the introduction of the exogenous copy of a nucleic acid encoding a PD-L1.

[19] The population of modified HSCs of any one of the preceding paragraphs, wherein the cells are cryopreserved prior to use.

[20] The population of modified HSCs of any one of the preceding paragraphs, wherein the cells are produced by a method comprising: (a) contacting a sample of HSCs with a vector carrying an exogenous copy of a nucleic acid encoding a PD-L1 to modify the HSCs; ex vivo culturing the resultant modified cells from the contacting; and (c) establishing the expression of PD-L1 on the modified HSCs, thereby producing a population of modified HSCs cells expressing PD L1.

[21] The population of modified HSCs of paragraph 20, wherein the method further comprises establishing that there is at least one fold increase in the number of PD-L1+ expressing cells compared to non-modified cells.

[22] An ex vivo method of producing a population of modified, PD-L1+ expressing HSCs, the method comprising: (a) contacting a sample of HSCs with a vector carrying an exogenous copy of a nucleic acid encoding a PD-L1 to modify the HSCs whereby the exogenous copy of a nucleic acid is introduced into the HSCs; (b) ex vivo culturing the resultant modified cells from the contacting; and (c) establishing the expression of PD-L1 on the modified HSCs, thereby producing a population of modified HSCs cells expressing PD-L1.

[23] The ex vivo method of paragraph 22, wherein the method further comprises establishing that there is at least one fold increase in the number of PD-L1+ expressing cells compared to non-modified cells.

[24] The ex vivo method of paragraph 22 or 23, wherein the sample of HSC is obtained from the bone marrow, umbilical cord, amniotic fluid, chorionic villi, cord blood, placental blood or peripheral blood.

[25] The ex vivo method of paragraph 24, wherein the sample of HSC is obtained from mobilized peripheral blood.

[26] The ex vivo method of any one of the preceding paragraphs, wherein the sample of HSCs is obtained from a healthy individual.

[27] The ex vivo method of any one of the preceding paragraphs, wherein the sample of HSCs is obtained from an individual with a diagnosed disease or disorder.

[28] The ex vivo method of paragraph 27, wherein the diagnosed disease or disorder is an autoimmune disease or disorder.

[29] The ex vivo method of paragraph 28, wherein the autoimmune disease or disorder is Type 1 diabetes (T1D).

[30] The ex vivo method of any one of the preceding paragraphs, wherein the vector is viral vector.

[31] The ex vivo method of paragraph 30, wherein the viral vector is a lentiviral vector, an avian virus vector or an adeno-associated virus.

[32] The ex vivo method of any one of the preceding paragraphs, wherein the nucleic acid is a cDNA.

[33] The ex vivo method of any one of the preceding paragraphs, wherein the nucleic acid is a genomic DNA.

[34] The ex vivo method of paragraph 33, wherein the nucleic acid is integrated into the genome of the cells.

[35] A composition comprising the hematopoietic stem cells of any one of the preceding paragraphs or hematopoietic stem cells produced by any one of the preceding method paragraphs.

[36] A composition for transplantation into a subject or for reducing an immune response in a subject, the composition comprising the hematopoietic stem cells of any one of the preceding paragraphs or the hematopoietic stem cells produced by the method of one of the preceding paragraphs.

[37] A method of treating an autoimmune disorder in a subject in need thereof, the method comprising administering to a subject a composition comprising the hematopoietic stem cells in any one of the preceding paragraphs.

[38] The method of paragraph 37, wherein the autoimmune disorder is T1D.

[39] The method of paragraph 37 or 38, wherein the HSCs are autologous to the recipient subject.

[40] The method of paragraph 37 or 38, wherein the HSCs are non-autologous and allogenic to the recipient subject.

[41] The method of paragraph 37 or 38, wherein the HSCs are non-autologous and xenogeneic to the recipient subject.

[42] A method of modulating an immune response in a subject comprising: (a) providing a population of HSCs; (b) contacting sample of HSCs with prostaglandin $E_2$ ($PGE_2$) at 0.1 M concentration for at least 24 hrs at 37° C.; (c) removing the $PGE_2$ after 24 hrs, thereby producing a population of PD-L1+ expressing HSCs; (d) transplanting said population of PD-L1+ expressing HSCs into a recipient subject, thereby modulating the immune response in the recipient subject.

[43] A method of modulating an immune response in a subject comprising: (a) providing a population of HSCs; (b) contacting sample of HSCs with a vector carrying an exogenous copy of a nucleic acid encoding a PD-L1; (c) ex vivo culturing the resultant modified cells from the contacting; (d) establishing the expression of PD-L1 on the modified HSCs, thereby producing a population of modified HSCs cells expressing PD-L1; and (e) transplanting said population of PD-L1+ expressing HSCs into a recipient subject, thereby modulating the immune response in the recipient subject.

[44] The method of paragraph 42 or 43, wherein the population of HSCs is obtained from the bone marrow, umbilical cord, amniotic fluid, chorionic villi, cord blood, placental blood or peripheral blood.

[45] The method of paragraph 44, wherein the population of HSCs is obtained from mobilized peripheral blood.

[46] The method of any one of the preceding paragraphs, wherein the population of HSCs autologous to the recipient subject.

[47] The method of any one of the preceding paragraphs, wherein the population of HSCs allogeneic to the recipient subject.

[48] The method of any one of the preceding paragraphs, wherein the population of HSCs is xenogeneic to the recipient subject.

[49] The method of any one of the preceding paragraphs, wherein the population of HSCs are cryopreserved after the removal of $PGE_2$ or after ex vivo culturing post-transfection with a vector prior to transplantation into the recipient subject.

[50] The method of claim any one of the preceding paragraphs, wherein the population of HSCs are culture expanded ex vivo after the removal of $PGE_2$ or after ex vivo culturing post-transfection with a vector prior to transplantation into the recipient subject.

[51] The method of claim any one of the preceding paragraphs, the method further comprising selecting a recipient subject in need of immune response modulation.

[52] A composition comprising the PD-L1 expressing hematopoietic stem cells of any one of paragraphs 1-21 or hematopoietic stem cells produced by any one of the method paragraphs 22-34 for use in the prevention or treatment of an autoimmune disease or disorder, for use in suppressing an immune response in a subject, for use in the delay of the onset of T1D in a subject at risk of developing T1D, for use in the prevention and delay of an allogenic tissue or organ transplant rejection, and for the treatment of T1D in adult and pediatric subjects.

[53] A composition comprising the PD-L1 expressing hematopoietic stem cells of any one of paragraphs 1-21 or hematopoietic stem cells produced by any one of the method paragraphs 22-34 for the manufacture of medicament for use in the prevention or treatment of an autoimmune disease or disorder, in the suppression of an immune response in a subject, in the delay of the onset of T1D in a subject at risk of developing T1D, in the prevention and delay of an allogenic tissue or organ transplant rejection, and for the treatment of T1D in adult and pediatric subjects.

[54] A population of PD-L1 expressing hematopoietic stem cells of any one of paragraphs 1-21 or hematopoietic stem cells produced by any one of the method paragraphs 22-34 for use in the prevention or treatment of an autoimmune disease or disorder, for use in suppressing an immune response in a subject, for use in the delay of the onset of T1D in a subject at risk of developing T1D, for use in the prevention and delay of an allogenic tissue or organ transplant rejection, and for the treatment of T1D in adult and pediatric subjects.

[55] A population of PD-L1 expressing hematopoietic stem cells of any one of paragraphs 1-21 or hematopoietic stem cells produced by any one of the method paragraphs 22-34 for for the manufacture of medicament for use in the prevention or treatment of an autoimmune disease or disorder, in the suppression of an immune response in a subject, in the delay of the onset of T1D in a subject at risk of developing T1D, in the prevention and delay of an allogenic tissue or organ transplant rejection, and for the treatment of T1D in adult and pediatric subjects.

The skilled artisan will appreciate that certain factors may influence the dosage and timing required to effectively treat a subject, including but not limited to the severity of the disease or disorder, previous treatments, the general health and/or age of the subject, and other diseases present.

This disclosure is further illustrated by the following example which should not be construed as limiting. The contents of all references cited throughout this application, as well as the figures and table are incorporated herein by reference.

Those skilled in the art will recognize, or be able to ascertain using not more than routine experimentation, many equivalents to the specific embodiments of the disclosure described herein. Such equivalents are intended to be encompassed by the following claims.

EXAMPLES

Example 1

Exemplary HSCs Ex Vivo Culture Protocol with $PGE_2$ for Stimulating PD-L1 Expression.

$CD34^+$ cells were isolated from patients (20 ml of blood) using magnetic beads and ~$1\times10^6$ cells were plated in a U-bottom 96-well plate with 200 µl of the indicated medium. STFIA medium was defined as serum-free medium supplemented with 10 µg/ml heparin, 10 ng/ml human SCF, 20 ng/ml human TPO, 10 ng/ml human FGF-1, 100 ng/ml IGFBP2, and 500 ng/ml Angptl3. $PGE_2$ was added the culture at 0 h, 24 h, 72 h and 6 days. An aliquot of 2 µl of diluted $PGE_2$ at a concentration of 10 µM was added to the 200 µl of each well in the 96-well plate. The approximate final concentration of $PGE_2$ in each well is 0.1 µM. Therefore, the cells are exposed to ~0.1 µM of $PGE_2$. The periodic addition of $PGE_2$ at 24 h, 72 h and 6 days serves to maintain the $PGE_2$ in the culture media. Cells were cultured for 7 days at 37° C. in 5% $CO_2$ and the normal level of $O_2$.

Alternatively, cells are cultured in the same conditions for 48 h in the absence of $PGE_2$, after which and $PGE_2$ is added and then later at 24 h after the initial additional. $PGE_2$ is added to the same approximate final concentration of $PGE_2$ of 0.1 µM. We typically observed a ~10-fold increase of $CD34^+PD-L1^+$ of cells after 8 days of culture when compared with a cell culture with the same medium cultured for the same time in the same conditions with cells obtained from the same subjects but without addition of $PGE_2$.

The percentage of $CD34^+1^3D-L1^+$ cells obtained at day 0 without culturing in healthy subjects is nearly 24%, in individuals with T1D is 8-10%. This protocol produces increased expression of PD-L1 as compared to baseline (at least 5-fold increase).

Example 2

In Vitro Murine Studies—

Figure 2A:
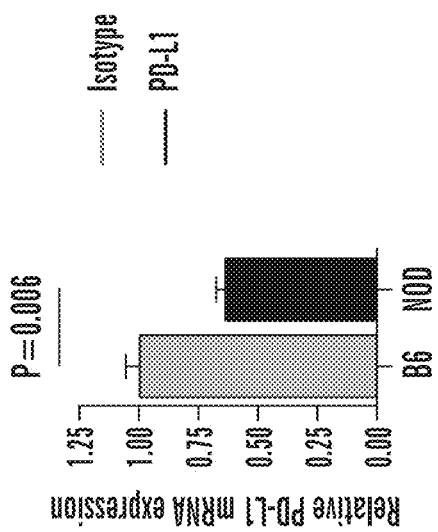
FIGS. 2A and 2B show that the percentage of peripheral PD-L1$^+$ HSCs is reduced in NOD mice compared to B6.
Figure 2B:
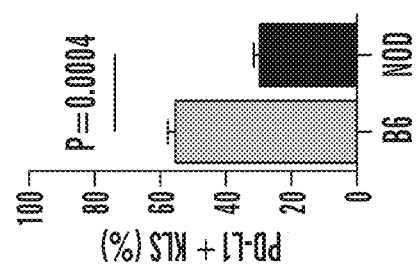
Figure 2C:
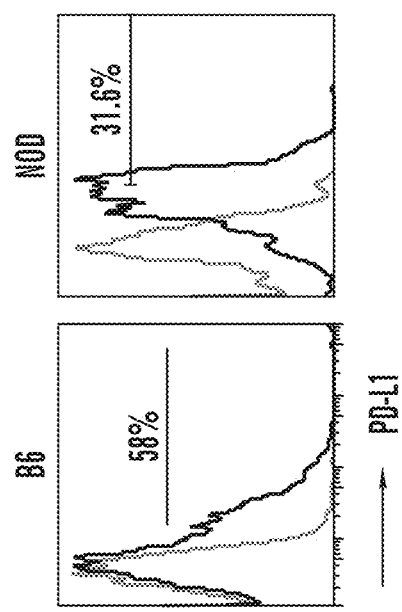
FIG. 2C shows the confirmation of PD-L1 expression defect in NOD mice by PCR.
Figure 2E:
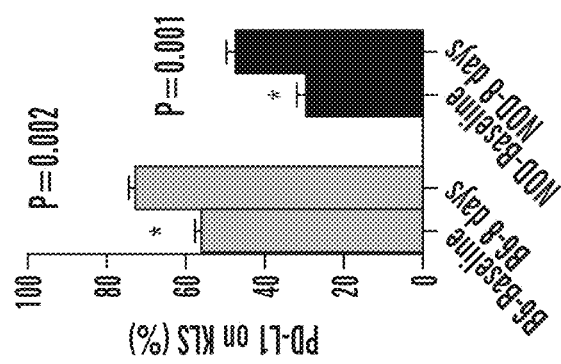
FIGS. 2D and 2E show that the murine PD-L1 defect on HSCs can be overturned in vitro by pharmacologic approach. After 8 days of in vitro culture, an increase in the percentage of PD-L1$^+$ KLS cells was evident.
Figure 2D:
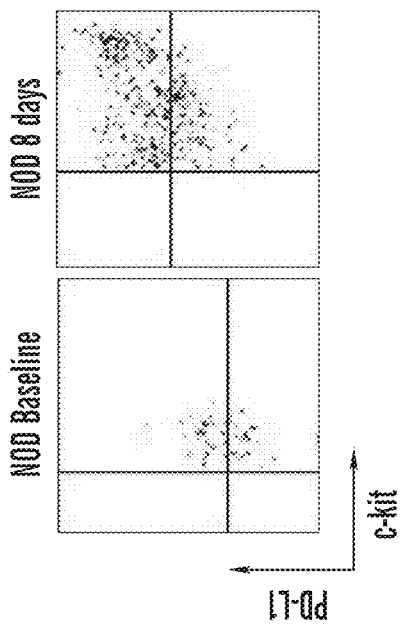

Murine HSCs ($Lin^-c-Kit^+Sca-1^+$, KLS) express PD-L1. We evaluated the characteristics of CXCR4 antagonist-mobilized HSCs by FACS analysis. $Lin^-c-Kit^+Sca-1^+$ cells were sorted from islet-transplanted or naïve CXCR4 antagonist-treated mice after 7 and 14 days of treatment. Interestingly, while most positive costimulatory molecules were found to be negative or scarcely expressed (CD40, CD80, CD86, PD-L2, ICOS, OX40, OX40L), PD-L1 was highly expressed by mobilized HSCs (58.0±7.1%). Extracted HSCs also expressed CXCR4 (38.4±4.2%). We then evaluated whether HSC mobilization increases the generation of PD-L1+ HSCs, and PD-L1+ HSCs did not increase in bone marrow from B6 islet-transplanted mice 6 h after the initiation of CXCR4 antagonist treatment. PD-L1 genetic deletion abrogates HSC immunoregulatory properties. To evaluate the immunoregulatory role of PD-L1 in murine HSCs, we investigated the effect of mobilized HSCs from WT and PD-L1 KO mice on the alloimmune response in vitro. A standard MLR assay was performed in which HSCs (from WT B6 or PD-L1 KO mice) were syngeneic to responder cells (CD4+ cells from B6) but allogeneic to bone marrow-derived DCs (from BALB/c). While HSCs from WT B6 mice abrogated the MLR response when added to culture, HSCs from PD-L1 KO mice failed to do so (FIG. 1). The percentage of peripheral PD-L1+ HSCs is reduced in NOD mice compared to B6. The percentage of peripheral PD-L1+ KLS in 10-week-old NOD and B6 mice was evaluated by FACS. A reduction of PD-L1+ KLS was evident in normo-glycemic NOD (10-week-old) as compared to B6 mice (peripheral PD-L1+ HSCs: B6=55.6±1.8 vs. NOD=29.5±1.54%; p<0.001). Moreover, PCR analysis confirmed that PD-L1 mRNA was upregulated in HSCs obtained from B6 mice compared to those obtained from NOD mice (FIGS. 2A-2C). The murine PD-L1 defect on HSCs can be overturned in vitro by pharmacologic approach. We performed a pilot study to assess the feasibility of generation of PD-L1+ HSCs in vitro by pharmacologic approach. KLS cells were isolated from splenocytes of B6 and NOD mice by magnetic beads and cultured with standard stem cell medium plus $PGE_2$ (2 µl, 10 µM). After 8 days, a ~30% fold increase in the PD-L1+ HSCs was evident (p=0.002 and p=0.001, in B6 and NOD KLS respectively), (FIGS. 2D-2E).

In Vitro Human Cell Studies—

Figure 3A:
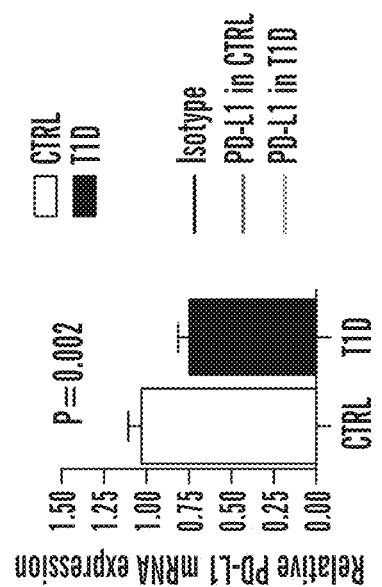
FIGS. 3A and 3B show that the PD-L1+ HSCs are fewer in number in T1D individuals as compared to healthy individuals.
Figure 3B:
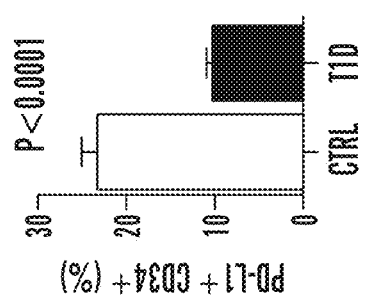
Figure 3C:
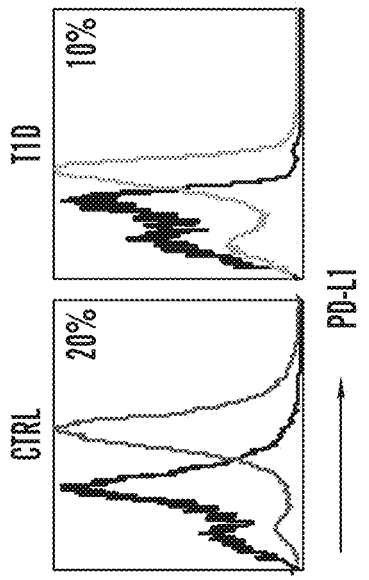
FIG. 3C shows the confirmation of PD-L1 defect, by PCR, in HSCs of individuals affected with T1D.

The percentage of peripheral PD-L1+ HSCs is reduced in T1D individuals as compared to healthy subjects. CD34+ cells were successfully purified by magnetic beads and we obtained a percentage of CD34+ cells from peripheral blood mononuclear cells (PBMCs) in healthy controls and T1D individuals of 0.05-0.07%. Fewer PD-L1+CD34+ cells were detectable in T1D individuals as compared to healthy subjects (T1D=9.5% vs. controls=23.5%; p<0.001), (FIGS. 3A-3C). A PCR analysis performed on RNA extracted from CD34+ cells previously isolated from PBMCs, confirmed that PD-L1 was upregulated in HSCs obtained from healthy subjects as compared to those obtained from T1D individuals. The human PD-L1 defect on HSCs can be overturned in vitro by pharmacologic approach. We performed a pilot study to assess the feasibility of generation of PD-L1+ HSCs ex vivo by a pharmacologic approach. PBMCs were isolated from peripheral blood of T1D individuals (n=10) using the Ficoll-Plaque protocol and CD34+ cells were sorted by magnetic beads. CD34+ cells were cultured as described herein this disclosure. After 7 days, a ~8 times fold increase in the percentage of PD-L1+ HSCs was evident (p=0.001), (FIGS. 3D-3E).

Example 3

In Vivo Murine Studies—

Figure 4B:
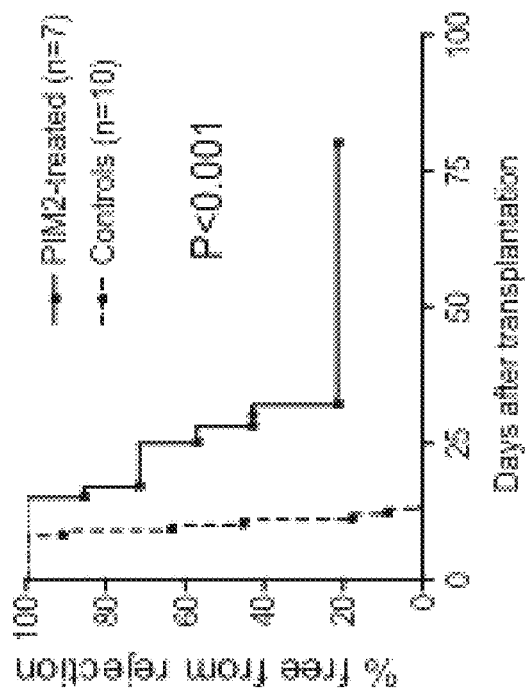
FIGS. 4A and 4B show that PD-L1/PD-1 cross-linking with PIM2 delays diabetes onset in NOD mice (FIG. 4A) and prolongs islet survival post islet transplantation (in-BALB/c into B6) (FIG. 4B).
Figure 4A:
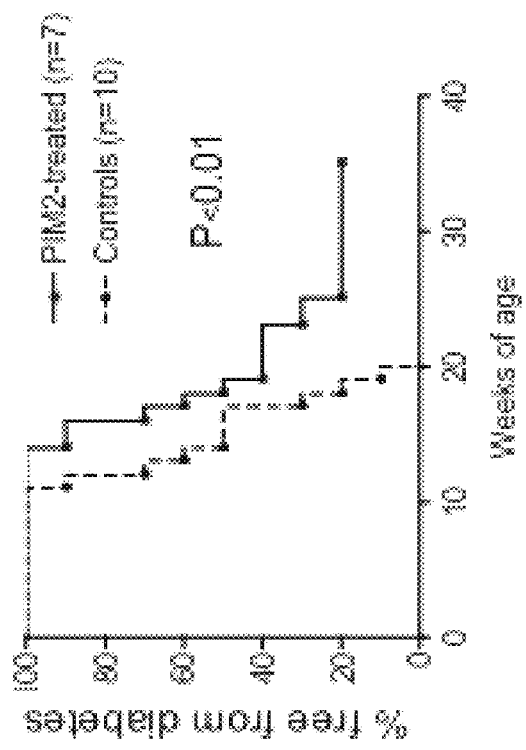
Figure 5A:
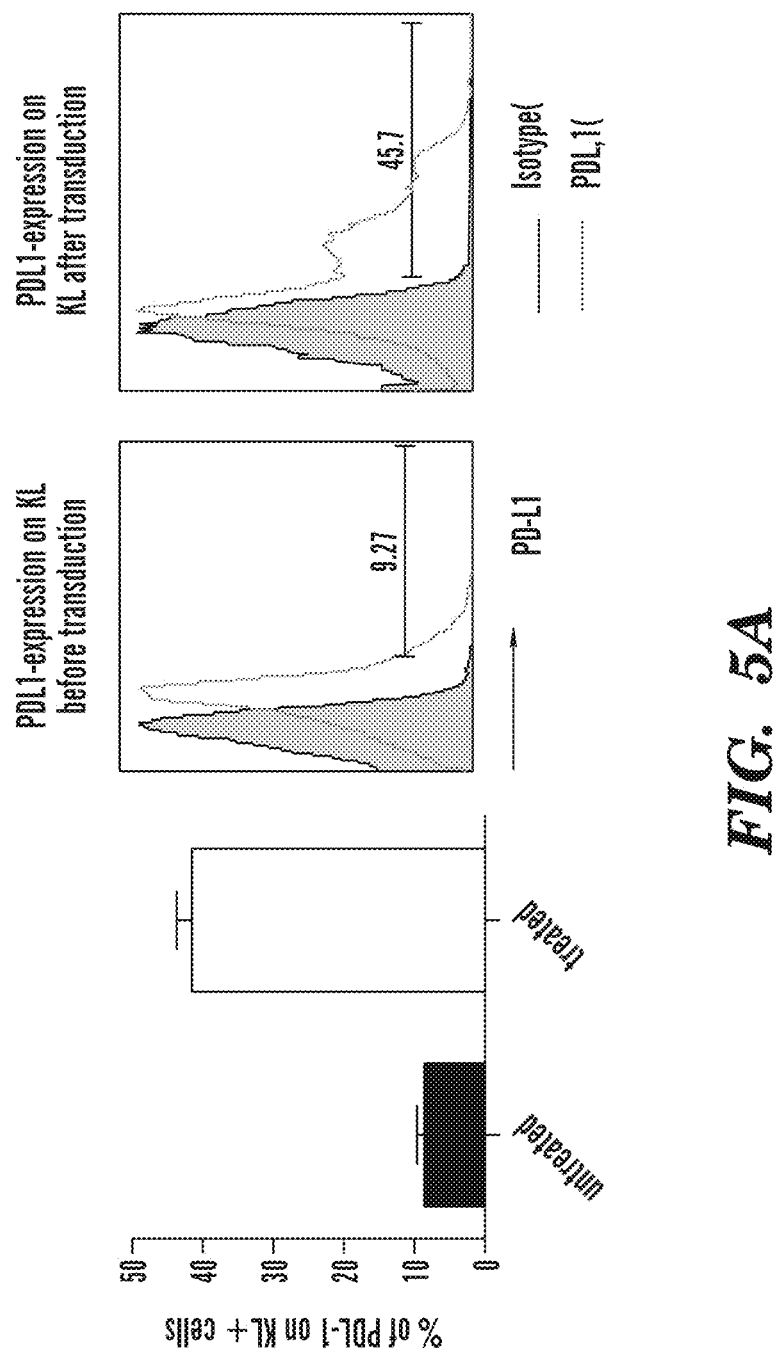
FIGS. 5A and 5B show that the HSCs transduced with PDL1 cDNA bearing lentivirus become highly PDL1+ and once adoptively transferred into newly diabetic NOD mice normalized glycemia. NOD untreated mice remained hyperglycemic at >250 mg/dl.
Figure 5B:
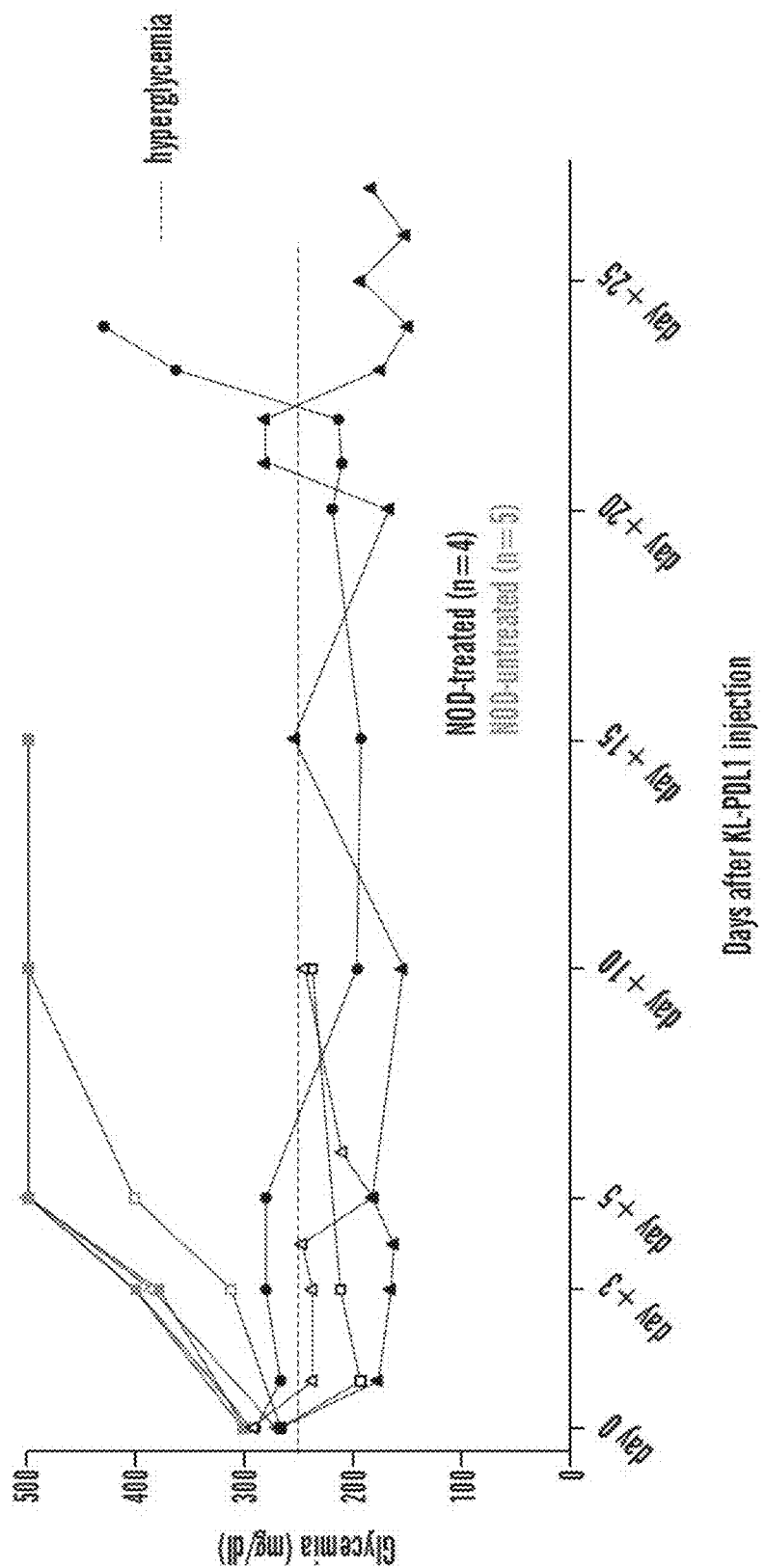
Figure 6:
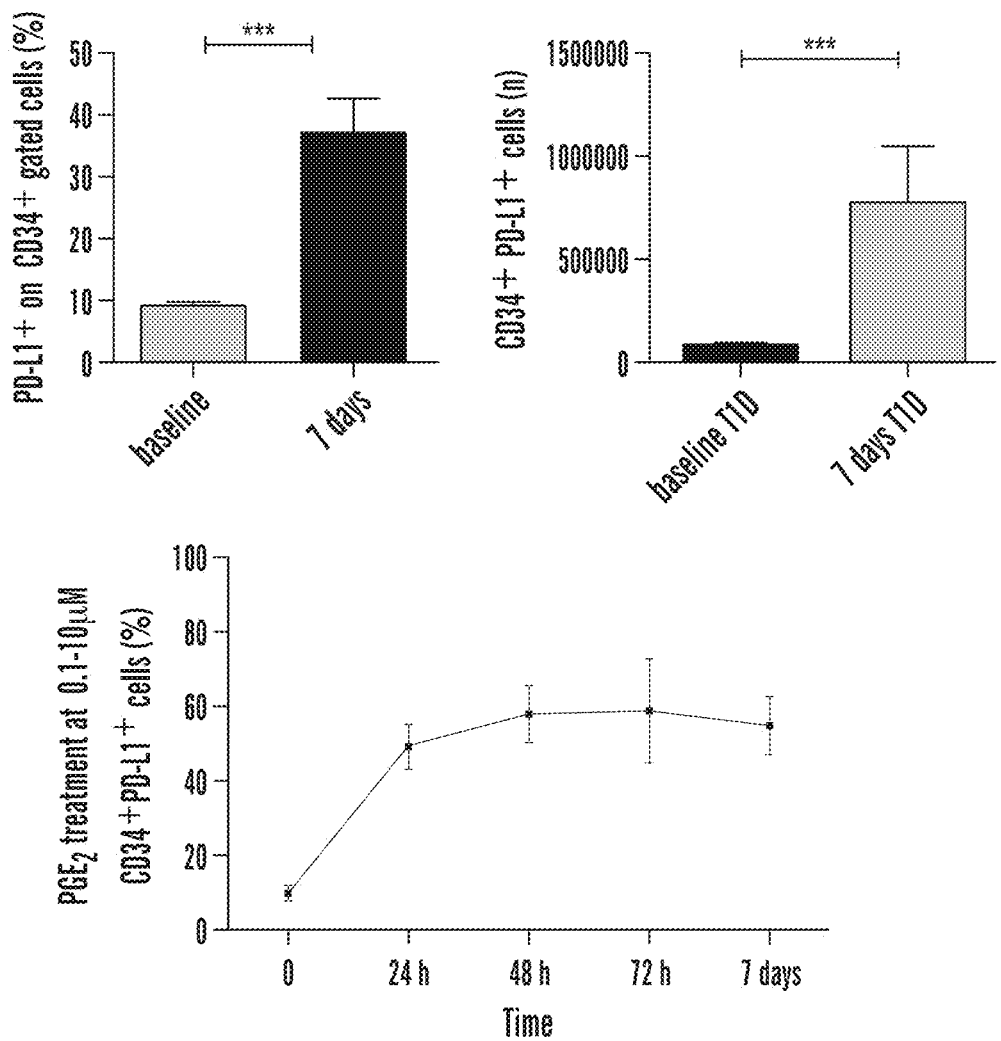
FIG. 6 show the effect of $PGE_2$ on PDL1 expression on HSC.
Figure 7:
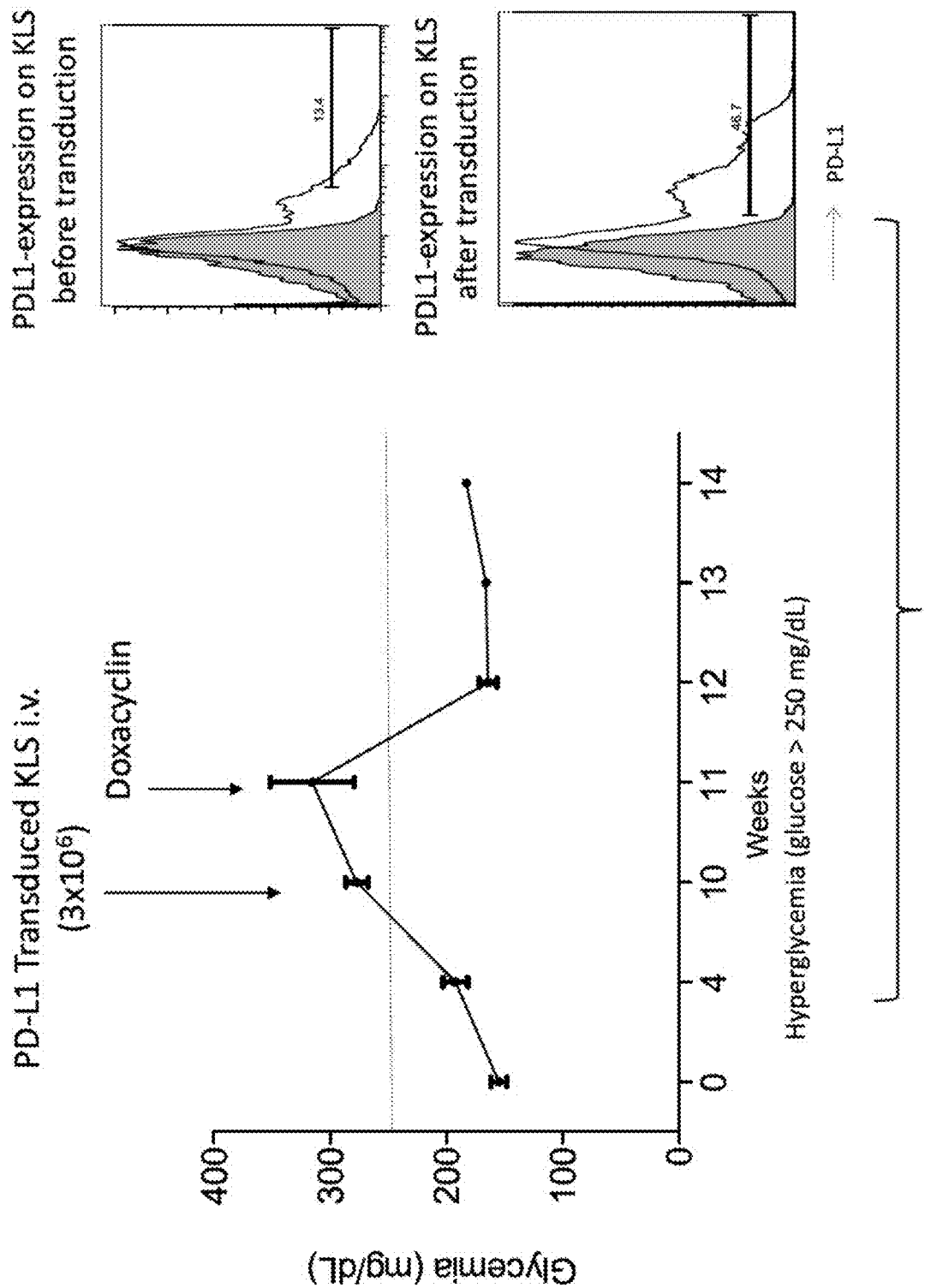
FIG. 7 show that the murine PD-L1 transduced KLS cells reverted hyperglycemia in NOD mice.

PD-L1/PD-1 crosslinking delays diabetes onset in NOD mice and islet graft rejection in streptozotocinated B6 mice. We used an anti-PD-1 mAb (hybridoma PIM-2, rat IgG2a) recently developed to stimulate PD-1, thus mimicking PD-L1 crosslinking to PD-1. PIM2 Ab delayed the onset of diabetes in NOD mice and islet allograft rejection (BALB/c into B6), (FIGS. 4A-4B). Infusion of PD-L1 transduced KLS reverted hyperglycemia in NOD mice. KLS were isolated from bone marrow of NOD mice and were transduced with PD-L1 pseudoviral particles previously obtained by infecting with a lentivirus vector, expressing a fluorescent marker ZsGreen and PD-L1 gene, 293TN producer cells. After obtaining a high concentration of the virus, KLS can be infected and subsequently expanded as PD-L1 transduced KLS in a 7-day culture. Expression of PD-L1 was under the control of a doxa promoter, thus doxacyclin needs to be injected in order to stimulate PD-L1 expression on transduced cells. $5\times10^6$ PD-L1 transduced KLS were then injected intravenously in hyperglycemic NOD mice and doxaclyclin was injected after 5 days. Injection of PD-L1-transduced KLS reverted hyperglycemia in NOD mice (n=2) for 18.5±2.5 days (FIGS. 5A-5B). PD-L1+ KLS reduced CD4-restricted anti-BDC2.5 autoimmune response in vitro. We challenged CD4+ T cells extracted from splenocytes of 10-week-old NOD mice in an anti-BDC2.5 stimulation ELISPOT assay with the addition of autologous HSCs generated using the pharmacologic approach already described (ratios of 1:1, 1:10, 1:100 of HSCs to effector cells). However, a defect in HSC immunoregulatory properties was evident in NOD mice.

Example 4

Functional Human Studies

Autologous haematopoietic stem cell transplant (AHSCT, also known as bone marrow transplant) is an immunosuppressive chemotherapy treatment combined with reinfusion of blood stem cells to help re-build the immune system. AHSCT in new-onset T1D rendered normoglycemic nearly 60% of treated individuals at 6 months. In a group of 65 individuals followed up for 48 months, AHSCT in a non-myeloablative setting achieved insulin independence in nearly 60% of T1D individuals within the first 6 months after receiving conditioning immunosuppression (ATG+Cyclophosphamide) and a single infusion of autologous HSCs. 32% of treated subjects remained insulin-independent at the last time point of their follow-up. Treated subjects showed a decrease in HbA1c and an increase in C-peptide levels as compared to pre-treatment.

Despite a complete immune recovery (i.e. leukocyte count) after treatment, 52% of treated individuals experienced adverse effects. HSCs of T1D individuals are defective in their immunoregulatory properties. We challenged CD4+ T cells extracted from PBMCs of healthy subjects or T1D individuals in an anti-CD3/-CD28 stimulation assay with the addition of autologous CD34+ cells (human HSCs) newly generated using our pharmacologic approach (1:1, 1:10, 1:100 ratio of HSCs to effector cells). Addition of HSCs obtained from healthy subjects led to a dose-dependent decrease of IFN-γ-producing CD4+ T cells. On the contrary, a defect in immunoregulatory properties was evident when HSCs from individuals with T1D were added. HSCs exhibited impaired mobilization in individuals with T1D. To confirm that the mobilization of HSCs cells (CD34+) is not an expression, we evaluated the mobilization properties of HSCs in T1D individuals. We thus established a trial (NCT01102699) that was performed with Padua University (Dr. Gianpaolo Fadini), in which we tested bone marrow responsiveness to 5 µg/kg hrG-CSF in 6 individuals with T1D. While CD34+ cells significantly increased in healthy controls, an impaired mobilization of CD34+ was observed in T1D individuals. This data confirm the existence of a HSC "mobilopathy" in T1D individuals. HSC mobilization with a CXCR4 antagonist does not increase PD-L1+

HSCs of T1D individuals. To assess whether mobilization alters expression of PD-L1 on HSCs we studied the immune phenotype of HSCs before and after mobilization with anti-CXCR4 in 5 healthy subjects and 8 individuals with T1D. While PD-L1 expression on $CD34^+$ cells increased in healthy subjects after mobilization (6.2±0.6 vs. 0.6±0.2, p=0.0001), it did not change in $CD34^+$ cells of T1D individuals (4.7±1.5 vs. 1.5±0.8) highlighting that CD34+ cells require an in vitro manipulation to overturn PD-L1 defect and recover their immunoregulatory properties.

Example 5

$PGE_2$ Highly Augment PDL1 Expression in HSC Cells Both Murine and Human.

Murine: we cultured isolated HSCs (KL cells) in a serum-free culture medium supplemented with standard stem cell growth factors and pulsed with the novel small molecule derived from prostaglandins E2 ($PGE_2$) at different time-points during a 8-day culture. Briefly, peripheral $Lin^{neg}Sca\text{-}1^+Kit^+$ cells were isolated from 10-week-old NOD mice, and 150-200 plated into each well on a 96-well plate with 200 ml of Stemspan serum-free medium (Stem-Cell Technologies) supplemented as already described. $PGE_2$, which has been shown to implement expansion of murine/human isolated HSCs in vitro and it is now being tested in humans in phase II clinical trials, has been added (2 µl, 10 µM, Chemicon) at 24 h, 96 h and at 6 days to enrich the pool of $PD\text{-}L1^+$ HSCs newly generated. Cells were cultured for 8 days at 37° C. in 5% $CO_2$.

Human: human HSCs were cultured using StemSpan supplemented with human stem cell growth factors as previously reported (22). Briefly, $CD34^+$ cells were plated at $5\times10^5$ cells/ml in supplemented StemSpan on a 96-well plate, at 200 µl/well for 7 days. HSCs were pulsed with $PGE_2$ as described in murine experiments. $PD\text{-}L1^+$ HSCs were quantified by FACS analysis at different timepoints and at the end of the procedure.

Example 6

Treatment Protocol with PD-L1+ Expressing Hematopoietic Stem Cell.

Initial Evaluation—

Patients will undergo standard work-up for autologous bone marrow transplantation according to institutional guidelines, and then undergo two bone marrow harvests at a minimum of 4 weeks apart that will be used for a back-up marrow (minimum of $2\times10^6$ CD34+ cells/kg) and for a harvest of autologous bone marrow (target of $5\times10^6$ CD34+ cells/kg with a minimum of $4\times10^6$ CD34+ cells/kg).

Harvest of a Back-Up Autologous Graft—

Hematopoietic cells will be collected from the patient in advance of the treatment, to serve as a salvage procedure ("back-up graft"), should there be no hematopoietic recovery observed 6 weeks following the injection of genetically-manipulated cells, or should manipulated cells fail to meet release criteria. Bone marrow (up to 20 ml/kg) will be harvested from the patient under general anesthesia from the posterior iliac crests on both sides by multiple punctures at a minimum of 4 weeks prior to gene therapy. A portion of the bone marrow containing $2\times10^6$ CD34+ cells/kg will be frozen and stored unmanipulated in liquid nitrogen vapors (−162° C. and −180° C.) according to standard clinical procedures for autologous bone marrow collection to constitute the back-up graft. The remainder of the harvest will be selected for CD34+ cells (described below) and utilized for gene modification (described below).

Bone Marrow Harvest—

The remainder of the first bone marrow harvest in excess of the needed back up marrow will be utilized with a second bone marrow harvest for gene transfer. The second harvest will occur no sooner than 4 weeks after the initial harvest (described above). For the second harvest, bone marrow will again be harvested from the patient under general anesthesia from the posterior iliac crests on both sites by multiple punctures. The amount of marrow collected will be up to 20 ml/kg of body weight. This will give a total nucleated cell count of greater than ~$4\times10^8$ cells/kg. This in turn should yield a $CD34^+$ cell dose of greater than $4\times10^6$ cells/kg after CD34+ cell selection.

Subjects from whom the estimated CD34+ count of both harvests is <$4\times10^6$ cells/kg will not receive conditioning. After a period of at least 6 weeks, if the subject wishes to remain on study, he may be harvested again. Subjects withdrawn from the study prior to administration of transduced CD34+ cells will resume normal clinical care (supportive care and/or allogeneic HSCT). Efficacy and safety assessments will not be carried out from the point of withdrawal and data will not be collected for the database.

CD34+ Cell Purification—

To allow sufficient time for clearance of conditioning agents and minimize the time of pre-stimulation and culture, whole bone marrow will be held overnight. The bone marrow will be red cell-depleted by density gradient centrifugation. CD34+ cells will be positively selected from the bone marrow mononuclear cells using the CliniMACS reagent and instrument. Quality control (QC) samples are taken to assess purity and sterility. Purified cells will be immediately processed for pre-stimulation and transduction.

CD34+ Cells Pre-Stimulation and Transduction with Vector—

Transduction will be carried out on one or both harvests. Transduction of cells in excess of the back-up marrow target from the first harvest will be transduced and frozen for future use. The second harvest will be used for gene transfer in its entirety and the transduced product of the second harvest will be infused with the thawed transduced cells from the first harvest after conditioning.

Purified CD34+ cells are seeded in closed culture bags at a density of $0.5\text{-}1\times10^6$/ml in serum-free medium supplemented with growth factors (IL-3, SCF, FLT3L, TPO) and placed in an incubator at 37 C, 5% $CO_2$. After 24-30 hours, cells are harvested and counted. Additional QC testing includes cell viability, and Colony Forming Unit (CFU) assay. Cells are transferred to a new culture bag and treated with lentiviral supernatant. For this first round of transduction, cells are incubated for 18-24 hours. Cells are then harvested, counted, and transferred to a new bag, with lentiviral supernatant for a second round of transduction.

Final Harvest and Formulation—

After the second round of transduction, cells are harvested, washed in plasmalyte and resuspended in their final formulation (PLASMALYTE, 1% HSA) in a volume of 50-100 mL. All cells available after removal of the QC samples will be infused into the patient. QC includes cell count, viability, sterility on wash supernatant, *Mycoplasma*, Endotoxin on supernatant, phenotype, CFU, RCL (samples taken and archived), insertional analysis, and average vector copy number by qPCR (cultured cells). A sample for Gram stain is taken from the product immediately before delivery to the patient.

CD34+ Cells Ex Vivo Culture and Stimulation with PGE$_2$—

Purified CD34+ cells are seeded in closed culture bags at a density of 0.5-1×10$^6$/ml in STFIA medium was defined as serum-free medium supplemented with 10 µg/ml heparin, 10 ng/ml human SCF, 20 ng/ml human TPO, 10 ng/ml human FGF-1, 100 ng/ml IGFBP2, and 500 ng/ml Angptl3, placed in an incubator at 37 C, 5% CO$_2$ and cultured for 48 h. The media is changed and PGE$_2$ is added to the cells to achieve a final concentration of 0.1 µM. After another 24 h hrs, PGE$_2$ is added to the cell again. The cells are harvested at 1-8 days after the second PGE$_2$ addition. For harvest later than day 2, addition PGE$_2$ in added to the culture media at day 2, day 4 and day 6, together changes of culture media.

Testing Prior to Subject Re-Infusion—

Samples are collected during and at the end of the procedure for cell count and viability (trypan blue exclusion or equivalent), sterility, *mycoplasma*, transduction efficiency (vector copy number), Gram stain, endotoxin and RCL testing. Of these only cell viability, sterility (in process, 72 hours), Gram stain and endotoxin measurements will be available prior to infusion.

If microbiological cultures reveal transient bacterial contamination, by Gram stain or positive culture at 72 hours, Cell Manipulation Core Facility staff will contact the PI, the assistant medical director and attending physician to decide whether to infuse the back-up harvest or infuse the product with antibiotic coverage. If back-up harvest is infused, the subject will be withdrawn from the protocol. If the cell viability is <70%, sterility testing is positive, or endotoxin is >5 EU/kg/hr, the cells will not be returned, back-up harvest will be infused and the subject will be withdrawn from the protocol.

If viable cell count from both harvests/transductions is greater than or equal to 4×10$^6$ CD34+ cells/kg at the end of transduction, cells will be infused. If viable cell count from both harvests/transductions is less than 4×10$^6$ CD34+ cells/kg at the end of transduction, cells will not be infused and back-up harvest will be infused 48 hours later.

Samples of the CD34+ cells may be tested for PD-L1 expression.

Subjects withdrawn from the study prior to administration of transduced CD34+ cells will resume normal clinical care (supportive care and/or allogeneic HSCT). Efficacy and safety assessments will not be carried out from the point of withdrawal and data will not be recorded in the Case report forms (CRFs).

Subject Conditioning Regimen—

Subjects will receive myeloablative conditioning with Busulfan (~4 mg/kg intravenously daily, adjusted for weight, (given over 3 hours once daily) administered on days −4 to −2, prior to infusion of transduced cells. Conditioning will occur concurrent with purification and transduction of bone marrow cells. Busulfan levels will be drawn on all 3 days of administration, and levels on days 1 and 2 will be used to adjust for weight.

Infusion of Transduced Cells—

Cells will be infused intravenously over 30-45 minutes after standard prehydration and premedication according to conventional hospital Hematopoietic Stem Cell Transplantation Unit standard guidelines. This standard requires that the patient be on continuous cardiac, respiratory and oxygen saturation monitor throughout the infusion and for 30 minutes afterwards. Vital signs will be measured and recorded pre-transfusion, 15 minutes into transfusion, every hour for duration of infusion, and end of transfusion. The RN will stay with the patient for the first 5 minutes of the transfusion. If two transduction products are administered, the second transduced product will be administered without delay after the first.

Example 7

ToleraCyte™, a programmed CD34$^+$/PD-L1$^+$ immuno-regulatory cell product of Fate Therapeutics, Inc., have been show to treat T1D mice. ToleraCyte™ is a programmed CD34+ cell immunotherapy that is undergoing preclinical investigation for the treatment of autoimmune and inflammatory disorders. The immuno-regulatory cell therapy is comprised of CD34+ cells that have been programmed ex vivo with a proprietary combination of pharmacologic modulators. ToleraCyte is designed to optimize the capacity of CD34+ cells to effectively traffic to sites of inflammation and express potent T-cell regulatory factors, including PD-L1 and IDO1.

In preclinical experiments on well-established non-obese diabetic (NOD) mice, the mouse model of human Type 1 diabetes (T1D), a single administration of programmed cells ToleraCyte™ results in durable correction of T1D diabetes in a NOD mouse model. The hyperglycemic NOD mice are designed to mimic new-onset type 1 diabetes. In addition, it was also shown that in pre-hyperglycemic NOD mice, a single administration of programmed cells ToleraCyte™ statistically and significantly delays the onset of T1D in NOD mice, where the median time to onset was not reached by Day 140 as compared to untreated mice (median time to onset=Day 115; p=0.0004).

Furthermore, in a humanized model of type 1 diabetes, programmed CD34+ cells showed enhanced trafficking to the pancreas and regulation of T-cell activation. Together, these preclinical results support the premise that ToleraCyte™ can serve as a disease-modifying immunotherapy for patients with type 1 diabetes. (SAN DIEGO, Jun. 11, 2016 (GLOBE NEWSWIRE).

Example 8

Experimental Design and Methods
Design and Methods for Human Studies
Patients Characteristics—

Blood samples were obtained from new onset diabetic individuals (New-onset T1D), long-standing diabetic individuals (T1D) and healthy individuals (CTRL) in accordance with The San Raffaele Scientific Research Institute under an Institutional Review Board committee approval. Peripheral blood mononuclear cells (PBMC) fractions were isolated by Ficoll density gradient centrifugation for cell culturing experiments. Additional blood samples were obtained from T1D subjects and CTRL at baseline before treatment and 6 hours after treatment with CXCR4-antagonist (Mozobil; Sanofi) at the dose of 0.24 mg/kg body weight in accordance with the Institution Review Board Committee of Padova (2996P) and was performed in accordance with the Declaration of Helsinki (Clinical trial registered on clinicaltrials.gov (NCT02056210)). Patients with Type 1 Diabetes aged 18-65 years were recruited among those referred to the diabetes outpatient clinic of the University Hospital of Padova. Individuals without diabetes aged 18-65 years were recruited from those referred to the same outpatient clinic for screening of other metabolic diseases. All provided written informed consent. Exclusion criteria were pregnancy or lactation; recent (within 2 months from study entry) surgery, trauma, or acute diseases; immune diseases (except from type 1 diabetes and autoimmune thyroiditis);

chronic infectious diseases; hematologic malignancies either past or present; solid tumor known or strongly suspected; leukocytosis, leukopenia, or thrombocytopenia; solid organ transplant or immunosuppression; alteration of hepatic function (transaminases >2 upper limit of normality); severe chronic diabetic micro- or macroangiopathy; $HbA_{1c}$>11%; deficit in renal function (estimated glomerular filtration rate <50 mL/min/1.73 $m^2$); significant abnormalities of the peripheral lymphocyte immunophenotype; known hypersensitivity to plerixafor or its excipients; and refusal or inability to provide informed consent. Women with childbearing potential could participate in the study if on oral contraception, and a negative pregnancy test was required before study entry. Women were also asked to continue oral contraception for 3 months after plerixafor administration. All medications for the treatment of diabetes and for other medical conditions were allowed during the study.

Human Antibodies—

The following antibodies were used for flow cytometric analysis in the reported studies: phycoerythrin (PE)-conjugated anti-human PD-L1 (CD274) or allophycocyanin (APC)-labeled anti-human PD-L1 (CD274), PE-conjugated anti-human PD-1 (CD279), PE-conjugated anti-human PD-L2 (CD273), PE-conjugated or R-Phycoerythrincyanin 5.1 (PCS) conjugated anti-human CD34, fluorescein isothiocyanate (FITC)-conjugated anti-human CD45, PE-conjugated anti-human-CD19, peridin-chlorophyll-protein complex (PerCP)-conjugated anti-human CD11c and Pacific Blue (PB)-conjugated anti-human CD16 were purchased from BD Biosciences, Biolegend or Beckman Coulter. The following antibodies corresponded to different isotype controls for the abovementioned human antibodies: PE-conjugated mouse IgG1κ, mouse PCS-conjugated IgG1, APC-labeled mouse IgG2bκ.

Human Flow Cytometric Analysis—

To assess PD-L1, PD-L2 and PD-1 expression on human HSCs, fresh blood collected from healthy individuals, T1D and new-onset T1D individuals was stained with PE-Cy5.5 anti-human CD34, PE anti-human PD-L1 or PD-L2 or PD-1 (BD Biosciences). Fresh blood was also stained with PE anti-human PD-L1 together with PECy7 anti-human-CD19, APC anti-human CD11c or Pacific blue anti-human CD16 (all BD Biosciences) to assess PD-L1 expression on B cells, dendritic cells or monocytes, respectively. BD LSRFortessa flow cytometer (BD Biosciences) was used to analyze cells with the light scatter properties of stem cells or lymphocytes. Background staining was determined using nonreactive isotype-matched control mAbs with gates positioned to exclude 99% of non-reactive cells. FlowJo software version 8.7.3 (Treestar, Ashland, Oreg.) was used for analysis. Apoptosis was assessed by permeabilization of previously isolated CD34+ cells, which were next stainied with APC Annexin V (BD Bioscience) while dead cells were detected using a Fixable Viability Dye Staining (Amcyan, eBioscience).

In Vitro Proliferation Assay and Glucose Challenge of Human CD34+ Cells—

CD34+ cells were first isolated using magnetic beads (Milteny kit) from PBMCs obtained from blood samples of enrolled subjects. Next, CD34+ cells were stained with CFSE (FITC, Invitrogen C1157) and cultured for 72 hours at 37° C. in 5% CO2 in StemSpam SFEM II media (StemCell Technologies). Proliferation was visualized by flow cytometry according to the dye dilution at 24 h, 48 h and 72 h. To assess whether glucose exposure affects PDL-1 expression on CD34+ cells, we cultured CD34+ cells, previously isolated from PBMCs obtained from CTRL and T1D, in DMEM without serum at different glucose concentrations (5 mM, 20 mM and 35 mM) for 72 h. PDL-1 expression was assessed by FACS as previously described.

Pharmacological modulation of human HSCs CD34+ HSCs—

$1 \times 10^6$ of isolated human CD34+ HSCs cells were cultured in 200 µl of StemSpan SFEM II media supplemented with recombinant human SCF (50 ng/ml), recombinant human TPO (50 ng/ml), recombinant human FLT3-L (50 ng/ml), human IFN-β (1000 U/ml), human IFN-γ (5 ng/ml) and human Polyinosinic-polycytidylic acid (Poly I:C) (1 µg/ml) in a U-bottom 96-well plate at 37° C. in 5% CO2. PD-L1 expression was evaluated before and after 24 hours of culture by flow cytometry using anti-human CD34 and anti-human PD-L1, and with their corresponding isotype controls.

Human ELISpot Assay—

An ELISPOT assay was used to measure the number of IFN-γ-producing cells according to the manufacturer's protocol (BD Biosciences, San Jose, Calif.) as previously showed by our group (16). $1 \times 10^6$ PBMC, isolated from T1D patients, were cultured for 48 h in presence of IA-2 (100 µg/ml) peptide in RPMI media supplemented with 10% FBS. At day one after stimulation, 500 µl of media were added to the culture. Cells were collected at day 2 and plated in a human IFN-γ ELISpot assay with or without CD34+ HSCs, Trifecta-modulated CD34+ HSCs in a ratio of 1:1, 1:2, 1:4, or 1:8 in RPMI media un-supplemented. Spots were counted using an A.ELVIS Elispot Reader (A.EL.VIS GmbH, Hannover, Germany) or on an Immunospot Reader.

Western Blot—

Total proteins of intestinal bioptic samples were extracted in Laemmli buffer (Tris-HCl 62.5 mmol/l, pH 6.8, 20% glycerol, 2% SDS, 5% β-mercaptoethanol) and their concentration was measured (Lowry et al., 1951). 35 µg of total protein was electrophoresed on 7% SDS-PAGE gels and blotted onto nitrocellulose (Schleicher & Schuell, Dassel, Germany). Blots were then stained with Ponceau S. Membranes were blocked for 1 h in TBS (Tris [10 mmol/l], NaCl [150 mmol/l]), 0.1% Tween-20, 5% non-fat dry milk, pH 7.4 at 25° C., incubated for 12 h with a polyclonal goat anti-human Pdcd-1L1 antibody (Santa Cruz Biotechnology, Santa Cruz, Calif., USA) diluted 1:200 or with a monoclonal mouse anti-β-actin antibody (Santa Cruz Biotechnology) diluted 1:1000 in TBS-5% milk at 4° C., washed four times with TBS-0.1% TWEEN®-20, then incubated with a peroxidase-labeled mouse anti-goat IgG secondary antibody (or rabbit anti mouse for β-actin) diluted 1:1000 (Santa Cruz Biotechnology) in TBS-5% milk, and finally washed with TBS-0.1% Tween-20. The resulting bands were visualized using enhanced chemiluminescence (SuperSignal; Pierce, Rockford, Ill., USA).

qRT-PCR—RNA from isolated CD34+ cells was extracted using Trizol® Reagent (Invitrogen), and qRT-PCR analysis was performed using TaqMan assays (Life Technologies, Grand Island, N.Y.) according to the manufacturer's instructions. The normalized expression values were determined using the ΔCt method. Quantitative reverse transcriptase polymerase chain reaction (qRT-PCR) data were normalized for the expression of ACTB, and ΔCt values were calculated. Statistical analysis compared gene expression across all cell populations for each patient via one-way ANOVA followed by Bonferroni post-test for multiple comparisons between the population of interest and all other populations. Statistical analysis was performed also by using the software available $RT^2$ profiler PCR Array Data Analysis (Qiagen). For two groups comparison Student t test was employed. Analysis was performed in triplicates after isolation of fresh CD34$^+$ cells. Below are reported the main characteristics of primers used:

| Gene Symbol | UniGene # | Refseq Accession # | Band Size (bp) | Reference Position |
|---|---|---|---|---|
| DC274 (PDL-1) | Hs.521989 | NM_001267706.1 | 89 | 614 |

Confocal Microscopy—

Bone marrow sections from Type 1 diabetic individuals and from healthy control subjects and then stained with the corresponding antibodies. Images were captured on Zeiss LSM 510 Meta confocal microscope (Carl Zeiss SpA). Details of the staining procedure can be found in supplemental procedures.

Design and Methods for Murine Studies

Animals—

Female NOD/ShiLtJ (NOD) and male C57BL/6J mice were purchased from The Jackson Laboratory (Bar Harbor, Me.). All mice were used according to institutional guidelines, and animal protocols were approved by the Boston Children's Hospital Institutional Animal Care and Use Committee.

Diabetes Monitoring—

Overt diabetes was defined as blood glucose levels above 250 mg/dL for 2 consecutive days. Blood glucose was measured using the Breeze2 (Bayer S.p.A., Viale Certosa, Milano, Italy) blood glucose meter.

Reversal Studies—

Female NOD mice were monitored beginning at 10 weeks of age, and on day 2 of hyperglycemia (>250 mg/dl), were injected with KL-PD-L1.Tg cells, or HSCs-unmodulated cells, HSCs-mock-transduced cells or HSCs-modulated with trifecta (see description above), were administered as 3×10$^6$ cells via vein tail. Mice were monitored daily by measuring blood glucose until the time of sacrifice (normoglycemia was observed the following day post-treatment as below 250 mg/dl), and measurements were performed by tail bleeding according to National Institutes of Health guidelines. Bone marrow cells were obtained from femurs and tibiae of NOD and C57BL/6J mice by flushing with phosphate buffered saline (PBS). Bone marrow cells were lineage depleted by using the Lineage Negative Depletion Kit (Miltenyi Biotec). Upon depletion, lineage negative c-kit$^+$ cells were isolated using CD117 Microbeads (Miltenyi Biotec), following the manufacturer's instruction.

Murine Flow Cytometry Antibodies—

The following antibodies were used for flow cytometric analysis for assessing phenotypic characterization of KL extracted from bone marrow and spleen: phycoerythrin (PE)-conjugated anti-human PD-L1 (CD274) or allophycocyanin (APC)-conjugated rat anti-mouse PD-L1 (CD274), phycoerythrin (PE)-conjugated rat anti-mouse PD-1 (CD279), phycoerythrin (PE)-conjugated rat anti-mouse PD-L2 (CD273), were purchased from BD Biosciences or Biolegend respectively. The following antibodies corresponded to different isotype controls for the abovementioned murine antibodies: PE Mouse IgG1, κ Isotype Ctrl; and APC Mouse IgG2b, κ Isotype Ctrl.

Immunophenotypic Characterization of Murine KL Characterization—

Murine KL cells previously extracted from bone marrow were suspended in 20 µL of buffer, then stained with the following antibodies and incubated according to manufacturer's instructions for 30 minutes at 4° C. Cells were washed with buffer, centrifuged at 300 g for 10 minutes and suspended in 300 µl of buffer. The following antibodies were used for the staining: Rat anti-mouse CD274 or CD273 or anti-mouse CD279. PD-L1, PD-L2 and PD-1 expression on KL cells was represented as histograms.

Extracted bone marrow from 8 weeks NODs and B6 mice were subject to red blood lysis with ACK-lysing buffer (BD lysis buffer) followed by a washing step in Flow buffer (BD staining buffer). Bone marrow cells were stained with the following cocktail of antibodies:

Anti-Lineage negative cocktail-APC, anti-C-kit-PerCP, anti-Sca1-FITC, anti-CD150-PE, anti CD41FITC, anti-CD48-PerCP, anti-CD244 PerCP, anti-PD-L1-PE and anti-PD-L1-APC. All antibodies were purchased from eBioscience and from BD Pharmingen. Samples will be incubated for 30 min in the dark at 4° C. and then washed again with Flow Medium and eventually fixed with Formalin 1%. Samples will be examined at FACS Calibur and results will be analysed using Flowjo software.

Flow Cytometric Analysis, Non-Hematopoietic Stem Cells Characterization—

1×10$^6$ cells per sample will be stained with anti-mouse B220-PE to assess B cells and dendritic cells will be determined with anti CD11c-PerCP and monocytes with anti-mouse F4/80 APC. PD-L1 expression in B220$^+$ cells, CD11c$^+$ cells and CD16$^+$ cells was assessed by using anti-mouse CD274-PE. Briefly, isolated bone marrow cells and splenocytes were washed in Flow Medium (PBS with 2% of FCS and 0.05% of sodium azide) and stained with the appropriate dilution of flow antibodies. Samples will be incubated for 30 min in the dark at 4° C. and then washed again with Flow Medium and eventually fixed with Formalin 1%. Samples will be examined at FACS Calibur and results will be analyzed using Flowjo software. anti-mouse CD11c-PerCP was purchased from Biolegend, anti-mouse F4/80 APC from eBioscience and anti-mouse PD-L1 used is from BD Pharmingen.

Apoptosis Assay—

Isolated KL cells were washed twice with cold PBS and then resuspended in 1× Binding Buffer (component no. 51-66121E; BD Pharmingen) at a concentration of 1×10$^6$ cells/ml. Then 100 µl of the solution (containing 1×10$^5$ HSCs) were transferred into a 5 ml culture tube and proceeded by a staining with 5 µl of PE Annexin V and 5 µl 7-AAD and followed by a vortex of cells and incubation for 15 min at RT (25° C.) in the dark. After incubation, 400 µl of 1× Binding Buffer to each tube were added to each tube prior to their acquisition by flow cytometry. The following controls were used to set up compensation and quadrants: unstained cells, cells stained with PE Annexin V (no 7-AAD) and cells stained with 7-AAD (no PE Annexin V). Cells that stained positive for PE Annexin V and negative for 7-AAD were undergoing apoptosis. Cells that stained positive for both PE Annexin V and 7-AAD were either in the end stage of apoptosis, were undergoing necrosis, or were already dead. Cells that stained negative for both PE Annexin V and 7-AAD were alive and not undergoing measurable apoptosis.

In Vitro Proliferation Assay—

Isolated KL cells were washed twice with cold PBS buffer without FCS, then resuspended in half final volume of buffer at 3×10$^7$ cells/ml and into the other half of volume was added CFSE to reach a final concentration of 10 uM. Diluted CFSE will be added to cell suspension followed by a vortex and incubation at 37° C. for 15 minutes. After incubation, FCS was added to cell suspension in order to quench any remaining free CFSE, and the tube will be filled completely with PBS buffer. After a second wash, cells were resuspended in media and were cultured for 3 days at 37° C. in 5% $CO_2$. After 72h proliferation of KL cells can be visualized at flow cytometry according to the dye dilution.

Murine ELISpot Assay—

An ELISPOT assay was used to measure the number of IFN-γ-producing cells according to the manufacturer's protocol (BD Biosciences, San Jose, Calif.) as previously showed by our group (16). $1\times10^6$ of splenocytes, isolated from NOD-treated mice (NOD-PD-L1.Tg treated, NOD-Trifecta-treated, NOD-KL-treated) and NOD-untreated mice, were cultured for 24 hours in presence of the following murine islets peptides (150 μg/ml): BDC2.5, IGRP, GAD65 and insulin at 300 μg/ml. Spots were counted using an A.ELVIS Elispot Reader (A.EL.VIS GmbH, Hannover, Germany)

Cell Lines and Cell Culture—

Lenti-X™ 293T Cell Line used in this study was purchased from Clontech as recommended. All procedures involving human cell line HEK293T and lentiviral methodologies were approved by the Institutional Biosafety Committee (IBC) of Boston Children's Hospital Committee, Harvard Medical School.

Lentivirus Production and Transduction—

The full-length cDNA encoding murine PD-L1 was cloned into the transfer plasmid pHAGE-fullEF1a-MCS-IZsGreen. VSV-G pseudotyped lentiviruses were generated by co-transfection of the murine PD-L1 transfer plasmid together with the packaging expression plasmids (Gag/Pol, Tat, Rev) and the envelope expressing plasmid encoding for VSV-G into 293T cells using the Trans-IT 293 transfection reagent (Minis). 24 or 48 hours post transfection, the supernatant containing the viral particles was collected, centrifuged at 1800 rpm for 5 minutes to remove dead cells and debris, and concentrated using the Lenti-X concentrator following manufacturer's protocol (Takara Clonetech). Viral stocks were stored at −80° C. until transduction experiments were performed. Freshly isolated murine KL cells were transduced with recombinant PD-L1 lentiviral particles in Stem SFEMII (Stem cell Technology) in presence of 2 μg/mL polybrene (Sigma), 10 ng/ml of SCF and 100 ng/ml of TPO. 24 hours after transduction, cells were collected for FACS analysis and used for reversal studies.

Luciferase Assay—

KL cells isolated from NOD.FVB-Tg(CAG-luc,-GFP) L2G85Chco/FathJ were purchased from Jackson Laboratory then were transduced with PD-L1 lentivirus and injected to NOD-hyperglycemic. After 24 hours, treated mice were injected with luciferin. Following luciferin injection, luciferase expression is assessed by IVIS Spectrum. Details of the whole procedure can be found in supplemental methods.

Modulation of Murine KL Cells HSCs—

Murine bone marrow KL cells were isolated using magnetic beads and MACS® separation columns (Miltenyi) and $-2\times10^5$ cells were plated in a U-bottom 96-well plate (3799; Corning) with 200 μl of the following medium. Stemspan-SFEMII (StemCell Technologies) supplemented with a cocktail of different growth factors. Cells were cultured for 24 hours at 37° C. in 5% $CO_2$. PD-L1 expression was evaluated before culture by FACS using rat anti-mouse PD-L1 (BD Pharmingen) with the corresponding isotype control Rat IgG2a, λ (BD Pharmingen).

Trifecta Modulation—

Isolated KL cells were resuspended in SFEMII (StemCell Technologies) supplemented with 50 ng/ml of recombinant human SCF (StemCell Technology), 50 ng/ml of Mouse TPO (StemCell Technology), 50 ng/ml of Recombinant Mouse IL-3 (R&D SYSTEMS), Recombinant Mouse IFN-β (1000U/ml) (R&D SYSTEMS), Mouse IFN-γ (5 ng/ml) (R&D SYSTEMS) and 1 μg/ml of human Ploy (I:C) (Polyinosinic-polycytidylic acid) (InvivoGen).

Western Blot—

Murine KL cells were homogenized in RIPA buffer (20 mM Tris pH 8.0, 150 mM NaCl, 0.1% SDS, 0.5% DOC, 0.5% triton X-100) with protease inhibitors cocktail (Roche). Cell lysates equivalent to 50 μg of total protein were fractionated on 4%-20% SDS-polyacrylamide gradient gels (Bio-Rad) and transferred to nitrocellulose membranes (0.2 μm, Bio-Rad). Membranes were blocked with 5% BSA at room temperature for 1 hour and then incubated overnight with anti-PD-L1 (Santa Cruz Biotechnology), anti-Rabbit GAPDH (Cell Signaling TECHNOLOGY). Detection was performed by using anti-rabbit IgG, HRP-linked antibodies.

qRT-PCR—

To measure expression levels of PD-L1 gene in KL cells. Total RNA was extracted from KL cells and treated at 42° C. for 30 min with 100 μl of extraction buffer (Arcturus Picopure, Applied Biosystems), then subject to different washing steps and eluted in 15 ul of elution buffer according to manufacturer's instruction. RNA was quantified by nanodrop spectrophotometer followed by reverse transcription and pre-amplification using ABI Reverse Transcription and Taqman PreAmp Kit (Applied Biosystems) according to the manufacturer's instruction. TaqMan gene expression assays (Applied Biosystems) were performed on triplicate samples using a 7900HT fast real-time PCR system (Applied Biosystems). Data were normalized relative to GAPDH house keeping gene.

Confocal Microscopy and Immunofluorescence of HSCs—

Bone marrow extracted from femur and tibiae of 8 weeks old NOD and B6 mice were embedded in OCT and snap frozen in −80° C. N-methylbutane chilled in a slurry of ethanol and dry ice. Sections (7 μm) were prepared using a Microtome and air dried then stained with the corresponding antibodies. Images were captured on Zeiss LSM 510 Meta confocal microscope (Carl Zeiss SpA). Details of the staining procedure can be found in supplemental procedures.

Murine GWAS Assays—

Methods for MTA 1.0 and HTA 2.0 Affymetrix Microarray.

Genome-wide expression analysis was performed following Affymetrix GeneChip WT Pico protocol. RNA isolation was conducted using Arcturus PicoPure RNA Isolation Kit (Applied Biosystems) and then diluted to roughly 1.0 ng. RNA integrity was assessed for all RNA samples and the final concentration was measured on a Bioanalyzer using RNA Pico Chips (Agilent Technologies). Only RNA with a RIN score of 7 or higher were used. Between 1-2 ng was used as template to construct cRNA through a series of reactions involving cDNA synthesis, adaptor synthesis and a 16 hr amplification step (Affymetrix). Following cRNA purification and quantiation, ss-cDNA was synthesized, fragmented and labeled (Affymetrix). Each MTA 1.0 or HTA 2.0 Genechip was hybridized for 17 hrs at 45 C. Arrays were then stained on a FS450 Fluidic station (Affymetrix) and scanned on a Gene Chip 7G Scanner (Affymetrix). Probe intensities were normalized according to a log scale robust multi-array analysis (Expression Console-RMA, Affymetrix) method and normalized intensities were plotted with Spotfire 6.0 (Perking-Elmer).

Statistical Analysis—

Unless otherwise indicated, all data are shown as mean±SEM. Statistical analysis was performed using the unpaired Student t test. A two-sided value of P≤0.05 was considered statistically significant. The Kaplan-Meier curve with the Wilcoxon test was used to analyze the development of diabetes in mice. Statistical analysis was performed using GraphPad Prism software (GraphPad Software, Inc., La Jolla, Calif.).

Results

PD-L1 is Defective in HSCs from NOD Mice—

In order to identify any potential immunoregulatory defects in hematopoietic stem cells (HSCs) in mice prone to autoimmune diabetes, we firstly performed a wide transcriptomic profiling for immunoregulatory, anti-inflammatory and costimulatory molecules of murine HSCs from NOD mice and compared it with those obtained from C57BL/6 mice. Sca-1$^+$Lineage$^-$c-kit$^+$HSCs, (KLS) obtained from NOD showed at transcriptomic profiling a decreased expression of PD-L1 transcript as compared to those from HSCs obtained from C57BL/6 mice (FIG. 8A). We next used a wide range of techniques in order to confirm PD-L1 defect in NOD HSCs. First, we performed Western blotting assays in order to determine the expression of PD-L1 in KLS cells from NOD and compare it to C57BL/6 mice, we used GAPDH as internal control (FIG. 8B). After quantification of the Western blotting assays, a decrease in PDL-1 relative expression was evident in NOD compared to C57BL/6 mice (FIG. 8C). PD-L1 mRNA expression AS measured by RT-PCR in KLS cells confirmed the reduced PD-L1 mRNA expression in NOD HSCs (FIG. 8D). Fewer PD-L1+ cells and an overall reduced PD-L1 expression was evident in normoglycemic NOD mice in different bone marrow progenitors, namely in Sca-1$^+$Lineage$^-$c-kit$^+$ HSCs (KLS) cells, in Lineage-c-kit+ (KL) cells, in long-term repopulating HSCs (CD41$^-$ CD48$^-$ CD150$^+$ cells) and (CD244$^-$ CD48$^-$ CD150$^+$) as compared to C57BL/6 mice. (FIGS. 8F-8L). Interestingly, PD-L1 defect was mainly restrained to the HSC populations in NOD mice, as other bone marrow-derived immune relevant cells (e.g.; B220$^+$ B lymphocytes cells, CD11c$^+$ dendritic cells and F4/80+ macrophages) were not defective in PD-L1 (data not shown). Other costimulatory molecules (e.g.; PD-L2, PD-1, CD40, CD80 and CD80) were evaluated as well, and we did notice any significant difference between NOD and C57BL/6 HSCs obtained from bone marrow or spleen (data not shown), suggesting the unicity of PD-L1 defect. We sought then to explore any association of PD-L1 defect with age or disease status, and thus we performed flow cytometry analysis on bone marrow and splenocytes extracted-KL cells of NOD and C57BL/6 mice, respectively at 4 weeks, 10 weeks and above 16 weeks. We noticed a slight decline in the number of PD-L1+ cells in both strain. We then aimed at understanding the relevance of PD-L1 within the HSC niche, and thus analyzed with confocal imaging bone marrow tissue from NOD and C57BL/6, determining that PD-L1 is defective in HSCs in NOD mice (data not shown). In order to asses if hyperglycemia may play a role in this defect or if a high HSC turnover with increased apoptosis may generate immature HSCs in NOD mice, we tested the effect of high glucose on PD-L1 expression in HSCs from NOD and C57BL/6 mice and quantify their turnover and apoptotic rate. Isolated KL cells from NOD and C57BL/6 mice were cultured for 3 days in high glucose (20 and 35 mM)). While some changes were evident, no particular pattern suggested the existence of any potential high glucose-associated effect on PD-L1 expression (data not shown). Then, we performed a proliferation assay on CFSE labelled-HSCs from NOD and from C57BL/6 mice at baseline, when cultured for 24 hours and when cultured for 72 hours in SFEMII media. No differences in the proliferation rate were evident among HSCs from NOD or C57BL/6 (data not shown). We have further studied the apoptotic rate of HSCs from NOD and from C57BL/6 mice at baseline, after 24 hours of culture and after 72 hours of culture. Although at baseline, HSCs from NOD displayed a higher percentage of AnnexinV+/7-AAD− apoptotic cells as compared with HSCs from C57BL/6, after 24 hours and 72 hours of culture, an opposite scenario was evident with more apoptotic HSCs in C57BL/6 as compared to HSCs from NOD (data not shown). Our data confirmed the existence of a HSC-specific defect in PD-L1 expression in NOD mice, mainly restrained to hematopoietic stem cells populations.

Genetically Engineered NOD HSCs Abrogate Autoimmune Response In Vitro—

Figure 9H:
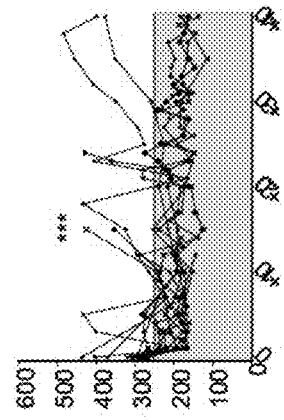
FIGS. 9H-9K are graphical representations of reversal of diabetes in NOD-Hyperglycemic treated with untransduced KL cells (FIG. 9K) and PD-L1.Tg KL cells (FIG. 9I) as demonstrated by blood glucose levels following administration of $3 \times 10^6$ untransduced KL cells or PD-L1.Tg KL cells. No reversal was achieved with doxycycline (FIG. 9J)

We tested the effect of a genetic-based engineering approach to overcome PD-L1 defect in NOD HSCs. We genetic engineered ex vivo murine KL cells and generate PD-L1$^+$.Tg HSCs from NOD mice by a third-generation self-inactivating lentiviral vectors (LV), which has a strong potential use in vivo because of its high efficiency and low risk of genotoxicity (Kevin D. Bunting and Cheng-Kui Qu, 2014, Methods in Molecular Biology, 1185, DOI 10.1007/978-1-4939-1133-2_21) and explore their effect on the onset of experimental autoimmune diabetes in NOD mice. Isolated murine HSCs (KL) were transduced with PD-L1 pseudoviral particles previously obtained by infecting HEK 293TN producer cells with a lentivirus vector containing PD-L1 gene whose expression was under the control of a doxycycline promoter, and a fluorescent marker designed as ZsGreen. We thus successfully generated PD-L1$^+$.Tg HSCs with an efficiency of 60% positive PD-L1$^+$ cells as compared to nearly 7% pre-transduction (FIGS. 9A-9C). An increased MFI was evident as well (pre-transduction=5.6±1.9; post-transduction=47.8±4.8). Immunofluorescence nicely depicted the increased surface PD-L1 expression after transduction with PD-L1 LV (data not shown). Genome wide analysis of the newly generated PD-L1$^+$.Tg HSCs confirmed the PD-L1 upregulation of PD-L1 by nearly a 327-fold increase compared to the Mock-LV transduced HSCs (data not shown). We then explored the immunoregulatory properties of newly generated PD-L1$^+$.Tg HSCs in an autoimmune setting in vitro. PD-L1$^+$ Tg.HSCs generated from normoglycemic NOD mice were cocultured at 3 different ratios to CD4+ CD25$^-$ T cells (1:1; 1:5 and 1:10) with CD11c$^+$ DCs and BDC2.5 transgenic CD4$^+$ CD25− T cells in the presence of the islet mimotope peptide BDC2.5. IFN-γ$^+$ CD4$^+$ CD25$^-$ T cells, as quantified by flow cytometry, showed a significant decrease when coculture with PD-L1$^+$.Tg HSCs at high ratio (p<0.005) compared with non transduced HSCs (KL cells) (FIGS. 9D and 9E). When PD-L1$^+$.Tg HSCs were pre-cultured with an anti-PD-L1 blocking mAb, the aforementioned immunoregluatory effect was severely hampered (data not shown). The PD-L1 dependent immunoregulatory properties were confirmed by using the CD8-dependent assay where PD-L1$^+$.Tg HSCs were cocultured at 3 different ratios (1:1; 1:5 and 1:10) with CD11c$^+$ DCs and 8.3 NOD transgenic CD8$^+$ T cells in the presence of the islet mimotope peptide IGRP (data not shown). We then tested the immunoregulatory effects of PD-L1$^+$.Tg HSCs in a non autoimmune specific assay. CD4$^+$ CD25$^-$ T cells extracted from NOD normoglycemic were stimulated by soluble anti-CD$^3$/anti-CD28 and cocultured with PD-L1$^+$.Tg HSCs at 3 different ratios to CD4$^+$ CD25$^-$ T cells (1:1; 1:5 and 1:10). The immunoregulatory effect was confirmed with a significant decrease in the percentage of IFN-γ+ CD4+ CD25− T cells when PD-L1+.Tg HSCs were added, although less evident as compared to the autoimmune assay, but still PD-L1 dependent (FIGS. 9F and 9G).

Genetically Engineered NOD HSCs Reverted Hyperglycemia—

Figure 9I:
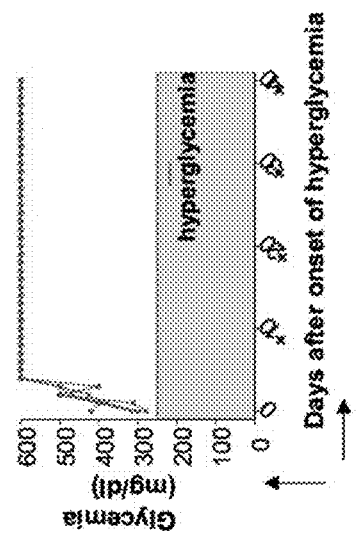
Figure 9J:
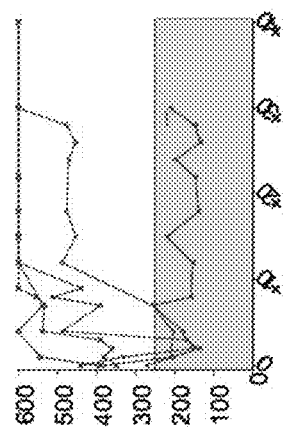
Figure 9K:
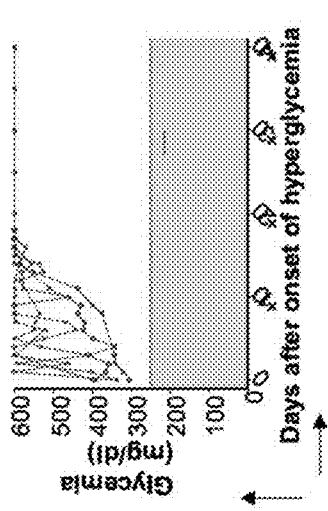
Figure 12:
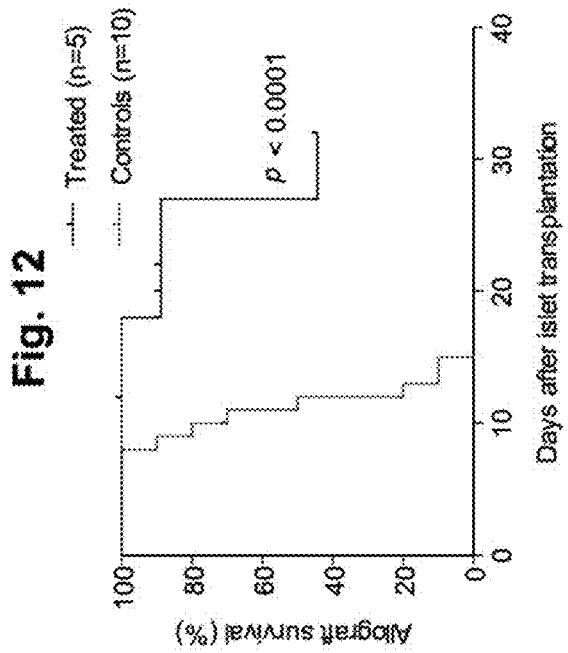
FIG. 12 shows that mice treated with PGE$_2$-stimulated HSC have delayed islet allograft rejection. Similar strategy can be used in general to prevent and also treat allograft rejections.
Figure 11:
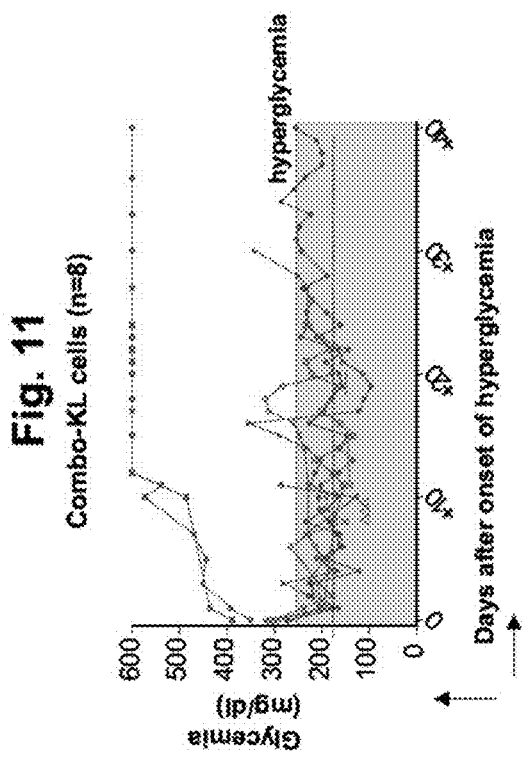
FIG. 11 shows the effect of dual PGE$_2$ and dexamethasone-stimulated KL cells in normalizing hyperglycemia in NOD mice after the onset of hyperglycemia. Each line represents the blood sugar of a test NOD mouse. The KL cells were stimulated ex vivo prior to implantation into the recipient mouse shortly after the onset of hyperglycemia.

In order to evaluate the immunoregulatory properties in vivo of the newly generated PD-L1+.Tg HSCs, newly hyperglycemic NOD mice were adoptively transferred with 3×10$^6$ PD-L1+.Tg HSCs (FIG. 9I) or 3×10$^6$ non-transduced (unmanipulated) HSCs (FIG. 9K) respectively. PD-L1+.Tg HSCs successfully reverted hyperglycemia in 100% of treated hyperglycemic NOD mice with 20% of treated mice remained normoglycemic till the completion of the study, while none of untreated hyperglycemic NOD mice (FIG. 9H) or of hyperglycemic NOD mice treated with doxycycline (FIG. 9J) reverted to normoglycemia. When untransduced HSCs were used, 1 hyperglycemic NOD mouse reverted to normoglycemia and 1 showed a mild transient improvement of glycemic levels, (data not shown). The pancreas immuno-histopathology of PD-L1+.Tg HSCs-treated hyperglycemic NOD mice revealed no evidence of infiltration of the islets or mild lymphocyte infiltration (data not shown), with preserved insulin staining as compared to hyperglycemic untreated NOD, showing a better reduced insulitis score. Immunophenotype of PD-L1+.Tg HSCs-treated hyperglycemic NOD-mice showed at day 14 after treatment a two fold increase in the percentage of FoxP3+ regulatory CD4+ T cells as compared to untreated mice, while no changes were observed in the percentage of IFN-γ+ and IL-17+ CD4+/CD8+ T cells (data not shown). Quantification of IFN-γ−producing cells in an ex-vivo assay of splenocytes challenged with islets peptides at day 40 (BDC2.5, IGRP, GAD-65 and insulin) revealed a reduction of IFN-γ+ cells in PD-L1+.Tg HSCs-treated hyperglycemic NOD-mice as compared to untreated (data not shown).

Genetically Engineered HSCs Traffic to the Pancreas in Hyperglycemic NOD Mice—

To explore the fate of infused PD-L1+.Tg HSCs in NOD mice, we performed a set of tracking experiments in the pancreas, the spleen, pancreatic draining lymph node (PLN) and bone marrow by using the. GFP tracer designed as ZsGreen within PD-L1+.Tg HSCs. PD-L1+.Tg HSCs were adoptively transferred into normoglycemic and hyperglycemic NOD mice and tissues were harvested after 1 day, 7 days and 14 days from infusion. GFP+ cells and GFP (ZsGreen mRNA) were quantified in all tissues by flow cytometry and RT-PCR respectively. PD-L1+.Tg HSCs once infused into hyperglycemic NOD preferentially traffic to the pancreas (data not shown) and home to a lower extent to the spleen and PLN (data not shown). While, PD-L1+.Tg HSCs preferentially home to bone marrow into normoglycemic NOD (data not shown). GFP+ cells were visualized by confocal imaging into the pancreas of PD-L1+.Tg HSCs treated hyperglycemic, but not normoglycemic, NOD mice NOD (data not shown). Luminescence images of NOD-hyperglycemic adoptively transferred with Luciferase+PD-L1.Tg KL cells within 24 hours of treatment further confirmed our data. In conclusion, we hereby confirmed a substantial homing of PD-L1+ HSCs to the pancreas in hyperglycemic NOD. We can now propose a working hypothesis, in which PD-L1+.Tg HSCs traffick into the pancreas and delete via PD-L1 dependent mechanism effector autoimmune T cells.

Pharmacologically Modulated HSCs Abrogate Autoimmune Response In Vitro—

The use of a genetic approach to cure T1D might not be an easy task, we explore the feasibility of a PD-L1 pharmacological modulation by small molecules. We tested the ability of single agents and of a a cocktail of agents to upregulate PD-L1. We came out with a cocktail of 3 agents (that we named Trifecta: IFN-γ, IFN-β, PolyI:C) capable of strongly upregulating PD-L1, (from nearly 6% of PD-L1+ cells in a population of HSCs up to 65% of PD-L1+ cells in the population after treatment with Trifecta) and creating programmed HSCs (pHSCs). Immunofluorescence nicely depicted the increased PD-L1 surface expression after modulation with small molecules, a combination of growth factors (SCF, TPO, IL-3, IL-6, IFN-B, IFN-g and poly I:C) (data not shown). Genome wide analysis confirmed the upregulation of PD-L1 in pHSCs with nearly a 13-fold increase compared to the unmodulated HSCs (data not shown). We then explored the immunoregulatory properties of pHSCs in an autoimmune setting. pHSCs generated from normoglycemic NOD mice were cocultured at 3 different ratios to CD4+ CD25− T cells (1:1; 1:5 and 1:10) with CD11c+ DCs and BDC2.5 transgenic CD4+CD25− T cells in the presence of BDC2.5 peptides. The quantification by flow cytometry of IFN-γ+ CD4+ CD25− T cells revealed a pronounced and significant decrease when pHSCs were added (p<0.005) compared to controls (data not shown). When pHSCs were pre cultured with an anti-PD-L1 blocking mAb the immunoregluatory effect was hampered (data not shown). The PD-L1 dependent immunoregulatory properties were confirmed by using the CD8-dependent assay where pHSCs were cocultured at 3 different ratios (1:1; 1:5 and 1:10) with CD11c+ DCs and 8.3 NOD transgenic CD8+ T cells in the presence of the islet mimotope peptide IGRP. We then tested the immunoregulatory effects of pHSCs in a non autoimmune specific assay. CD4+ CD25− T cells extracted from NOD normoglycemic were stimulated by soluble anti-CD3/anti-CD28 and cocultured with pHSCs at 3 different ratios to CD4+ CD25− T cells (1:1; 1:5 and 1:10). The immunoregulatory effect was confirmed with a significant decrease in the percentage of IFN-γ+ CD4+ CD25− T cells when pHSCs were added although less evident as compared to the autoimmune assay, but still PD-L1 dependent (data not shown). This strongly confirms that pHSCs are endowed with PD-L1-dependent regulatory properties ex vivo.

Pharmacologically Modulated HSCs Reverted Hyperglycemia—

In order to evaluate the immunoregulatory properties in vivo of pHSCs, newly hyperglycemic NOD mice were adoptively transferred with 3×10$^6$ pHSCs. Infused pHSCs successfully reverted diabetes in 40% of NOD mice with 30% of treated hyperglycemic NOD mice remaining normoglycemic till the completion of the study at day 40. Kaplan-Meier curve showed a stronger effect of PD-L1+.Tg HSCs in reverting hyperglycemia in NOD mice, with pHSCs performing a little bit less better. The immuno-histopathology analysis of the pancreas of pHSC-treated hyperglycemic NOD mice revealed no evidence of infiltration of the islets or mild lymphocyte infiltration with preserved insulin staining and reduced insulitis score as compared to untreated hyperglycemic NOD mice. Immunophenotype of treated NOD-mice showed at day 40 after treatment a reduction in the percentage of IFN-γ+ CD4+ and IL−17 and IFN-γ+ CD8+ T cells (data not shown). while no effect on Tregs (FoxP3+ regulatory CD4+ T cells) was detected. Quantification of IFN-γ-producing cells in an ex-vivo assay of splenocytes challenged with islets peptides at day 40 (BDC2.5, IGRP, GAD-65 and insulin) revealed a reduction of IFN-γ$^+$ cells pHSC-treated hyperglycemic NOD mice (data not shown).

PD-L1 Defect is Evident in Human HSCs from T1D Individuals—

To assess whether individuals with T1D displayed immunoregulatory defects in hematopoietic stem cells similar to the preclinical model, PD-L1 expression was analyzed on HSCs extracted from the peripheral blood of individuals with T1D and healthy controls. In line with our findings in NOD mice, fewer PD-L1$^+$ CD34$^+$ cells were detectable in T1D individuals as compared to healthy subjects (T1D=9.5% vs. controls=23.5%; p<0.001), (FIGS. 10A-10C). A western blot analysis and PCR analysis performed on RNA extracted from CD34$^+$cells previously isolated from PBMCs, confirmed PD-L1 reduced expression in HSCs obtained from healthy subjects as compared to those obtained from T1D individuals (FIGS. 10D-10F). However, other immune relevant cells (e.g.; CD19$^+$ B lymphocytes cells, CD11c$^+$ dendritic cells and CD16$^+$ cells) were not defective in PD-L1 (data not shown), thus confirming that PD-L1 defect was mainly restrained to the hematopoietic stem cell populations in T1D individuals. We look at a confocal imaging of HSCs, by determining the merging of PD-L1 and CD34, in their primary site and niche (bone marrow) and determined that a PD-L1 defect is evident at their own niche as well (data not shown). We further looked at the frequencies of other costimulatory molecules (e.g.; PD-L2 and PD-1) on peripheral HSCs from T1D individuals and healthy controls, which did not appear to be reduced in T1D individuals. (data not shown). Next, we wanted to determine the effect of high glucose on PD-L1 expression on HSCs. PBMCs were isolated from peripheral blood of T1D individuals and CD34$^+$ cells were sorted by magnetic beads. CD34$^+$ cells (HSCs) were cultured for 3 days in different conditions (normal glucose, 20 mM high glucose and 35 mM high glucose). While some changes were evident in line with our findings in NOD mice, no particular pattern suggested the existence of any potential high glucose-associated effect on PD-L1 expression (data not shown). Then, we performed a proliferation assay on CFSE labelled-HSCs from T1D individuals and controls, when cultured for 24 and 72 hours in SFEMII media. This was aimed to assess any apoptotic or survival-bias in our expression analysis. Our data indicated no difference in the proliferation rate of HSCs from T1D individuals and controls (data not shown). We have further studied HSC apoptotic rate. Although at baseline, HSCs from T1D displayed a significantly higher percentage of AnnexinV$^+$/7-AAD− apoptotic cells as compared with HSCs from HC, this was not evident after 24 and 72 hours of culture, as both HSCs from T1D and HC individuals displayed a similar apoptotic rate (data not shown). To confirm that the mobilization of HSCs cells (CD34$^+$) is not a therapeutic option in the absence of a clear restoration of PD-L1 expression, we evaluated the mobilization properties of HSCs in T1D individuals. We thus analyzed PD-L1 expression in a clinical trial (NCT01102699) in which 6 T1D individuals underwent HSCs mobilization with hrG-CSF (5 µg/kg). While CD34$^+$ cells significantly increased in healthy controls, an impaired mobilization of CD34$^+$ was observed in T1D individuals. This data confirms the existence of a HSC "mobilopathy" in T1D individuals. HSC immunephenotyping before and after mobilization with anti-CXCR4 (Plerixafor) in 5 controls and 8 T1D individuals. The percentage of CD34$^+$ PD-L1$^+$ cells decrease after in both T1D and controls, highlighting that CD34$^+$ cells require an in vitro manipulation to overturn PD-L1 defect and recover their immunoregulatory properties (data not shown).

Pharmacologically Modulated HSCs Abrogate Autoimmune Response In Vitro—

To overcome PD-L1 deficiency in human HSCs, we tested the effect of the same cocktail of small molecules that we developed in NOD mice. First, we evaluated PD-L1 expression in HSCs isolated from T1D individuals prior and post-modulation with a cocktail of small molecules. The newly human programmed HSCs (pHSCs) displayed an upregulation of PD-L1 expression as compared to unmodulated-HSCs. Immunofluorescence nicely depicted the increased surface PD-L1 expression after modulation with small molecules, a combination of growth factors (SCF, TPO, IL-3, IL-6, IFN-B, IFN-g and poly I:C) (data not shown). Genome wide analysis of the pHSCs confirmed the upregulation of PD-L1 with nearly a 26-fold increase compared to the unmodulated HSCs (data not shown). To study whether HSCs cells or pHSCs isolated from individuals with T1D possess immunoregulatory functions ex vivo, PBMCs depleted of HSCs were cocultured with HSCs or hpHSCs at 3 different ratios to PBMCs (1:1; 1:5 and 1:10) in the presence of insulin-associated autoantigen-2 (I-A2), and IFN-γ production by I-A2 stimulated PBMCs was assessed in an ELISPOT assay. Interestingly, compared with PBMCs-IA-2-stimulated, the addition of HSCs resulted in significantly (P≤0.05) decrease of IFN-γ production. The suppression was more pronounced when hpHSCs were added (data not shown), suggesting that HSCs and pHSCs are endowed with immunoregulatory activity. To further confirm that the main immunosuppressive effect exerted by HSCs was mainly due to PD-L1, we performed another Elispot assay to assess IFN-γ production by PBMCs stimulated with IA-2 peptide, and pHSCs in the presence of anti-PD-L1 blocking Ab or control Ab. Ab-mediated PD-L-1 blockage hampered the immunoreglautory effect already exerted by pHSCs as revealed by the absence of an evident reduction in the percentage of IFN-γ$^+$ PBMCs (data not shown). We then tested the immunoregulatory effects of pHSCs in a non specific anti-CD3/CD28 assay. CD4$^+$ T cells extracted from HC individuals and stimulated by soluble anti-CD3/anti-CD28 were cocultured with HSCs or with pHSCs at 3 different ratios to CD4$^+$ T cells (1:1; 1:5 and 1:10). An evident and significant decrease in the percentage of IFN-γ$^+$ CD4$^+$ T cells was remarkably observed when pHSCs were added (data not shown). The addition of anti-PD-L1 blocking Ab clearly abrogated the immunosuppressive effect of pHSCs mainly conferred by PD-L1 (data not shown). This strongly confirms that HSCs and pHSCs are endowed with PD-L1-dependent regulatory properties ex vivo. In order to evaluate the immunoregulatory properties in vivo of the newly generated pHSCs, NRG-Akita hyperglycemic mice have firstly received human PBMCs (10×10$^6$ cells) followed by islet transplantation with human islets (~2000IEQ) and were then adoptively transferred with 1×10$^6$ pHSCs (data not shown). Infused pHSCs successfully maintained NRG-Akita mice normoglycemic in NRG-Akita mice till the completion of the study. Kaplan-Meier curve showing reversal of glycemia in different treated groups (data not shown). The immuno-histopathology analysis of the pancreas of treated mice with pHSCs revealed no evidence of infiltration of the islets or mild lymphocyte infiltration (data not shown) with preserved insulin staining as compared to hyperglycemic untreated NOD and a reduced insulitis score.

The references cited herein and throughout the specification are incorporated herein by reference.

1. Bluestone J A, et al. Genetics, pathogenesis and clinical interventions in type 1 diabetes. Nature, 2010 Apr. 29; 464(7293):1293-300.
2. Ann. Intern. Med., 128(7):517-23.1998, Effect of intensive therapy on residual beta-cell function in patients with type 1 diabetes in the diabetes control and complications trial. A randomized, controlled trial. The Diabetes Control and Complications Trial Research Group.
3. Pescovitz M D, et al. 2009, Rituximab, B-lymphocyte depletion, and preservation of beta-cell function. N. Engl. J. Med. 361(22):2143-52.
4. Couri C E, et al. 2009, C-peptide levels and insulin independence following autologous nonmyeloablative hematopoietic stem cell transplantation in newly diagnosed type 1 diabetes mellitus. JAMA, 301(15):1573-9.
5. D'Addio F, et al. 2014, Autologous nonmyeloablative hematopoietic stem cell transplantation in new-onset type 1 diabetes: a multicenter analysis. Diabetes, 63(9):3041-6.
6. Steptoe R J, et al. 2005, Autoimmune diabetes is suppressed by transfer of proinsulin-encoding Gr-1+ myeloid progenitor cells that differentiate in vivo into resting dendritic cells. Diabetes, 54(2):434-42.
7. Bachar-Lustig E, et al. 1995, Megadose of T cell-depleted bone marrow overcomes MHC barriers in sublethally irradiated mice. Nat. Med., 1(12):1268-73.
8. Gur H, et al. 2005, Immune regulatory activity of CD34+ progenitor cells: evidence for a deletion-based mechanism mediated by TNF-alpha. Blood, 105(6):2585-93.
9. Rachamim N, et al. 1998, Tolerance induction by "megadose" hematopoietic transplants: donor-type human CD34 stem cells induce potent specific reduction of host anti-donor cytotoxic T lymphocyte precursors in mixed lymphocyte culture. Transplantation, 65(10):1386-93.
10. Fiorina P, et al. 2008, Targeting CD22 reprograms B-cells and reverses autoimmune diabetes. Diabetes, 57(11):3013-24.
11. Kang E M, et al. 2005, Hematopoietic stem cell transplantation prevents diabetes in NOD mice but does not contribute to significant islet cell regeneration once disease is established. Exp. Hematol. 33(6):699-705.
12. Fiorina P, et al. 2011, Targeting the CXCR4-CXCL12 axis mobilizes autologous hematopoietic stem cells and prolongs islet allograft survival via programmed death ligand 1. J. Immunol., 186(1):121-31.
13. D'Addio F, et al. 2011, The link between the PDL1 costimulatory pathway and Th17 in fetomaternal tolerance. J. Immunol., 187(9):4530-41.
14. Yokosuka T, et al. 2012, Programmed cell death 1 forms negative costimulatory microclusters that directly inhibit T cell receptor signaling by recruiting phosphatase SHP2. J. Exp. Med., 209:1201-17.
15. Ansari M J, et al. 2003, The programmed death-1 (PD-1) pathway regulates autoimmune diabetes in nonobese diabetic (NOD) mice. J. Exp. Med., 198(1):63-9.
16. Petrelli A, et al. 2011, IL-21 is an antitolerogenic cytokine of the late-phase alloimmune response. Diabetes, 60(12):3223-34.

---

What is claimed:

1. A method of treating Type 1 diabetes (T1D) by suppressing immune-mediated destruction of pancreatic islet β-cells, the method comprising:
    administering to a subject with T1D a composition comprising a population of genetically modified PD-L1+-expressing hematopoietic stem cells (HSCs) in an amount effective to suppress immune-mediated destruction of pancreatic islet β,
    wherein the subject is not administered a myeloablative therapy.

2. The method of claim 1, wherein the population of PD-L1+-expressing HSCs comprise an exogenous copy of a nucleic acid encoding PD-L1.

3. The method of claim 2, wherein the nucleic acid is cDNA or genomic DNA.

4. The method of claim 3, wherein the genomic DNA is integrated into the genome of the cells.

5. The method of claim 2, wherein the nucleic acid is introduced into the cells via a vector.

6. The method of claim 1, wherein the population of PD-L1+-expressing HSCs is obtained by genetically modifying HSCs obtained from bone marrow, umbilical cord, amniotic fluid, chorionic villi, placental blood, or mobilized peripheral blood.

7. The method of claim 1, wherein the cells are mammalian cells or human cells.

8. The method of claim 1, wherein the population of PD-L1+-expressing HSCs are autologous, allogeneic, or xenogeneic to the subject.

9. The method of claim 1, wherein the administration is intravenous or transplantation.

10. A method of treating the onset of pediatric Type 1 diabetes (T1D), the method comprising:
    administering to a pediatric subject with new onset T1D a therapeutically effective amount of a composition comprising a population of genetically modified PD-L1±-expressing hematopoietic stem cells,
    wherein the pediatric subject is not administered a myeloablative therapy.

11. The method of claim 10, wherein the population of HSCs comprise an exogenous copy of a nucleic acid encoding PD-L1.

12. The method of claim 10, wherein the population of HSCs is obtained by genetically modifying HSCs obtained from bone marrow, umbilical cord, amniotic fluid, chorionic villi, placental blood, or mobilized peripheral blood.

13. The method of claim 10, wherein the population of HSCs are autologous, allogeneic, or xenogeneic to the subject.

14. The method of claim 10, wherein the administration is intravenous or transplantation.

15. A method of treating the onset of adult Type 1 diabetes (T1D), the method comprising: administering to an adult subject with new onset T1D a therapeutically effective amount of a composition comprising a population of genetically modified PD-L1+-expressing hematopoietic stem cells,
    wherein the adult subject is not administered a myeloablative therapy.

16. The method of claim 15, wherein the population of HSCs comprise an exogenous copy of a nucleic acid encoding PD-L1.

17. The method of claim 15, wherein the population of HSCs is obtained by genetically modifying HSCs obtained from bone marrow, umbilical cord, amniotic fluid, chorionic villi, placental blood, or mobilized peripheral blood.

18. The method of claim 15, wherein the population of HSCs are autologous, allogeneic, or xenogeneic to the subject.

19. The method of claim 15, wherein the administration is intravenous or transplantation.

* * * * *

SEQUENCE LISTING

<160> NUMBER OF SEQ ID NOS: 2

<210> SEQ ID NO 1
<211> LENGTH: 531
<212> TYPE: DNA
<213> ORGANISM: Homo sapiens

<400> SEQUENCE: 1

```
atgaggatat ttgctgtctt tatattcatg acctactggc atttgctgaa cgccccatac      60
aacaaaatca accaaagaat tttggttgtg gatccagtca cctctgaaca tgaactgaca     120
tgtcaggctg agggctaccc caaggccgaa gtcatctgga caagcagtga ccatcaagtc     180
ctgagtggta agaccaccac caccaattcc aagagagagg agaagctttt caatgtgacc     240
agcacactga gaatcaacac aacaactaat gagattttct actgcacttt taggagatta     300
gatcctgagg aaaaccatac agctgaattg gtcatcccag aactacctct ggcacatcct     360
ccaaatgaaa ggactcactt ggtaattctg ggagccatct tattatgcct tggtgtagca     420
ctgacattca tcttccgttt aagaaaaggg agaatgatga tgtgaaaaaa atgtggcatc     480
caagatacaa actcaaagaa gcaaagtgat acacatttgg aggagacgta a              531
```

<210> SEQ ID NO 2
<211> LENGTH: 873
<212> TYPE: DNA
<213> ORGANISM: Homo sapiens

<400> SEQUENCE: 2

```
atgaggatat ttgctgtctt tatattcatg acctactggc atttgctgaa cgcatttact      60
gtcacggttc ccaaggacct atatgtggta gagtatggta gcaatatgac aattgaatgc     120
aaattcccag tagaaaaaca attagacctg gctgcactaa ttgtctattg ggaaatggag     180
```

```
gataagaaca ttattcaatt tgtgcatgga gaggaagacc tgaaggttca gcatagtagc      240
tacagacaga gggcccggct gttgaaggac cagctctccc tgggaaatgc tgcacttcag      300
atcacagatg tgaaattgca ggatgcaggg gtgtaccgct gcatgatcag ctatggtggt      360
gccgactaca agcgaattac tgtgaaagtc aatgccccat acaacaaaat caaccaaaga      420
attttggttg tggatccagt cacctctgaa catgaactga catgtcaggc tgagggctac      480
cccaaggccg aagtcatctg gacaagcagt gaccatcaag tcctgagtgg taagaccacc      540
accaccaatt ccaagagaga ggagaagctt ttcaatgtga ccagcacact gagaatcaac      600
acaacaacta atgagatttt ctactgcact tttaggagat tagatcctga ggaaaaccat      660
acagctgaat tggtcatccc agaactacct ctggcacatc ctccaaatga aaggactcac      720
ttggtaattc tgggagccat cttattatgc cttggtgtag cactgacatt catcttccgt      780
ttaagaaaag ggagaatgat ggatgtgaaa aaatgtggca tccaagatac aaactcaaag      840
aagcaaagtg atacacattt ggaggagacg taa                                   873
```